United States Patent [19]

Chiou et al.

[11] Patent Number: 5,378,286
[45] Date of Patent: Jan. 3, 1995

[54] METHOD OF PREPARING REDUCED FAT FOODS

[75] Inventors: Ruth G. Chiou; Cheryl C. Brown; Jeanette A. Little; Austin H. Young; Robert V. Schanefelt; Donald W. Harris; Keith D. Stanley; Helen D. Coontz; Carolyn J. Hamdan, all of Decatur; Jody A. Wolf-Rueff, Clinton, all of Ill.; Lori A. Slowinski, Madison, Wis.; Kent R. Anderson, Warrensburg, Ill.; William F. Lehnhardt, Decatur, Ill.; Zbigniew J. Witczak, Decatur, Ill.

[73] Assignee: A. E. Staley Manufacturing Co., Decatur, Ill.

[21] Appl. No.: 857,532

[22] Filed: Apr. 21, 1992

Related U.S. Application Data

[60] Division of Ser. No. 578,994, Sep. 6, 1990, abandoned, which is a continuation-in-part of Ser. No. 483,208, Feb. 20, 1990, abandoned.

[51] Int. Cl.$^6$ .................... C13K 1/06; C08B 30/00
[52] U.S. Cl. ........................... 127/36; 127/38; 127/40; 127/69; 127/70; 127/71; 127/1
[58] Field of Search .................. 127/36, 38, 40, 69, 127/70, 71, 1

[56] References Cited

U.S. PATENT DOCUMENTS

| 675,822 | 6/1901 | Duryea | 127/33 |
|---|---|---|---|
| 696,949 | 4/1902 | Duryea | 127/33 |
| 1,668,308 | 5/1928 | Ebert et al. | 127/40 |
| 1,692,817 | 11/1928 | Christman | 127/40 |
| 2,068,051 | 1/1937 | Canton | 426/578 |
| 2,131,064 | 9/1938 | Musher | 426/633 |
| 2,503,053 | 4/1950 | Kerr | 127/38 |
| 2,791,508 | 5/1957 | Rivoche | 426/573 |
| 2,805,995 | 9/1957 | Adelson | 252/33.6 |
| 2,978,446 | 4/1961 | Battista | 260/212 |
| 2,989,425 | 6/1961 | Bierke et al. | 127/36 |
| 3,023,104 | 2/1962 | Battista | 99/1 |
| 3,067,067 | 12/1962 | Etheridge | 127/71 |
| 3,093,486 | 6/1963 | Krett | 99/144 |
| 3,133,836 | 5/1964 | Winfrey | 127/71 |
| 3,197,337 | 7/1965 | Schink | 127/28 |
| 3,219,483 | 11/1965 | Goos | 127/28 |
| 3,351,489 | 11/1967 | Battista | 127/32 |
| 3,532,602 | 10/1970 | Seidman | 195/31 |
| 3,556,942 | 1/1971 | Hathaway | 195/31 |

(List continued on next page.)

FOREIGN PATENT DOCUMENTS

| 1016006 | 8/1977 | Canada | 99/1 |
|---|---|---|---|
| 0052899 | 2/1982 | European Pat. Off. | A23D 3/00 |
| 0237120 | 9/1987 | European Pat. Off. | A23D 3/00 |
| 0298561 | 1/1989 | European Pat. Off. | A23L 1/307 |
| 0327120 | 8/1989 | European Pat. Off. | A23D 5/00 |
| 0327288 | 8/1989 | European Pat. Off. | A23D 3/00 |

(List continued on next page.)

OTHER PUBLICATIONS

J. Jane et al., "Preparation and Properties of Small-Particle Corn Starch", *Cereal Chemistry*, vol. 69, pp. 280–283 (1992).

Tegge, "Produkte der sauren Stärkehydrolyse", Die Stärken, pp. 244–246 (1981). (English translation).

"Avicel RC in canned foods", bulletin No. RC-31, FMC Corp. (May 1972).

(List continued on next page.)

*Primary Examiner*—Paul Lieberman
*Attorney, Agent, or Firm*—Arnold, White & Durkee

[57] ABSTRACT

A food formulation having a reduced level of fat and/or oil is provided. The food formulation is a mixture of a foodstuff and a fragmented, amylopectin starch hydrolysate as a replacement for at least a substantial portion of the fat and/or oil of said food formulation. The fragmented starch hydrolysate is capable of forming an aqueous dispersion at about 20% hydrolysate solids exhibiting a yield stress of from about 100 to about 1,500 pascals. Also provided is a method of formulating a food containing a fat and/or oil ingredient comprising replacing at least a portion of said fat and/or oil ingredient with the fragmented, amylopectin starch hydrolysate. Examples of food formulations include those for margarine, salad dressings (pourable and spoonable), frostings, and frozen novelties.

27 Claims, 4 Drawing Sheets

U.S. PATENT DOCUMENTS

| | | | |
|---|---|---|---|
| 3,582,359 | 6/1971 | Horn | 426/573 |
| 3,586,536 | 6/1971 | Germino | 127/32 |
| 3,600,186 | 8/1971 | Mattson | 99/1 |
| 3,616,220 | 10/1971 | Nisbet et al. | 127/38 |
| 3,666,557 | 5/1972 | Jensen | 127/32 |
| 3,671,269 | 6/1972 | Germino | 99/139 |
| 3,674,555 | 7/1972 | Meyer et al. | 127/38 |
| 3,705,811 | 12/1972 | Yoshida | 99/91 |
| 3,717,475 | 2/1973 | Germino | 99/134 |
| 3,730,840 | 5/1973 | Sugimoto | 195/31 R |
| 3,830,697 | 8/1974 | Yoshida | 195/31 R |
| 3,879,212 | 4/1975 | Yoshida | 106/213 |
| 3,881,991 | 5/1975 | Kurimoto | 195/31 |
| 3,883,365 | 5/1975 | Forsberg | 127/60 |
| 3,928,062 | 12/1975 | Yamauchi | 127/60 |
| 3,962,465 | 6/1976 | Richter | 127/48 |
| 3,986,890 | 10/1976 | Richter | 127/38 |
| 4,009,291 | 2/1977 | Mitchell | 426/548 |
| 4,069,157 | 1/1978 | Hoover | 210/433 M |
| 4,137,094 | 1/1979 | Hughes | 127/1 |
| 4,143,163 | 3/1979 | Hutchison | 426/96 |
| 4,143,174 | 3/1979 | Shah | 426/570 |
| 4,192,900 | 3/1980 | Cheng | 426/578 |
| 4,199,374 | 4/1980 | Dwivedi | 127/60 |
| 4,209,503 | 6/1980 | Shah | 424/49 |
| 4,263,334 | 4/1981 | McGinley | 426/573 |
| 4,276,312 | 6/1981 | Merritt | 426/96 |
| 4,291,065 | 9/1981 | Zobel | 426/549 |
| 4,305,964 | 12/1981 | Moran | 426/99 |

(List continued on next page.)

FOREIGN PATENT DOCUMENTS

| | | | |
|---|---|---|---|
| 0340035 | 11/1989 | European Pat. Off. | A23J 3/00 |
| 0367064 | 5/1990 | European Pat. Off. | A23L 1/05 |
| 0372184 | 6/1990 | European Pat. Off. | C12P 19/16 |
| 0387940 | 9/1990 | European Pat. Off. | A23D 7/00 |
| 0443844 | 8/1991 | European Pat. Off. | A23L 1/09 |
| 0470870 | 2/1992 | European Pat. Off. | |
| 142646A | 7/1980 | German Dem. Rep. | A23L 1/24 |
| 161178A | 5/1985 | German Dem. Rep. | A23G 9/02 |
| 110957 | of 1897 | Germany | . |
| 60-160833 | 8/1985 | Japan | A21D 2/36 |
| 2247242 | 2/1992 | United Kingdom | . |
| WO87/04465 | 7/1987 | WIPO | C12P 7/06 |
| WO89/12403 | 12/1989 | WIPO | A23L 1/10 |
| WO90/00010 | 1/1990 | WIPO | A21D 8/06 |
| WO90/06343 | 6/1990 | WIPO | C08L 5/06 |
| WO90/15147 | 12/1990 | WIPO | C12P 19/14 |
| WO91/01091 | 2/1991 | WIPO | A23L 1/0522 |
| WO91/01092 | 2/1991 | WIPO | A23L 1/522 |
| WO91/07106 | 5/1991 | WIPO | A23L 1/308 |

OTHER PUBLICATIONS

"Avicel microcrystalline cellulose; the non-caloric ingredient", bulletin, American Viscose Corp.

"Avicel RC 581 Technical Bulletin", bulletin No. RC-11, FMC Corp., 11/69-IM.

"Avicel RC-591 in foods", bulletin No. RC-22, FMC Corp. (May 1971).

"Avicel RC in bakery products", bulletin No. RC-35, FMC Corp.

"Avicel pricing", bulletin, American Viscose Corp. (Jan. 1961).

"C9-112 microcrystalline starch", bulletin, A. E. Staley Mfg. Co. (Jan. 1972), with notes by A. H. Young.

"Food labelling; definitions of the terms cholesterol free, low cholesterol, and reduced cholesterol", 55 Fed. Reg. 29456 (1990).

"Food labelling; serving sizes", 55 Fed. Reg. 29517 (1990).

Low-fat pork sausage patty", formula sheet CFSF7 196211, A. E. Staley Mfg. Co.

"Nepol Amylose", market development bulletin No. 101, A. E. Staley Mfg. Co. (1962).

"New generation of foods with reduced fat", Food Engineering, pp. 23–26 (Jan. 1990).

"Paselli SA2; the natural alternative to fats and oils", product bulletin, AVEBE b.a., Foxhol., Holland, ref. No. 05.12.31.167 EE (Jun. 1988).

"RANNIE High Pressure Laboratory Homogenizer", service manual, Rannie a/s, Roholmsvej 8, DK-2620, Denmark (1988).

"Reduced oil salad dressing", technical publication, A. E. Staley Mfg. Co.

"Solve tough process filtration problems with Ceraflo ceramic systems", technical bulletin, lit. No. SD113, Feb. 1989 89-418, Millipore Corp. (1989).

"STA-SLIM starches", technical data sheet, TDS 507 096060, A. E. Staley Mfg. Co.

"Staley Formulation of Food Starch-Modified", new product review presented to U.S. Food and Drug Administration by A. E. Staley Mfg. Co. (Nov. 1990).

Ambler, "Centrifugation", Handbook of Separation Techniques for Chemical Engineers, pp. 4–60 to 4–88 (McGraw Hill 1988).

Applewhite, "Fats and fatty oils", Encyclopedia of Chemical Technology, vol. 9, pp. 795–831 (Kirk-Oth- (List continued on next page.)

U.S. PATENT DOCUMENTS

| | | | |
|---|---|---|---|
| 4,308,294 | 12/1981 | Rispoli | 426/564 |
| 4,423,084 | 12/1982 | Trainor | 426/589 |
| 4,477,480 | 10/1984 | Seidel | 426/578 |
| 4,492,714 | 1/1985 | Cooper | 426/602 |
| 4,510,166 | 4/1985 | Lenchin | 426/565 |
| 4,533,254 | 8/1985 | Cook | 366/176 |
| 4,536,408 | 8/1985 | Morehouse | 426/250 |
| 4,551,177 | 11/1985 | Trubiano | 106/210 |
| 4,560,559 | 12/1985 | Ottenburg | 426/19 |
| 4,587,131 | 5/1986 | Bodor | 426/603 |
| 4,591,507 | 5/1986 | Bodor | 426/604 |
| 4,643,773 | 2/1987 | Day | 127/30 |
| 4,670,272 | 6/1987 | Chen | 426/573 |
| 4,726,957 | 2/1988 | Lacourse | 426/578 |
| 4,728,526 | 3/1988 | Avera | 426/633 |
| 4,744,987 | 5/1988 | Mehra | 424/156 |
| 4,761,292 | 8/1988 | Augustine | 426/321 |
| 4,787,939 | 1/1989 | Barker | 127/37 |
| 4,810,646 | 3/1989 | Jamas | 435/101 |
| 4,814,195 | 3/1989 | Yokohama | 426/633 |
| 4,828,868 | 5/1989 | Lasdon | 426/633 |
| 4,832,977 | 5/1989 | Avera | 426/633 |
| 4,859,484 | 8/1989 | Bielskis | 426/96 |
| 4,869,919 | 9/1989 | Lowery | 426/604 |
| 4,885,180 | 12/1989 | Cochran | 426/241 |
| 4,886,678 | 12/1989 | Chiu | 426/578 |
| 4,911,946 | 3/1990 | Singer | 426/658 |
| 4,917,915 | 4/1990 | Cain | 426/573 |
| 4,937,091 | 6/1990 | Zallie | 426/582 |
| 4,942,055 | 7/1990 | Avera | 426/633 |
| 4,948,615 | 8/1990 | Zallie | 426/573 |
| 4,957,750 | 9/1990 | Cochran | 426/19 |
| 4,962,094 | 10/1990 | Jamas | 514/54 |
| 4,971,723 | 11/1990 | Chiu | 252/315.3 |
| 4,981,709 | 1/1991 | Furcsik | 426/565 |
| 4,988,531 | 1/1991 | Moore | 426/578 |
| 4,990,355 | 2/1991 | Gupta | 426/602 |
| 5,034,240 | 7/1991 | Tanaka | 426/607 |
| 5,035,904 | 7/1991 | Huang | 426/243 |
| 5,037,929 | 8/1991 | Rajagopalan | 426/578 |
| 5,051,271 | 9/1991 | Iyengar | 426/658 |
| 5,104,674 | 4/1992 | Chen et al. | 426/573 |
| 5,104,674 | 4/1992 | Chen et al. | 426/573 |
| 5,106,644 | 4/1992 | El-Nokaly | 426/603 |
| 5,110,612 | 5/1992 | Quarles | 426/573 |

OTHER PUBLICATIONS mer, eds., John Wiley & Sons 1980).

Atwell et al, "Characterization of quinoa starch", Cereal Chemistry, vol. 60, pp. 9–11 (1983).

Battista et al, "Colloidal macromolecular phenomena. Part II. Novel microcrystals of polymers", Journal of Applied Polymer Science, vol. 11, pp. 481–498 (1967).

Battista et al, "Microcrystalline cellulose", Industrial and Engineering Chemistry, vol. 54, pp. 20–29 (1962).

Bouchard et al, "High performance liquid chromatographic monitoring of carbohydrate fractions in partially hydrolyzed corn starch", J. Agric. Food Chem., vol. 36, pp. 1188–1192 (1988).

Dillon, "Gums and starches bulk up low-cal foods", Food Engineering (Jan. 1990).

Dziezak, "Emulsifiers: the interfacial key to emulsion stability", Food Technology, vol. 42, No. 10, pp. 171–186 (Oct. 1988).

Dziezak, "Membrane separation technology offers processors unlimited potential", Food Technology, pp. 108–113 (Sep. 1990).

Erdi et al, 37 Rheological characteristics of polymeric microcrystal-gels 38 , Journal of Colloid and Interface Science, vol. 28, pp. 36 –47 (1968).

Falkiewicz, "Avicel in suspensions-dispersion, rheology and colloid science", Soap, Cosmetics, Chemical Specialties, pp. 27–34 (Apr. 1979).

Faulkner et al. "Size reduction", Encyclopedia of Chemical Technology, vol. 21, pp. 132–162 (Kirk Othmer eds., John Wiley & Sons, 1983).

Ghiasi et al, "Effects of flour components and dough ingredients on starch gelatinization", Cereal Chemistry, vol. 60, No. 1, pp. 58–61 (1983).

Griffin, "Emulsions", Encyclopedia of Chemical Technology, vol. 8, pp. 900–930 (Kirk-Othmer, eds., John Wiley & Sons, 3d ed. 1979).

Jane et al, "Structure studies of amylose-V complexes and retrograded amylose by action of alpha amylases, and a new method for preparing amylodextrins", Carbohydrate Research, vol. 132, pp. 105–118 (1984).

Kerr, Chemistry and Industry of Starch, 2d ed., pp. 564–567 (Academic Press 1950).

Klinkowski, "Ultrafiltration", Encyclopedia of Chemical Technology, vol. 23, pp. 439–461 (Kirk-Othmer, eds., John Wiley & Sons, 3d ed. 1983).

Knightly, "The evolution of softeners and conditioners used in baked foods", The Bakers Digest, pp. 64–75 (Oct. 1973).

Koizumi et al, "High performance anion-exchange chromatography of homogenous D-gluco oligosaccharides and polysaccharides (polymerization degree equal to or greater than 50) with pulsed amphoteric detec- (List continued on next page.)

OTHER PUBLICATIONS tion", Journal of Chromatography, vol. 46, pp. 365–373 (1989).

Krog, "Functions of emulsifiers in food systems", J. Am. Oil Chemists' Society, vol. 54, pp. 124–131 (1978).

Lansky et al, "Properties of the fractions and linear subfractions from various starches", vol. 71, pp. 4066–4075 (1949).

Lavanchy et al, "Centrifugal separation", Encyclopedia of Chemical Technology, vol. 5, pp. 194–233 (Kirk-Othmer, eds., John Wiley & Sons, 3d ed., 1979).

Luu et al, "Model structure for liquid water, etc.", Travaux de la Societe de Pharmacie de Montpellier, vol. 41, No. 3, pp. 203–212 (1981) (Translation Attached).

Manley, Technology of Biscuits, Crackers and Cookies, pp. 335–347 (Ellis Horwood 1983).

Mason, "Chemistry with ultrasound", Critical Reports on Applied Chemistry, vol. 28, pp. 1–26, 91–98, 159–187 (Elsevier Science Publishers 1990).

Matthews, Legumes: Chemistry, Technology, and Human Nutrition, pp. 226–229 (Marcel Dekker 1989).

Matz, Cookie and Cracker Technology, pp. 163–167 (AVI Publishing 1968).

Mussulman et al, "Electron microscopy of unmodified and acid-modified corn starches", Cereal Chemistry, vol. 45, pp. 162–171 (1968).

Nara et al., "Study on relative crystallinity of moist potato starch", Starke/Starch, vol. 30, pp. 111–114 (1978).

Orr, "Size measurement of particles", Encyclopedia of Chemical Technology, vol. 21, pp. 106–131 (Kirk Othmer eds., John Wiley & Sons, 1983).

Pancoast et al, Handbook of Sugars, pp. 157–287 (AVI Publishing 1980).

Patterson, Hydrogenation of Fats and Oils, pp. 44–48, 173–182, 291–304 (Applied Science Publishers, 1983).

Paul et al, "Membrane technology", Encyclopedia of Chemical Technology, vol. 15, pp. 92–131 (Kirk-Othmer, eds., John Wiley & Sons, 3d ed. 1981).

Rees et al, "Homogenizers", Encyclopedia of Foods Engineering, pp. 467–472 (Hall et al eds., AVI Publ. 1986).

Reuter, "Homogenization", Encyclopedia of Food Science, pp. 374–376 (Peterson et al eds., AVI Publ. Co., 1978).

Reuther et al, "Structure of maltodextrin gels—a small angle X-ray scattering study", Colloid and Polymer Science, vol. 261. pp. 271–276 (1983).

Richards, Breads, Rolls and Sweet Doughs, pp. 92–95 (Peacock Business Press, 1973).

Richardson, "Molecular mobilities of instant starch gels determined by oxygen–17 and carbon–14 nuclear magnetic resonance", Journal of Food Science, vol. 53, pp. 1175–1180 (1988).

Russell et al, "Characterization of resistant starch from wheat and maize", Journal of Cereal Science, vol. 9, pp. 1–15 (1989).

Sanderson, "Polysaccharides in foods", Food Technology, pp. 50–57 and 83 (Jul. 1981).

Savage et al, "Effect of certain sugars and sugar alcohols on the swelling of cornstarch granules", Cereal Chemistry, vol. 55, No. 4, pp. 447–454 (1978).

Shannon et al, "Genetics and physiology of starch development", Starch: Chemistry and Technology, pp. 25–35 (Whistler et al eds., Academic Press 1984).

Sievert et al, "Enzyme resistant starch. I. Characterization and evaluation of enzymatic, thermoanalytical, and microscopic methods", Cereal Chemistry, vol. 66, pp. 342–347 (1989).

Spies et al, "Effect of sugars on starch gelatinization", Cereal Chemistry, vol. 59, No. 2, pp. 128–131 (1982).

Stadelman et al, Egg and Poultry Meat Processing, pp. 52–63 (Ellis Horwood 1988).

Swientek, "'Microfluidizing' technology enhances emulsion stability", Food Processing, pp. 152–153 (Jun. 1990).

Teot, "Resins, water-soluble", Encyclopedia of Chemical Technology, vol. 20, pp. 207–230 (John Wiley & Sons 1982).

Trout, "Pasteurization", Encyclopedia of Food Science, pp. 600–604 (Peterson et al eds., AVI Publ. Co., 1978).

Wang, "Meat processing I", Encyclopedia of Food Engineering, pp. 545–557 (AVI Publishing 1986).

Whistler et al, "Effect of acid hydrolysis on the retrogradation of amylose", Cereal Chemistry, vol. 25, No. 6, pp. 418–424 (1948).

White et al, "Predicting gelatinization temperatures of starch/sweetener systems for cake formulations by differential scanning calorimetry. I. Development of model." Cereal Foods World, vol. 35, No. 8, pp. 728–731 (Aug. 1990).

Wilhoft, "Recent developments on the bread staling problem", The Bakers Digest, pp. 14–20 (Dec. 1973).

Wurzburg, Modified Starches: Properties and Uses, pp. 18–23, 38–40, 244–245, and 251–252 (CRC Press, 1986).

Yamaguchi et al, "Electron microscopic observations of waxy maize starch", Journal of Ultrastructure Research, vol. 69, pp. 249–261 (1979).

Young, "Evaluation of microcrystals prepared from MIRA-QUIK C in the pilot plant spray dried in the presence of sodium carboxymethylcellulose (C9–112)", project report No. RD 73-17, A.E. Staley Mfg. Co. (Apr. 1973).

METHOD OF PREPARING REDUCED FAT FOODS

CROSS-REFERENCE TO RELATED APPLICATION

This application is a division of pending U.S. Ser. No. 07/578,994, filed Sep. 6, 1990, which is a continuation-in-part of pending U.S. Ser. No. 07/483,208, filed Feb. 20, 1990, now abandoned.

FIELD OF THE INVENTION

This invention relates to food formulations in which at least a portion of the fat and/or oil is replaced by a carbohydrate.

BACKGROUND OF THE INVENTION

U.S. Pat. No. 4,510,166 (Lenchin et al.) discloses converted starches having a DE less than 5 and certain paste and gel characteristics which are used as a fat and/or oil replacement in various foods, including ice cream and mayonnaise. The converted starches are described as dextrins, acid-converted starches (fluidity starches), enzyme-converted starches and oxidized starches. It is also disclosed that if the converted starches are not rendered cold-water soluble by the conversion, they are pregelatinized prior to use or cooked during use.

A product bulletin entitled "Paselli SA2; The Natural Alternative to Fats and Oils" (Avebe b.a., Foxhol, Holland, Ref. No. 05.12.31.167 EF) discloses the use of a low-DE-hydrolysate (DE less than 3) made from potato starch as a replacement for fifty percent of the fat with an amount of the low-DE-potato starch hydrolysate plus water (starch hydrolysate at 28% dry solids) equal to the amount of fat replaced.

U.S. Pat. Nos. 3,962,465 (Richter et al.) and 3,986,890 (Richter et al.) disclose the use of thermoreversible gels of a starch hydrolysate (formed by enzymatic hydrolysis) as a substitute for fat in a variety of foods, including cake creams and fillings, mayonnaise and remoulades, cream cheeses and other cheese preparations, bread spreads, pastes, meat and sausage products, and whipped cream.

The preparation of ready-to-spread frostings having reduced levels of calories is disclosed in U.S. Pat. No. 4,761,292 (Augustine et al.). The patent discloses a frosting which contains (a) about 40 to 85 weight percent sugar, at least about 20 weight percent of which comprises fructose; (b) about 1 to 12 weight percent of a granular starch having a cold-water solubility of greater than 50 weight percent and a fat content of less than 0.25 weight percent; (c) about 5 to 30 weight percent fat; and (d) about 10 to 30 weight percent water. The patent also discloses, at column 5, lines 25-38, that the preferred frostings contain 8 to 18 weight percent fat in comparison to conventional frostings which routinely contain about 18 to 30 weight percent fat.

SUMMARY OF THE INVENTION

In one aspect, this invention relates to a food formulation having a reduced level of fat and/or oil comprising a mixture of a foodstuff and a fragmented, amylopectin starch hydrolysate as a replacement for at least a substantial portion of the fat and/or oil of said food formulation, said hydrolysate being capable of forming an aqueous dispersion at about 20% hydrolysate solids exhibiting a yield stress of from about 100 to about 1,500 pascals.

In another aspect, this invention relates to a method of formulating a food containing a fat and/or oil ingredient comprising replacing at least a substantial portion of said fat and/or oil ingredient with a fragmented, amylopectin starch hydrolysate capable of forming an aqueous dispersion at about 20% hydrolysate solids exhibiting a yield stress of from about 100 to about 1,500 pascals.

By "fragmented, amylopectin starch hydrolysate" is meant a starch material comprised of a major proportion of amylopectin which has been subjected to acid hydrolysis followed by mechanical disintegration of the starch into fragments, a majority of which no longer exhibit the characteristic shape of the parent starch granule. The hydrolysis and disintegration will be sufficient to produce a hydrolysate which will form an aqueous dispersion at about 20% hydrolysate solids exhibiting a yield stress of from about 100 to about 1,500 pascals. The hydrolysis and fragmentation are accomplished at temperatures insufficient to gelatinize (or cook) said starch, and thus the fragments are composed predominantly of insoluble starch hydrolysate products.

The terms "foodstuff" and "food", as used herein, are intended to broadly cover nutritional and/or functional materials that are ingested by humans in the course of consuming edible fare. The term "fats and/or oils" is intended to broadly cover edible lipids in general, specifically the fatty triglycerides commonly found in foods. The terms thus include solid fats, plastic shortenings, fluid oils, and the like. Common fatty triglycerides include cottonseed oil, soybean oil, corn oil, peanut oil, canola oil, sesame oil, palm oil, palm kernel oil, menhaden oil, whale oil, lard, and tallow. The technology of fats and/or oils is described generally by T. H. Applewhite, "Fats and Fatty Oils", *Encyclopedia of Chemical Technology*, Vol. 9, pp. 795–831 (Kirk-Othmer, eds., John Wiley & Sons, N.Y., N.Y., 3d ed., 1980), the disclosure of which is incorporated by reference.

The use of the terms "major" and "minor" in context together in this specification is meant to imply that the major component is present in a greater amount by weight than the minor component, and no more nor less should be inferred therefrom unless expressly noted otherwise in context.

I. GRANULAR STARCH METHODS

A. Granular Hydrolysis Method

1. Moderate temperature hydrolysis method

In one aspect, this invention relates to a method of preparing a starch hydrolysate comprising maintaining, for a period greater than 4.5 hours, a strongly acidic aqueous slurry comprised of a granular starch at a temperature greater than 55.5° C. and below both (i) the gelatinization temperature of said granular starch in said slurry and (ii) the atmospheric boiling point of said slurry, to hydrolyse a substantial portion of said granular starch and retain a starch hydrolysate residue insoluble in said strongly acidic aqueous slurry.

"Insoluble in said strongly acidic aqueous slurry" means that solid starch hydrolysate which is recoverable from the slurry (optionally when neutralized) through isolation from the bulk of the liquid phase by mechanical means, e.g., by decantation, centrifugation, and/or filtration, and as opposed to evaporation of the liquid phase. By "gelatinization temperature" is meant the temperature at which a majority (by weight) of the granular starch starting material is "gelatinized" or "pasted". In other words, a process in which the gelatinization occurs with respect to a minor amount of the granular starch starting material is within the scope of the moderate temperature process, unless otherwise noted.

It is believed that the moderate temperature hydrolysis conditions result in a product having (i) both improved properties, e.g., improved temperature stability after fragmentation (as compared with hydrolysis at a low temperature, e.g., at room temperature as for a Nageli amylodextrin or Lintner starch, see, e.g., W. C. Mussulman and J. A. Wagoner, "Electron Microscopy of Unmodified and Acid-Modified Corn Starches", *Cereal Chemistry*, Vol. 45, pp. 162–171 (1968), the disclosure of which is incorporated by reference) and (ii) improved product yield (as compared with hydrolysis at a high temperature, e.g., at reflux of an aqueous medium).

It has been found that the granular process yields a product having a molecular weight and DP profile (the amount of glucan oligomers of differing degree of polymerization) that is radically different from the product of the process described in U.S. Pat. No. 3,351,489 (Battista).

In preferred embodiments, said maintaining is effective to produce a slurry having a dextrose content of the supernatant phase of said slurry of at least about 0.5% by weight (as is) of the supernatant phase, more preferably from about 1% to about 2.5%, and said slurry is comprised of a strong acid at a concentration of at least about 0.3N (preferably at least about 0.4N) based upon the aqueous phase of said slurry.

2. Integrated process

In another aspect, this invention relates to a method of preparing an insoluble starch hydrolysate and ethanol comprising:

a) maintaining a granular starch in a strongly acidic aqueous slurry at a temperature and for a time sufficient to hydrolyse a substantial portion of said granular starch to soluble saccharides and retain a starch hydrolysate residue insoluble in said strongly acidic aqueous slurry;

b) neutralizing said strongly acidic aqueous slurry to a substantially neutral pH;

c) separating said starch hydrolysate residue from the aqueous phase of said slurry;

d) contacting the aqueous phase of said slurry with glucoamylase to produce dextrose from at least a substantial portion of said soluble saccharides; and e) fermenting said dextrose to produce ethanol.

The above method typically comprises removing, prior to said fermenting, a substantial portion of the salt in said aqueous phase resulting from said neutralizing and said removing may be comprised of (i) passing the aqueous phase through a membrane which retains at least a substantial portion of said soluble saccharides, but allows a majority of the salt to permeate said membrane or (ii) electrodialysis of said portion of said salt.

In preferred embodiments of this method, said time of maintaining is for a period greater than 4.5 hours and said temperature is above 55.5° C. and below both (i) the gelatinization temperature of said granular starch in said slurry and (ii) the atmospheric boiling point of said slurry and said strong acidic aqueous slurry is comprised of hydrochloric acid at a concentration of at least about 0.3N based on the liquid of said slurry.

B. Separation Processes

1. Separation by centrifugation

In another aspect, this invention relates to a method of separating a granular starch hydrolysate residue from a liquid phase, the granules of said granular starch hydrolysate residue being susceptible to physical fragmentation, comprising:

introducing a slurry of said granular starch hydrolysate residue into an imperforate bowl, batch centrifuge;

operating said centrifuge at a sufficiently high velocity to sediment at least a majority, by weight, of said granular starch hydrolysate residue from said liquid phase, wherein any shear of said granular starch hydrolysate during said introducing and said operating is insufficient to physically fragment a substantial portion, by weight, of said granular starch hydrolysate residue; recovering said granular starch hydrolysate residue from said bowl; and drying said granular starch hydrolysate to a microbiologically stable moisture content.

By "sufficiently high velocity" is meant an acceleration sufficient to sediment at least a majority (by weight) of the granular starch hydrolysate residue, but insufficient to generate (in conjunction with the modes of introduction and exit of materials from the centrifuge) shear within the hydrolysate that will physically fragment a substantial portion by weight of the granular starch hydrolysate residue. By "substantial portion" is meant, in this context, a portion sufficient to impart to a slurry a viscosity which prevents sedimentation by said centrifuge of the majority by weight of said insoluble starch hydrolysate residue. In general, the acceleration provided by the centrifuge will be less than about 10,000 times gravity (g-force), typically less than 5,000 g and most typically from about 1,300 to about 3,000 g.

In a related aspect, this invention relates to a method of separating a granular starch hydrolysate residue from a liquid phase, the granules of said granular starch hydrolysate residue being susceptible to physical fragmentation, comprising introducing said slurry into a hollow cylinder, said cylinder having (i) a first flange extending from a first rim at a first end of said cylinder transverse to the axis of said cylinder to form a first interior lip at said first end of said cylinder, the edge of said first flange away from said first rim forming a first substantially circular opening in said first end of said cylinder, and (ii) a second flange extending from a second rim at a second end of said cylinder transverse to said axis to form a second interior lip at said second end of said cylinder, the edge of said second flange away from said second rim forming a second substantially circular opening in said second end of said cylinder, said second substantially circular opening being smaller than said first substantially circular opening, said introducing being effective to place said slurry in contact with the interior of said cylinder at a point proximate to said second flange; and rotating said cylinder about its axis to (i) sediment at least a portion of the insoluble starch hydrolysate residue of said slurry as a cake confined between said first and second flanges and (ii) form an aqueous liquid phase depleted of the majority of said insoluble starch hydrolysate residue;

passing at least a portion of said aqueous liquid phase through said first substantially circular opening opening; then passing said cake of insoluble starch hydrolysate residue through said second substantially circular opening; and drying said cake of insoluble starch hydrolysate residue to a microbiologically stable moisture content.

The principles and modes of operation of imperforate bowl centrifuges are described by A. C. Lavanchy and F. W. Keith, "Centrifugal Separation", *Encyclopedia of Chemical Technology*, Vol. 5, pp. 194–233 (Kirk-Othmer, eds., John Wiley & Sons, N.Y., N.Y., 3d ed., 1979) and P. A. Schweitzer, *Handbook of Separation Techniques for Chemical Engineers*, pp. 4-60 to 4-88 (McGraw Hill, N.Y., N.Y., 1988), the disclosures of each of which are incorporated herein. (It should be noted that Schweitzer uses the term "Solid-Wall Basket Centrifuge".)

FIG. 1 shows a plane extending through the center of the bowl of an imperforate bowl centrifuge as though the bowl were cut in half through the center. The bowl can be thought of as a hollow cylinder with wall 1. Flange 2 extends perpendicularly from wall 1 to form a lip at the first end of the hollow cylinder and flange 3 extends similarly from wall 1 to form a lip at the other (bottom) end of the hollow cylinder. Flange 3 is broader than flange 2 so that the opening at the bottom of the cylinder is narrower, thus as a liquid level rises from wall 1, liquid will pass over flange 2 before reaching the edge of flange 3. FIG. 1 also shows conduit 4 having outlet 5 proximate to flange 3. When slurry is introduced through conduit 4 and the cylinder is rotated at sufficient velocity about its axis of symmetry, insoluble starch hydrolysate residue will sediment as a cake, first proximate to wall 1 and then extending outward from wall 1. Aqueous liquid depleted of insoluble starch hydrolysate residue will collect and overflow the cylinder over flange 2 in the direction shown by arrow 7. Housing 8 confines the aqueous liquid within the centrifuge for collection. At the end of a batch, introduction of slurry is stopped and the cake is removed (typically by ploughing from the wall) through the smaller opening in the cylinder formed by flange 3. It is thought that a continuous solid bowl centrifuge performs isolation of the insoluble starch hydrolysate residue poorly because the agitation of the cake by continuous removal interrupts the laminar flow of the aqueous liquid and, thus, fragments and/or resuspends a significant portion of the cake.

2. Separation by macrofiltration with organic solvent

In another aspect, this invention relates to a method of separating a granular starch hydrolysate residue from a slurry with an aqueous liquid phase, the granules of said granular starch hydrolysate residue being susceptible to physical fragmentation, comprising:

diluting said aqueous liquid phase with a water-miscible organic solvent to form a macrofilterable aqueous-organic slurry;

macrofiltering said macrofilterable aqueous-organic slurry to collect a granular starch hydrolysate residue as a filter cake; and desolventizing (e.g., by drying) said filter cake to produce an edible granular starch hydrolysate.

By "water-miscible organic solvent" is meant a solvent which will mix with water to form an aqueous/organic phase containing a major amount (by weight) of such organic solvent. Selection of a precise organic solvent to water ratio will depend on the precise centrifugation and efficiency of the filtration equipment used. In general, the weight ratio should exceed 60 to 40, alcohol to water. The organic solvent should be a food grade material, i.e., the residue, if any, of such solvent, after drying of the solid material collected by filtration, should be edible, i.e., fit for human consumption. Examples of suitable solvents include the lower alkanols (e.g., ethanol, isopropanol and mixtures thereof); lower aliphatic esters (e.g., ethyl acetate); lower aliphatic ketones (e.g., acetone); and glycols (e.g., 1,3-butylene glycol).

3. Separation by microfiltration

In another aspect, this invention relates to a method of separating a granular starch hydrolysate residue from the liquid phase of a slurry, the granules of said granular starch hydrolysate being susceptible to physical fragmentation, comprising:

exerting pressure on said slurry while said slurry is in contact with a microporous ceramic membrane;

passing a permeate solution containing a dissolved member selected from the group consisting of a strong acid, a salt thereof, and mixtures thereof, said permeate solution being substantially free of insoluble starch hydrolysate residue, through said microporous ceramic membrane;

collecting said granular starch hydrolysate residue as a retentate; and drying said granular starch hydrolysate residue to a microbiologically stable moisture content.

By "microporous ceramic membrane" is meant any ceramic layer (including "supported layer articles") having micropores and sufficient structural integrity to withstand the pressure needed to isolate the insoluble starch hydrolysate residue from the liquid phase of the aqueous slurry over a desired period of time (e.g., from 15 minutes to 24 hours). It is believed that the high pressure used to isolate the insoluble starch hydrolysate residue creates turbulent flow at the membrane's surface which prevents small particles in the slurry from "blinding off" the pores of the membrane (as has been observed with conventional filtration equipment as discussed below).

A typical microporous ceramic membrane is comprised of a microporous ceramic article having at least one macroscopic passage therethrough (typically a cylindrical article having cylindrical passages) substantially parallel to the axis of symmetry of the cylindrical article. While the article may be "microporous" itself, the ceramic cylinder may act principally as a support (i.e., in a "supported layer article") for a microporous layer (or layers with regard to multi-passage articles) which covers the surfaces defined by the passages through the ceramic article. The porosity of the ceramic article, and any microporous layer associated therewith as described above, can be varied as desired, with the pore size of any such layer being smaller than that of the article. In typical operation, such a ceramic filter element (i.e., cylindrical and microporous ceramic article) is contained in hollow cylindrical housing and slurry is fed into the passages under pressure through a feed manifold that prevents leakage into the housing. The exit of the isolated starch hydrolysate residue from the passages at the other end of the ceramic filter element is controlled by an exit manifold which also prevents leakage into the housing where the filtrate or permeate is contained. Ceramic filter elements and their use are described in "Solve Tough Process Filtration Problems with Ceraflo Ceramic Systems", a technical bulletin, Lit. No. SD113, 2/89 89-418, published (1989) by Millipore Corporation, Bedford, Mass., the disclosure of which is incorporated by reference.

It has been found that microfiltration is an effective means of separating an insoluble starch hydrolysate residue from an aqueous slurry thereof which also contains a relatively large amount of dissolved species, e.g., salt and saccharides. Microfiltration is described generally in D. R. Paul and C. Morel, "Membrane Technology", *Encyclopedia of Chemical Technology*, Vol. 15, pp. 92-131 (Kirk-Othmer, eds., John Wiley & Sons, N.Y., N.Y., 3d ed., 1981), the disclosure of which is incorporated herein by reference.

Typically, a liquid including small dissolved molecules is forced through a porous membrane. Large dissolved molecules, colloids and suspended solids that cannot pass through the pores are retained. Components retained by the membrane are collectively referred to as a concentrate or retentate. Components which traverse the membrane are referred to collectively as filtrate or permeate. Diafiltration is a microfiltration process in which the retentate is further purified or the permeable solids are extracted further by the addition of water to the retentate. This process is analagous to washing of a conventional filter cake. The use of microfiltration removes salts formed by the neutralization of the alkaline solution and other small molecular species.

Ultrafiltration is generally described and discussed by P. R. Klinkowski, "Ultrafiltration", *Encyclopedia of Chemical Technology*, Vol. 23, pp. 439-461 (Kirk-Othmer, eds., John Wiley & Sons, N.Y., N.Y., 3d ed., 1983), the disclosure of which is incorporated by reference herein. Ultrafiltration is a pressure-driven filtration on a molecular scale. The porous membrane typically has a pore size ranging from 0.005 to 20 micrometers (or microns). While a distinction is often made in the separation art between ultrafiltration (pore size range of 2 to 20 nanometers) and microfiltration (pore size greater than 20 nanometers), the terms will be used interchangeably herein unless expressly noted otherwise.

II. DRY GRANULAR STARCH HYDROLYSATE COMPOSITIONS

A. Granular Starch Hydrolysate

In another aspect, this invention relates to a dry granular starch hydrolysate composition consisting essentially of a major amount by weight of cold-water insoluble hydrolysate and a minor amount by weight of cold-water soluble hydrolysate, said dry, granular starch hydrolysate having (a) weight average molecular weight of from about 4,000 g/mol to about 7,500 g/mol, (b) a bland organoleptic character, and (c) an essentially dry moisture content.

It has been found that the granular starch hydrolysis process results in a granular starch hydrolysate composition that is particularly advantageous because of (i) the relative amounts of hydrolysate insolubles and hydrolysate solubles, (ii) weight average molecular weight, (iii) the bland organoleptic character of the granular starch hydrolysate, and (iv) edibility. This combination of properties is important to the use of the hydrolysate as a food ingredient, especially as a fat mimicking ingredient in foods. An essentially dry moisture content is important with respect to the edibility of the composition, e.g., the ability to handle and process the composition into a food product and the microbiological stability of the composition on storage thereof. The composition consists essentially of the major and minor amounts of hydrolysates of different solubility in the sense that it is essentially free of organic solvents and reaction products thereof with hydrolysate components (e.g., ethanol and ethyl glucosides).

B. Granular Starch Hydrolysate and Salt or Saccharide

1. Granular starch hydrolysate and salt

In another aspect, this invention relates to an essentially dry composition of matter comprising (i) a major amount by weight of a granular starch hydrolysate, said granular starch hydrolysate having a weight average molecular weight of less than about 12,000 g/mol and being comprised of a major amount by weight of cold-water insoluble hydrolysate and a minor amount by weight of a cold-water soluble hydrolysate, and (ii) a minor amount of salt selected from the group consisting of alkali metal chlorides, alkali metal sulfates, alkaline earth metal chlorides, alkaline earth metal sulfates, and mixtures of two or more thereof, said salt being present in an amount sufficient to produce an organoleptically fat-like aqueous dispersion upon fragmentation of said composition in an essentially aqueous medium at about 20% dry solids of said starch hydrolysate. Typically, said salt is present in an amount of at least 0.1% basis dry weight of said granular starch hydrolysate, preferably at least about 1%, and more preferably about 1% to about 3%.

In another aspect, this invention relates to a composition of matter comprising:

a major amount by weight of a granular starch hydrolysate having a weight average molecular weight of less than about 12,000 g/mol and being comprised of:
a controlled amount of salt present in an amount sufficient to enhance the fat-like characteristics of the composition upon shearing in an aqueous medium, said salt selected from the group consisting of alkali metal chlorides, alkali metal sulfates, alkaline earth metal chlorides, alkaline earth metal sulfates, and mixtures thereof.

2. Granular starch hydrolysate and saccharide

In another aspect, this invention relates to a composition of matter comprising (i) a major amount by weight of a granular starch hydrolysate, said granular starch hydrolysate having a weight average molecular weight of less than about 12,000 g/mol and being comprised of a major amount by weight of cold-water insoluble hydrolysate and a minor amount by weight of cold-water soluble hydrolysate, and (ii) a carbohydrate saccharide (in addition to said cold-water soluble hydrolysate) in an amount effective (e.g., a comparable amount by weight, see below) in relation to the amount of said fragmented granular starch hydrolysate and said water to enhance the fat-like properties of said dispersion following either freezing or heating to a temperature of about 72° C.

III. GRANULAR FRAGMENTING METHOD

In another aspect, this invention relates to a method of making a composition of matter useful in replacing fat and/or oil in a food formulation comprising physically fragmenting a minor amount of a granular starch hydrolysate in a major amount of an aqueous liquid, said hydrolysate being comprised of a major amount of cold-water insoluble hydrolysate and a minor amount of cold-water soluble hydrolysate.

It has been found that saccharide sweeteners inhibit the formation of a fat-like salve or creme in a propeller type of fragmentation device (e.g., a Waring blender), but that a device which employs impinging streams to fragment (e.g., a MICROFLUIDIZER) avoids such inhibition. Further, it has been found that devices which fragment by forcing a slurry through a restricted orifice, e.g., a homogenizer, may tend to plug, but that the addition of an emulsifier to the slurry will inhibit such plugging.

Homogenizers useful in forming suspensions or emulsions are described generally by H. Reuter, "Homogenization", *Encyclopedia of Food Science*, pp. 374–376, (M. S. Peterson and A. H. Johnson, eds., AVI Publ. Co., Westport, Conn., 1978), L. H. Rees and W. D. Pandolfe, "Homogenizers", *Encyclopedia of Food Engineering*, pp. 467–472 (C. W. Hall et al., eds., AVI Publ. Co., Westport, Conn., 1986), and W. C. Griffin, "Emulsions", *Encyclopedia of Chemical Technology*, Vol. 8, pp. 900–930 (Kirk-Othmer eds., John Wiley & Sons, N.Y., N.Y., 3d ed., 1979), the disclosures of which are incorporated herein by reference.

IV. FRAGMENTED GRANULAR DISPERSION

A. Aqueous Dispersion of Fragmented Granules

In another aspect, this invention relates to an aqueous dispersion useful as a replacement for fats and/or oils comprising a major amount by weight of water and a minor amount by weight of a fragmented granular starch hydrolysate, said fragmented granular starch hydrolysate being (i) comprised of a major amount by weight of cold-water insoluble hydrolysate material and a minor amount by weight of cold-water soluble hydrolysate material and (ii) capable of imparting to said dispersion at about 20% solids a yield stress of from about 100 to about 1,500 pascals.

It is believed that the cold-water soluble hydrolysate material improves the water immobilization capability of such cold-water insoluble hydrolysate material, as compared to aqueous dispersion containing only cold-water insoluble material at the same level of cold-water insoluble material solids. In general, the "minor amount" will be a significant amount in terms of its effect on the properties of the composition, e.g., the ratio of cold-water insoluble to cold-water soluble will be no greater than about 9:1, typically less than about 5:1, and preferably from about 3.0:1 to about 4.0:1.

B. Aqueous Dispersion and Salt

In another aspect, this invention relates to an aqueous dispersion comprising (i) a minor amount by weight of a fragmented granular starch hydrolysate, said fragmented granular starch hydrolysate being comprised of a major amount by weight of a cold-water insoluble hydrolysate and a minor amount by weight of cold-water soluble hydrolysate, (ii) a major amount by weight of water, and (iii) a minor amount of salt selected from the group consisting of alkali metal chlorides, alkali metal sulfates, alkaline earth metal chlorides, alkaline earth metal sulfates, and mixtures of two or more thereof, said salt being present in an amount sufficient to produce an organoleptically fat-like aqueous dispersion.

C. Aqueous Dispersion and Saccharide

In another aspect, this invention relates to an aqueous dispersion comprising (i) a minor amount by weight of a fragmented granular starch hydrolysate, said fragmented granular starch hydrolysate being comprised of a major amount by weight of a cold-water insoluble hydrolysate and a minor amount by weight of cold-water soluble hydrolysate, (ii) a major amount by weight of water, and (iii) a carbohydrate saccharide in an amount effective in relation to the amount of said fragmented granular starch hydrolysate and said water to enhance the fat-like properties of said dispersion following either freezing or heating to a temperature of about 72° C.

D. Aqueous Dispersion and Emulsifier

In another aspect, this invention relates to an aqueous dispersion comprising:
 a minor amount of a fragmented granular starch hydrolysate comprised of a major amount by weight of cold-water insoluble hydrolysate and a minor amount by weight of cold-water soluble hydrolysate;
 a major amount by weight of water; and
 a food grade emulsifier present in an amount (e.g., a minor amount in relation to the starch hydrolysate, for example, 75:1 to about 2:1 starch hydrolysate dry solids to emulsifier) sufficient to enhance the fat-like properties of said dispersion following heating of said dispersion to a temperature of about 72° C.

E. Method of Pasteurizing

In another aspect, this invention relates to a method of pasteurizing an aqueous dispersion comprising:
 combining a fragmented granular starch hydrolysate comprised of a major amount by weight of a cold-water insoluble hydrolysate and a minor amount by weight of cold-water soluble hydrolysate, in said aqueous dispersion with a protective agent selected from the group consisting of a carbohydrate saccharide (as defined herein), an emulsifier, and mixtures thereof; and
 heating said aqueous dispersion to a temperature of at least about 72° C. for a time sufficient to pasteurize said aqueous dispersion, wherein the amount of said protective agent is sufficient, in relation to said temperature and said time, to produce an organoleptically fat-like aqueous dispersion.

Pasteurization is described generally by C. M. Trout, "Pasteurization", *Encyclopedia of Food Science*, pp. 600–604 (M. S. Peterson and A. H. Johnson, eds., AVI Publ. Co., Westport, Conn., 1978), the disclosure of which is incorporated by reference. In general, high-temperature, short-time (HTST) techniques involve heating a composition to about 85° C. for about 1 sec., but dairy products, e.g., milk, are typically held at 71.1° C. for 15 sec. Trout, supra, at p. 602, recommends a sliding scale for near ultrahigh temperature pasteurization in which the time of hold, e.g., 1.00 sec. at 88.3° C., is reduced as the pasteurization temperature is increased, e.g., 0.01 sec. at 100.0° C.

V. GRANULAR AMYLOPECTIN FOOD COMPOSITION AND METHOD

A. Foodstuff and Fragmented Granular Amylopectin Starch Hydrolysate

In another aspect, this invention relates to a composition of matter comprising a foodstuff, a major amount of an aqueous liquid and a minor amount of a fragmented granular, amylopectin starch hydrolysate dispersed in said aqueous liquid, said hydrolysate being comprised of a major amount of cold-water insoluble hydrolysate and a minor amount of cold-water soluble hydrolysate.

It is believed that the cold-water soluble hydrolysate material improves both the high-temperature stability of the cold-water insoluble hydrolysate material in the aqueous dispersion and the water immobilization capability of such cold-water insoluble hydrolysate material, as compared to aqueous dispersion containing only cold-water insoluble material at the same level of cold-water insoluble material solids. As an amylopectin based material, the fragmented granular starch hydrolysate will exhibit a bimaximal profile of oligomers of varying degree of polymerization with (i) a maximum in proximity to a degree of polymerization of about 13, and (ii) a maximum in proximity to a degree of polymerization of about 26. (A profile of the oligomeric composition of a starch hydrolysate (the "oligomer profile") can be obtained by the method described by K. Koizumi, et al., "High-Performance Anion-Exchange Chromatography of Homogeneous D-Gluco-Oligosaccharides and -Polysaccharides (Polymerization Degree equal to or greater than 50) With Pulsed Amperometric Detection", *Journal of Chromatography*, 46, pp. 365–373 (1989), the disclosure of which is incorporated by reference herein.)

B. Method of Replacing Fat and/or Oil

In another aspect, this invention relates to a method of formulating a food containing a fat and/or oil ingredient comprising replacing at least a substantial portion of said fat and/or oil ingredient with a fragmented granular, amylopectin starch hydrolysate, said hydrolysate being comprised of a major amount of cold-water insoluble hydrolysate and a minor amount of cold-water soluble hydrolysate.

C. Foodstuff Having Reduced Fat and/or Oil

In a related aspect, this invention relates to a food formulation having a reduced level of fat and/or oil comprising a mixture of a foodstuff and a fragmented granular, amylopectin starch hydrolysate, said hydrolysate being comprised of a major amount of cold-water insoluble hydrolysate and a minor amount of cold-water soluble hydrolysate, as a replacement for at least a substantial portion of the fat and/or oil of said food formulation.

VI. GRANULAR AMYLOSE TO REPLACE FAT IN FOOD FORMULATIONS

A. Method of Replacing Fat and/or Oil

In another aspect, this invention relates to a method of formulating a food containing a fat and/or oil ingredient comprising replacing at least a substantial portion of said fat and/or oil ingredient with a fragmented granular, amylose starch hydrolysate, said hydrolysate being comprised of a major amount of cold-water insoluble hydrolysate and a minor amount of cold-water soluble hydrolysate.

It is believed that the cold-water soluble hydrolysate material improves water immobilization capability of such cold-water insoluble hydrolysate material, as compared to aqueous dispersion containing only cold-water insoluble material at the same level of cold-water insoluble material solids. In general, the "minor amount" will be a significant amount in terms of its effect on the properties of the composition, e.g., the ratio of cold-water insoluble to cold-water soluble will be no greater than about 9:1, typically less than about 5:1, and preferably from about 3.0:1 to about 4.0:1.

B. Foodstuff Having Reduced Fat and/or Oil

In a related aspect, this invention relates to a food formulation having a reduced level of fat and/or oil comprising a mixture of a foodstuff and a fragmented granular, amylose starch hydrolysate, said hydrolysate being comprised of a major amount of cold-water insoluble hydrolysate and a minor amount of cold-water soluble hydrolysate, as a replacement for at least a substantial portion of the fat and/or oil of said food formulation.

VII. FRAGMENTED GRANULAR STARCH HYDROLYSATE DISPERSION IN COMBINATION WITH MEDIUM UNSATURATED OIL

In another aspect, this invention relates to a composition of matter comprising a macroscopically homogeneous blend of (i) an aqueous dispersion of fragmented granular starch hydrolysate and (ii) a medium-unsaturated oil, wherein the amount of said aqueous dispersion of fragmented granular starch hydrolysate is sufficient in relation to the amount of medium-unsaturated oil to impart plasticity to said composition.

By "medium-unsaturated oil" is meant an oil which consists essentially of tri-glycerides of mono-unsaturated fatty acids (e.g., oleic acid) and di-unsaturated fatty acids (e.g., linoleic acid) and, thus is liquid at room temperature. Examples include oleic-/linoleic oils (e.g., corn oil and safflower); erucic acid oils (e.g., canola oil); and linolenic acid oils (e.g., soybean oil). These oil types are described by Applewhite, "Fats and Fatty Oils", above and may have been stabilized against oxidative degradation, e.g., with antioxidants and/or hydrogenation to lower the level of linolenates) and/or solid phase precipitation (e.g., by winterizing). Low temperature and trans-suppressive hydrogenation is discussed by H. B. W. Patterson, *Hydrogenation of Fats and Oils*, pp. 44–48, 173–182, 291–304 (Applied Science Publishers, N.Y., N.Y., 1983), and the references cited therein, the disclosures of which are incorporated herein by reference.

VIII. LAYERED PASTRY ARTICLE AND METHOD

In another aspect, this invention relates to a method of preparing a pastry comprising applying an aqueous dispersion comprised of a fragmented granular starch hydrolysate to a plurality of layers of dough, assembling said layers into a pastry dough article, and baking said article and typically said aqueous dispersion is further comprised of a carbohydrate saccharide (in addition to the fragmented granular starch hydrolysate) in a comparable amount (with respect to the hydrolysate) by weight (e.g., in a ratio of from about 4:1 to 1:4, preferably 2:1 to 1:2 (by weight), carbohydrate saccharide to starch hydrolysate).

In a related aspect, this invention relates to a layered pastry article comprising a plurality of layers of baked dough in contact with a fragmented granular starch hydrolysate in an amount sufficient to retard the staling of said layered pastry article.

As discussed more fully below, the use of a fragmented granular starch hydrolysate in a layered pastry article is particularly advantageous, especially with respect to the organoleptic properties of the finished pastry. Staling of baked foods is discussed in U.S. Pat. No. 4,291,065 (Zobel et al.), the disclosure of which is incorporated by reference.

DETAILED DESCRIPTION OF THE INVENTION

Figure 1:
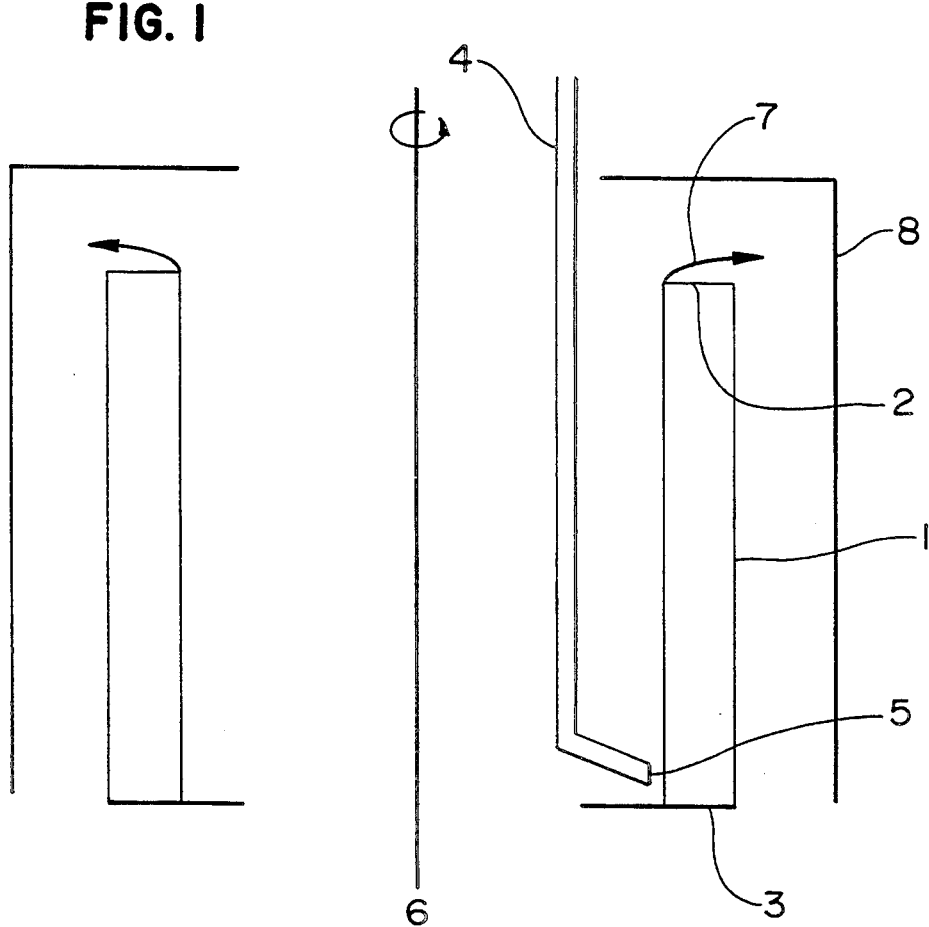
FIG. 1 is a plane view of a bowl from a solid bowl, batch centrifuge.

The fragmented, amylopectin starch hydrolysate is made by the sequential acid-hydrolysis and fragmentation of a granular amylopectin starch material. Starch is generally comprised of a highly-branched glucan having alpha-1,4 and alpha-1,6 linkages, denominated amylopectin, and a substantially linear glucan, having almost exclusively alpha-1,4 linkages, denominated amylose. Methods of determining the amounts of each are referenced in R. L. Whistler et al., *Starch: Chemistry and Technology*, pp. 25–35 (Academic Press, Inc., New York, N.Y. 1984), the disclosure of which is incorporated by reference. Examples of starches having a major proportion of amylopectin include the common non-mutant starches of cereals and legumes, e.g., corn, wheat, rice, potato and tapioca, and mutant varieties comprised of a major proportion of amylopectin, e.g., waxy maize. Preferred for use herein are common corn starch and waxy maize starch.

As used herein, the term "granular starch" refers to a starch composition in which the native granular structure is retained. Thus, this term, without further limitations, includes common starches and starches isolated from mutant varieties, e.g., waxy maize starch and high amylose corn starch. High amylose corn starch is commercially available in native granular form and having an amylose content within the range of about 50% to about 80%. For example, native granular starches, one with an amylose content of 55% to 60% and the other with about 70%, are available from National Starch and Chemical Corporation, Bridgewater, N.J., HYLON TM and HYLON VII, respectively. The starch should be in the native granular form to be useful as a starting material. This form is resistant to hydration and/or gelatinization during the acid-hydrolysis, and thus, fragments of the starch will retain many of the structural features of the native granule, e.g., the lamellae resulting from the growth pattern of the granule. Various pretreatments of the native granule starting material can be performed so long as the resistance to gelatinization during acid-hydrolysis is preserved. A particularly useful pretreatment is defatting of the granule, e.g., by an alkaline wash as described in U.S. Pat. No. 4,477,480 (Seidel et al.), the disclosure of which is incorporated herein by reference, and/or a solvent extraction as described in U.S. Pat. Nos. 3,717,475 and 3,586,536 (Germino), the disclosures of which are incorporated by reference. The granular starch from which the hydrolysate is made should generally contain less than about 1.5% fatty acids and proteins. Because the hydrolysis is accomplished in a predominantly aqueous medium and is typically washed with only water, the hydrolysis will not remove any substantial portion of the lipids present in the starch. Further, because a substantial portion of the starch is hydrolyzed to products soluble in the aqueous medium and subsequent wash water, the hydrolysis and washing will remove starch solids and, thus, result in a lipid content on a weight percentage basis that is higher for the hydrolysate than the parent starch.

The acid-hydrolysis of the granular starch is performed to permit mechanical disintegration of the granular starch hydrolysate residue to a degree that will allow the formation of an aqueous dispersion that is salve-like. The hydrolysate will be capable upon mechanical disintegration of forming an aqueous dispersion (at about 20% hydrolysate solids) having a yield stress of from about 100 to about 1,500 pascals (for example, from about 200 to about 800 pascals or from about 200 to about 600 pascals), but more preferably from about 400 to about 1,500 pascals, and most preferably at least about 500 pascals.

The yield stress of an aqueous dispersion of fragmented starch hydrolysate has been found to correlate well with the fat-like consistency of the aqueous dispersion. In other words, if the yield stress is in an appropriate range, the aqueous dispersion will generally exhibit a fat-like consistency. However, yield stress may not correlate well with properties other than consistency. For example, a sample with an appropriate yield stress may exhibit a gritty mouthfeel (i.e., grittiness) due to aggregation of the insoluble hydrolysate particles (e.g., as a result of freeze-thaw of an aqueous dispersion of fragmented starch hydrolysate). Further, the correlation between yield stress and fat-like consistency may not hold in the converse for all fragmented starch hydrolysates described herein. In other words, a particular fragmented starch hydrolysate may exhibit a fat-like consistency under some conditions, but not exhibit an appropriate yield stress. In sum, while yield stress exhibits a useful correlation with fat-like consistency, yield stress is not believed to be a perfect predictor of fat mimicking properties of a fragmented starch hydrolysate.

In general, the starch hydrolysate will have a peak molecular weight as measured by gel permeation chromatography of from about 2,000 g/mol to about 10,000 g/mol, preferably from about 3,500 g/mol to about 5,000 g/mol and more preferably from about 4,500 g/mol to about 5,000 g/mol.

It has been found that the weight average molecular weight ($M_w$) as measured by gel permeation chromatography exhibits a better correlation (better than PMW) to the yield stress of an aqueous dispersion of the fragmented starch hydrolysate. The $M_w$ should generally range from about 3,000 to about 12,000, preferably about 4,000 to about 7,500 and more preferably 4,500 to about 6,500. (Of course, $M_w$ also correlates to peak molecular weight, but some factors (e.g., the efficiency of washing of the product centrifuge cake which can affect the cold-water solubles content of the product) can affect the degree of correlation between $M_w$ and peak molecular weight from lot to lot of a given production run. Molecular weights of starch hydrolysates can be measured by the procedure described by J. Bouchard et al., "High-Performance Liquid Chromatographic Monitoring of Carbohydrate Fractions in Partially Hydrolyzed Corn Starch", *J. Agric. Food Chem.*, Vol. 36, pp. 1188-1192 (1988), the disclosure of which is incorporated herein by reference.

The Dextrose Equivalent (by Lane-Eynon method DE) of the starch hydrolysate will vary based on the precise degree of hydrolysis and the efficiency of the washing of the starch hydrolysate, but will typically be greater than about 3, more typically greater than about 5, e.g., from about 5.0 to 7.0.

The starch hydrolysates, and fragmented dispersions thereof, can be analyzed by a variety of techniques. For example, low angle (or "small angle") X-ray scattering experiments can be performed on an aqueous dispersion of a fragmented starch hydrolysate and the results (particularly those in the Perod region of the spectrum) may show an ordering (or lack thereof) in the dispersion in the range of tens to hundreds of angstroms. Such low-angle X-ray scattering techniques are described in F. Reuther, et al., "Structure of Maltodextrin Gels—A Small Angle X-Ray Scattering Study", *Colloid and Polymer Science*, 261, 271-276 (1983), the disclosure of which is incorporated by reference. Further, wide angle X-ray scattering techniques (e.g., those described by S. Nara, et al., "Study on Relative Crystallinity of Moist Potato Starch", *Starke/Starch*, Vol. 30, pp. 111-114 (1978)) can be performed on the starting starch, the starch hydrolysate powder and on the aqueous dispersion of fragmented starch hydrolysate to examine the effects of hydrolysis and/or fragmentation on the ordering of the starch material in the range of about 1-15 angstroms, i.e., ordering related to the distances between atoms in the starch material.

Nuclear magnetic resonance techniques (e.g., those described by S. Richardson, "Molecular Mobilities of Instant Starch Gels Determined by Oxygen-17 and Carbon-13 Nuclear Magnetic Resonance", *Journal of Food Science*, Vol. 53, No. 4, pp. 1175-1180 (1988)) can be used to show the electronic environment of atomic nuclei in the starch hydrolysate, e.g., $C^{13}$ and thus give information relating to molecular structure and disposition (e.g., carbohydrate ring conformations, Vander Waals bonding, etc.). The technique of measuring water mobility (or immobility, its inverse) by oxygen-17 NMR may be supplemented with Raman infra-red spectroscopy techniques in the "water-band" of the infra-red portion of the spectrum (e.g., techniques such as those described by C. Lun, et al., "Model Structure for Liquid Water", *Travaux de la Societe de Pharmacie de Montpellier*, Vol. 41, No. 3, pp. 203-212 (1981), the disclosure of which is incorporated herein by reference). Differential Scanning Calorimetry (DSC) can be employed to examine the solubility of the starch hydrolysate in water (before and/or after fragmentation) over various temperatures. Such DSC techniques are described, for example, by D. C. White and G. N. Lauer, "Predicting Gelatinization Temperatures of Starch/Sweetener Systems for Cake Formulation by Differential Scanning Calorimetry. I. Development of a Model", *Cereal Foods World*, Vol. 35, No. 8, pp. 728-731 (August 1990), the disclosure of which is incorporated by reference.

It should also be noted that the mean particle size of the starch hydrolysate, before and after fragmentation, can be measured by a variety of different means. However, the utility of such information must be considered carefully in view of the considerations noted by C. Orr, "Particle Size Measurement", *Encyclopedia of Chemical Technology*, Vol. 21, pp. 106-131 (Kirk-Othmer, eds., John Wiley & Sons, Inc., N.Y., N.Y., 1983), the disclosure of which is incorporated by reference. With this caveat in mind, it should be mentioned that the mean particle size, as measured by certain techniques, of the starch hydrolysate may appear to be substantially the same, e.g., about 10 microns (by light scattering techniques). However, when the aqueous dispersion of fragmented starch hydrolysate is analyzed to determine the surface area of the fragments, a mean particle size on the order of 50 angstroms to 200 angstroms may be inferred therefrom. Without wishing to be bound by any particular theory, unless otherwise noted, this particle size information suggests that the aqueous dispersion of fragmented starch hydrolysate contains agglomerates of fragments, such agglomerates being on the order of 10 microns in size and being comprised of individual fragments on the order of 50-200 angstroms. Further, it may be theorized that the agglomerates are malleable in the dispersion such that they deform (and perhaps undergo inter-agglomerate exchange of fragments) in a manner that imparts the property of plasticity to the dispersion. This plasticity may then give rise to the fat-like or salve-like consistency of the dispersion. This theory may also account for the fat-like mouth-clearing of the dispersion observed in many foods, e.g., frozen desserts. However, it should again be noted that these theories must be considered as such, unless otherwise expressly noted herein.

The acid hydrolysis can be accomplished in an essentially aqueous slurry of the starch. Typical conditions will include a starch slurry at 30% to 40% starch solids in 0.25N to 2.5N mineral acid (e.g., hydrochloric acid or sulfuric acid) maintained at a temperature of from about 50° C. to about 70° C., preferably from about 55° C. to about 60° C., more preferably from about 57° C. to about 62° C., for from about 8 to about 20 hours, preferably from about 10 to about 16 hours, when the acid is about 1N (and from about 8 to about 48 hours, preferably from about 20 to about 30 hours when the acid is about 0.5N). Variations within and around the scope of these parameters to optimize a particular set of conditions in conjunction with the means and degree of mechanical disintegration described below will be within the skill of the art given the examples set forth below.

It is believed that the moderate temperatures employed will reduce the amounts of reversion products produced during hydrolysis. Because reversion products tend to contribute off-flavors to the hydrolysate, minimizing their production should enhance the organoleptic acceptability of the hydrolysate by ensuring the production of a hydrolysate with a desirably bland taste. Likewise, the moderate reaction times will reduce opportunity for the development of rancidity in the hydrolysate that may occur over longer reaction times, e.g., more than a few days, as a result of the breakdown of even small amounts of residual lipids.

The hydrolysis medium is essentially aqueous. Generally, it will contain no more than a trace, if any, of organic solvents (e.g., ethanol). Organic solvents may react with the saccharide by-products (e.g., dextrose to form at least traces of ethyl glucoside), may otherwise affect the hydrolysis reaction (e.g., solvent effects) and/or may contaminate the starch hydrolysate product.

The progress of the hydrolysis may be followed by taking small samples of slurry from an in-progress batch of the starch hydrolysate, adjusting the pH of the slurry (e.g., to 4–5), isolating the solid starch hydrolysate residue from the slurry sample, and mechanically disintegrating the residue under the conditions intended for the batch as a whole. The yield stress of a 20% aqueous dispersion can then be measured to determine if the acid-hydrolysis has progressed to a desired degree. Also, samples of insoluble residue can be isolated for a determination of peak molecular weight (or weight average molecular weight) by gel permeation chromatography or of supernatant for dextrose content (YSI method) and the results used as a measure of the degree of hydrolysis; both molecular weight (particularly $M_w$) and dextrose content have been found to correlate well with yield stress of the resulting starch hydrolysate upon fragmentation, as discussed below.

It has been found that there is very little, if any, change in the degree of branching of the glucan chains of the starch as a result of the acid hydrolysis. Thus, the ratio of 1,4 linkages to 1,6 linkages in the hydrolysate will generally be substantially the same as that of the starting amylopectin starch. Given the typical degree of branching of amylopectin and amylose, a starch comprised of a major proportion of amylopectin (i.e., greater than 50% by weight of the dry solids of the starch is glucan in the form of amylopectin) will exhibit a ratio of alpha-1,4 linkages to alpha-1,6 linkages of less than about 40:1. Thus, the starch hydrolysates will generally have a ratio of alpha-1,4 linkages to alpha-1,6 linkages of less than about 40:1, typically, from about 20:1 to about 40:1.

It has also been found that the crystalline form of the parent starch, as determined by X-ray diffraction, is retained without substantial change, although the relative crystallinity of the starch hydrolysate is generally greater than the parent starch. Thus, native waxy maize and native common corn starch (both of which are substantially free of the "B" type crystalline form) will generally yield hydrolysates that are substantially free of the "B" type as determined by X-ray diffraction.

The starch hydrolysis product of the slurry is isolated as the solid phase residue by separation thereof from the aqueous phase of the slurry. Techniques for such isolation include filtration (e.g., horizontal belt filtering), centrifugation (e.g., disk, decanter or solid bowl), sedimentation, and other suitable dewatering operations. It should be noted, however, as discussed below, that it has been found that a solid bowl centrifuge has been found to be a clearly superior way (i.e., by far the most effective and efficient means) of isolating the solid phase residue by sedimentation. This is discussed more fully below.

It should also be noted that the efficiency of the separation of the insoluble starch hydrolysate residue from the aqueous liquid phase of the hydrolysate slurry and the degree of washing of the residue will affect the relative amounts of cold-water insoluble hydrolysate and cold-water soluble hydrolysate in the residue. However, it appears that the residue is relatively resistant to washing in the sense that relatively large amounts of cold-water solubles remain after washing (by simple reslurrying and recentrifugation at ambient temperatures). Thus, while the washing of the residue will affect the amount of cold-water soluble hydrolysate, conventional washing appears to have a surprisingly small effect.

The acid in the slurry can be neutralized either before or after isolation of the hydrolysate. However, it has been found particularly advantageous (in terms of obtaining a desirably bland flavor for the hydrolysate) to (i) only partially neutralize the slurry to a weakly acidic pH (e.g., from about 2.0 to about 3.5) and (ii) then hold the slurry at a moderately elevated temperature (e.g., 25° C. to 75° C.) for a short period of time (e.g., 15 minutes to 24 hours), prior to isolation, followed by washing and then neutralization of the solid hydrolysate residue to a substantially neutral pH (e.g., about 4.5 to about 5.0). This acid washing of the starch hydrolysate is particularly advantageous when employed in the context of microfiltration of the starch hydrolysate slurry using a ceramic microfiltration membrane contained within an acid resistant (e.g., polyvinyl chloride) housing.

The isolated starch hydrolysate is typically washed and then dried (e.g., to a low moisture content, typically 3–8%) after isolation to allow for handling and storage prior to further processing. Examples of drying techniques include spray drying, flash drying, tray drying, belt drying, and sonic drying. The dried hydrolysate may be hygroscopic, given the presence of the cold-water soluble hydrolysate therein. Thus, some rehydration during handling and storage may occur. Depending upon the precise composition of the hydrolysate and the conditions (including length of time) of storage, steps to maintain the moisture at a low content may be necessary (e.g., moisture barrier packaging and/or control of humidity in the storage environment). If the moisture content is allowed to rise too far (e.g., greater than about 20%, or possibly greater than 15%), bulk handling problems and/or microbiological stability problems might arise.

The fragmented starch hydrolysate may also be otherwise chemically modified. Examples of such chemical modification include the product of reaction with bleaching agents (e.g., hydrogen peroxide, peracetic acid, ammonium persulfate, chlorine (e.g., calcium and/or sodium hypochlorite or sodium chlorite), and permanganate (e.g., potassium permanganate); esterifying agents (e.g., acetic anhydride, adipic anhydride, octenyl succinic anhydrides, succinic anhydride, vinyl acetate); including phosphorous compounds (e.g., monosodium orthophosphate, phosphorous oxychloride, sodium tripolyphosphate, and sodium trimetaphosphate); and/or etherifying agents (e.g., acrolein, epichlorohydrin, and/or propylene oxide). Such chemical modifications will typically be accomplished after the acid hydrolysis step, but may be accomplished prior to the acid hydrolysis or effected by using a modified starch as a starting material for the acid hydrolysis step. Even esterified starches (e.g., starch modified with octenyl succinic anhydride) can be used as a starting material and significant ester functionality will be retained, as demonstrated by example below.

Following acid-hydrolysis (and neutralization of the slurry), the granular starch hydrolysate is subjected to a physical fragmentation as by mechanical disintegration, i.e., fragmented. As used herein, "fragmented" means that a majority of the starch granules have been so fragmented that they no longer exhibit, under microscopic examination, the macro-organization of the granule, e.g., the shape characteristic of that variety of granule. Generally, the concentric shells of material that are observed in the granule after the hydrolysis are not observed in a majority of the granules after fragmentation. However, the native crystallites present in the granule are retained (as confirmed by X-ray diffraction of the salves).

The mechanical disintegration of the hydrolysate may be carried out in several ways, as by subjecting it to attrition in a mill, or to a high speed shearing action, or to the action of high pressures. Disintegration is generally carried out in the presence of a major amount by weight of a liquid medium, preferably water. Although tap water is the preferred liquid medium for the dispersion of fragmented starch hydrolysate, other liquids are suitable provided sufficient water is present to hydrate the fragmented starch hydrolysate and, thus, result in a dispersion having a suitable yield stress. Sugar solutions, polyols, of which glycerol is an example, alcohols, particularly ethanol, isopropanol, and the like, are good examples of suitable liquids that can be in admixture with water in the liquid medium. It may also be convenient to fragment the starch hydrolysate in a non-hydrating medium (e.g., 95% ethanol), then solvent exchange with water, and finally redisperse the fragmented starch hydrolysate to form an aqueous dispersion. Typically, however, the starch hydrolysate will be physically fragmented in potable water. Thus, this invention relates to a method of making an aqueous dispersion useful as a replacement for fats and/or oils comprising physically fragmenting a minor amount by weight of an amylopectin starch hydrolysate in the presence of a major amount by weight of a liquid consisting essentially of water, said physically fragmenting being effective to yield an aqueous dispersion having a yield stress of from about 100 pascals to about 1,500 pascals.

The mechanical disintegration is preferably accomplished by subjecting an aqueous dispersion of the hydrolysate to high shear, e.g., in a Waring blender or a homogenizer such as that disclosed in U.S. Pat. No. 4,533,254 (Cook et al.) and commercially available as a "MICROFLUIDIZER" from Microfluidics Corporation, Newton, Mass., or a homogenizer such as the RANNIE TM high pressure laboratory homogenizer, Model Mini-lab, type 8.30 H, APV Rannie, Minneapolis, Minn. The temperature of the starch hydrolysate must be maintained below the gelatinization (i.e., solubilization) temperature of the hydrolysate. Thus, it may be necessary to cool the hydrolysate during disintegration. For example, when shearing starch hydrolysate derived from waxy maize starch, the temperature of the aqueous dispersion is typically maintained between about 55° C. and about 65° C. Whatever method is used, the disintegration is carried out to such an extent that the resulting finely-divided product is characterized by its ability to form a salve-like suspension in the liquid medium in which it is attrited or in which it is subsequently dispersed. By a salve-like suspension or dispersion is meant one which will exhibit, at about 20% hydrolysate solids, a yield stress of at least about 100 pascals, typically from about 100 pascals to about 2,000 pascals.

It should be noted that it has been found that an aqueous dispersion of the hydrolysate generally exhibits an increase in viscosity over a period of hours following the mechanical disintegration. Thus, the yield stress values herein denote the yield stress about three hours after mechanical disintegration unless otherwise noted. It should also be noted that mechanical disintegration may be sufficient to produce an aqueous dispersion having the desired yield stress, but still leave a sufficient number of particles of sufficient size to exhibit a "particulate" or "chalky" mouthfeel when ingested. Such chalkiness can be reduced by reducing the particle size of the starch hydrolysate before, during or after mechanical disintegration so that substantially all (typically at least about 95%, preferably at least 99%) of the hydrolysate will pass a U.S. #400 mesh sieve (i.e., substantially all particles are less than 15 microns). An example of a milling device suitable for such size reduction is a TROST TM Air Impact Mill from Garlock, Inc., Newton, Pa.

It has further been found that the use of a homogenizer as disclosed in U.S. Pat. No. 4,533,254 is facilitated by the addition of a small amount (e.g., 5% by weight of the starch hydrolysate dry solids) of an emulsifier to the aqueous slurry of starch hydrolysate fed to the homogenizer. When relatively high solids slurries of starch hydrolysate are fed into the homogenizer without added emulsifier, the homogenizer tends to plug after extended operation. The addition of emulsifier (for example, a mixture of mono- and di-fatty acid glycerides, e.g., DUR-LO TM emulsifier from Van Den Bergh Foods) prevents this plugging of the homogenizer. Other emulsifiers include polyglycerol esters, polysorbates, ethoxylated monoglycerides, sorbitan monostearate, lactylated esters, and lecithin.

The use of the fragmented, amylopectin starch hydrolysate allows for the replacement of a substantial portion (e.g., from 10% to 100% by weight) of the fat and/or oil in a food formulation. The precise level of replacement that is possible without significantly decreasing the organoleptic quality of the food will generally vary with the type of food. For example, in a French-style salad dressing, it is generally possible to completely replace the oil component that is normally present. In other types of foods, e.g., frostings, icings, cream fillings, ice cream, margarine, etc., a major amount of the fat and/or oil (e.g., about 50% to about 80%) can be replaced with little effect on the organoleptic desirability of the food. Examples of typical foods in which fat and/or oil can be replaced include frostings (e.g., icings, glazes, etc.), creme fillings, frozen desserts (e.g., ice milk, sherbets, etc.), dressings (e.g., pourable or spoonable salad and/or sandwich dressings), meat products (e.g., sausages, processed meats, etc.), cheese products (e.g., cheese spreads, processed cheese foods), margarine, fruit butters, other imitation dairy products, puddings (e.g., mousse desserts), candy (e.g., chocolates, nougats, etc.), and sauces, toppings, syrups and so on.

Generally, it will be desirable to remove sufficient fat from a given food formulation to achieve a reduction in calories of at least one-third per customary serving or make a label claim of "cholesterol-free". (In this regard, see, for example, the list of standard serving sizes for various foods published in Food Labeling; Serving Sizes, 55 Fed. Reg. 29517 (1990) (to be codified at 21 C.F.R. 101.12), the disclosure of which is incorporated herein by reference, and the restrictions on labelling "cholesterol-free" at Food Labelling; Definitions of the Terms Cholesterol Free, Low Cholesterol and Reduced Cholesterol, 55 Fed. Reg. 29456 (1990)). It should also be noted that the fat removed from a particular formulation may be replaced with an equal amount by weight of an aqueous dispersion of fragmented starch hydrolysate, but that such equality may not be necessary or desirable in all instances. Further, it may be desirable to remove fat and add another ingredient (e.g., a gum, polydextrose, a protein, etc.) along with the aqueous dispersion of starch hydrolysate.

While this invention is generally directed to the replacement of fat and/or oil in a food formulation, it is of course within the contemplation of this invention that a fragmented granular amylopectin starch hydrolysate will be used in an entirely new formulation to which it contributes fat-like organoleptic qualities but is not, in the strictest sense, replacing a pre-existing fat or oil ingredient. Moreover, it is contemplated that the fragmented granular amylopectin starch hydrolysate will have utility as a thickener, bodying agent, or the like in foods that normally do not have a significant fat or oil component. Further, it is contemplated that the combined use of fragmented granular amylopectin starch with fragmented, granular amylose starch (e.g., as a blend) may have certain advantages in many of the compositions described herein. For example, the amylopectin based material may promote a unique consistency while the amylose based material provides greater heat stability to the blend.

In general, the fragmented granular starch hydrolysate is incorporated into the food as an aqueous dispersion, typically comprised of a major amount (i.e., greater than 50% by weight) of water or other liquid medium and a minor amount (i.e., less than 50% by weight, typically 10% to 40%) of starch hydrolysate solids. Thus, this invention relates to an aqueous dispersion useful as a replacement for fats and/or oils comprising a major amount by weight of water and a minor amount by weight of a fragmented granular starch hydrolysate, said fragmented granular starch hydrolysate being capable of imparting to said dispersion at about 20% solids a yield stress of from about 100 to about 1,500 pascals. Alternatively, the isolated hydrolysis product can be mixed with the food along with water and then subjected to disintegration in those instances when the other ingredients of the food are capable of withstanding the condition of disintegration, e.g., a salad dressing or imitation sour cream.

It is contemplated that commercial production and use may involve hydrolysis, mechanical disintegration, and drying (e.g., spray drying) of the fragmented starch hydrolysate to produce an item of commerce. This item of commerce will then be purchased by a food processor for use as an ingredient. To incorporate the dried, fragmented granular starch hydrolysate into a food product, it may be useful and/or necessary to further mechanically disintegrate the starch hydrolysate while dispersing it into the foodstuff in which it will be employed. However, the techniques employed for such mechanical disintegration should not need to be nearly as vigorous as the original mechanical disintegration prior to drying.

The fragmented, amylopectin starch hydrolysate, as well as other granular starch hydrolysates within the scope of this disclosure, should not be subjected to conditions (e.g., elevated temperature) which will cause the hydrolysate fragments (i.e., a majority by weight thereof) to dissolve. Thus, if the food formulation is to be cooked or otherwise heated, to temperatures sufficient to gelatinize (i.e., dissolve) the hydrolysate, such heating should be completed prior to the addition of the hydrolysate to the food. It should be noted, however, that in many foods that are cooked, e.g., cheesecake, the internal temperature and/or moisture availability may be insufficient to dissolve the starch hydrolysate fragments.

As noted above, the terms "food" and "foodstuffs" are intended broadly, as relating to both nutritional and/or functional food ingredients. It is contemplated that one or more food ingredients may be mixed with the aqueous dispersion of fragmented, amylopectin starch hydrolysate, or even dry mixed with the amylopectin starch hydrolysate prior to mechanical disintegration.

Among the food ingredients in the food formulations of this invention include flavors, thickeners (e.g., starches and hydrophilic colloids), nutrients (e.g., carbohydrates, proteins, lipids, etc.), antioxidants, antimicrobial agents, non-fat milk solids, egg solids, acidulants, and so on.

Hydrophilic colloids can include natural gum material such as xanthan gum, gum tragacanth, locust bean gum, guar gum, algin, alginates, gelatin, Irish moss, pectin, gum arabic, gum ghatti, gum karaya and plant hemicelluloses, e.g., corn hull gum. Synthetic gums such as water-soluble salts of carboxymethyl cellulose can also be used. Starches can also be added to the food. Examples of suitable starches include corn, waxy maize, wheat, rice, potato, and tapioca starches.

Generally, the fragmented granular starch hydrolysate will be employed in foods which in finished form (the form intended for human consumption) contain a granular starch component. In some foods, e.g., margarine, the granular starch hydrolysate itself will typically be the only granular starch component. Along this same line, in other foods, e.g., Danish pastry, there will be a starch component in the one element of the food (e.g., the dough) which will be gelatinized during baking, and thus that starch component is not "granular", but any fragmented starch hydrolysate used in the roll-in should remain ungelatinized or undissolved. Thus, again, the fragmented granular starch hydrolysate may be the only granular starch component. The other baked goods, e.g., cookies, crackers, and the like, wherein little if any of the starch in the flour (e.g., wheat flour, a starch component) will gelatinize, and thus, the fragmented granular starch hydrolysate will be only one granular starch component. However, in baked goods (such as layer cakes) wherein the starch in the flour must gelatinize as part of the development of the cellular structure of the layer cake, there generally can be no "granular starch component" (at least no amylopectin granular starch component) therein because starch gelatinization must occur during the baking of the layer cake.

Non-fat milk solids which can be used in the compositions of this invention are the solids of skim milk and include proteins, mineral matter and milk sugar. Other proteins such as casein, sodium caseinate, calcium caseinate, modified casein, sweet dairy whey, modified whey, and whey protein concentrate can also be used herein.

For many foods, it is accepted practice for the user to add the required amount of eggs in the course of preparation and this practice may be followed just as well herein. If desired, however, the inclusion of egg solids, in particular, egg albumen and dried yolk, in the food are allowable alternatives. Soy isolates may also be used herein in place of the egg albumen.

Dry or liquid flavoring agents may be added to the formulation. These include cocoa, vanilla, chocolate, coconut, peppermint, pineapple, cherry, nuts, spices, salts, flavor enhancers, among others.

Acidulants commonly added to foods include lactic acid, citric acid, tartaric acid, malic acid, acetic acid, phosphoric acid, and hydrochloric acid.

Generally, the other components of the various types of food formulations will be conventional, although precise amounts of individual components and the presence of some of the conventional components may well be unconventional in a given formulation. For example, the conventional other components for foods such as frozen desserts and dressings, are described in European Pat. Publication No. 340,035, published November 2, 1989, (the pertinent disclosure of which is incorporated herein by reference) and the components and processing of table spreads is disclosed in U.S. Pat. No. 4,869,919 (Lowery), the disclosure of which is incorporated by reference.

A particularly advantageous use of the fragmented starch hydrolysates described herein is the use thereof to replace a portion of the shortening used in a layered pastry article. In layered pastry articles (Danish, croissants, etc.) layers of a bread dough are assembled with a "roll-in" placed between the layers. The roll-in commonly contains a "shortening" (i.e., a fat and/or oil component) from an animal (e.g., butter) or vegetable (e.g., partially hydrogenated soybean oil) source. The assembled article, optionally containing a filling or topping, is then baked to form a finished pastry.

It has been found that at least a portion of the shortening of an otherwise conventional roll-in can be replaced with an aqueous dispersion of fragmented starch hydrolysate, preferably in admixture with an emulsifier (e.g., mono- and/or di-glycerides), and used to make a layered pastry. Further, not only does the resulting pastry have excellent organoleptic qualities when fresh from the oven, but many of these excellent qualities are maintained (at least with an amylopectin starch hydrolysate) for an extended period of time under conventional ambient temperature storage conditions. Thus, the use of such a roll-in should extend shelf life of the finished pastry. In particular, the little, if any, observable change in texture of a Danish prepared as described herein is a surprising and distinctly useful advantage over conventional Danish. Moreover, the Danish, when reheated in a microwave appears remarkably resistant to microwave toughening.

The following examples will illustrate the invention and variations thereof within the scope and spirit of the invention will be apparent therefrom. All parts, percentages, ratios and the like are by weight throughout this specification and the appended claims, unless otherwise noted in context.

EXAMPLES

Test Methods

In the following examples, the tests described below were used.

Cold-Water Solubility and Insolubility

The determination of the cold-water solubility of the starch hydrolysate samples can be carried out by the following specific procedure involving mixing a starch sample with water in a Waring blender; centrifuging the mixture, evaporating an aliquot of the supernatant liquid and weighing the residue as solubles. The equipment utilized in measuring cold-water solubility is as follows:

(1) Waring blender (Model PB5) equipped with semi-micro monel metal cup (Fisher Scientific Catalog No. 14-509-07);
(2) International Centrifuge Model K or similar;
(3) Centrifuge tubes, 100 ml, and evaporating dish;
(4) Balance; and
(5) Oven.

The cold-water solubility measurement is carried out according to the following procedure:

1. Measure exactly 100 ml of distilled water at ambient temperature into the Waring blender cup.
2. Turn the blender on slow speed (about 6,100 rpm) and add 1.000 gram of starch sample over less than a 15 second period, then stir for 2 minutes on high speed (about 13,500 rpm).
3. Fill a 100 ml centrifuge tube with the starch solution/suspension and centrifuge at maximum speed (3,100 rpm is satisfactory) for 15 minutes.
4. Transfer a 25 ml aliquot of the supernatant to a tared evaporating dish and evaporate on a steam bath to apparent dryness.
5. Dry in an oven at 110° C. for at least 1 hour (overnight is satisfactory) and weigh.

Cold-water solubility, expressed as percent water solubles by weight (d.s.b.), is then calculated according to the following formula:

$$\% \text{ water solubles } (d.s.b.) = \frac{(\text{wt. of solids in 25 ml}) \times 4}{(\text{wt. of sample}) \times \frac{(\% \text{ Moisture})}{100}} \times 100$$

Cold-water insolubility, expressed as percent water insolubles by weight (d.s.b.), is then calculated by subtracting cold-water solubility from 100.

Yield Stress

This test measures the yield stress of a dispersion of mechanically disintegrated starch hydrolysate stored for at least three hours. A viscometer (model Rotovisco 1 from Haake) on a 500 setting is used with a Six Bladed Star Shaped Rotor (FL/RS), Gebruder Haake K. G., Saddle Brook, N.J. The procedure is as follows.

Clamp a container of the undisturbed dispersion on the stand and cover the vane rotor with the sample by raising the sample under the rotor to immerse the rotor in the sample (e.g., by bringing the rotor to the bottom of sample container and dropping the sample slightly, making sure rotor remains covered). The sample is then allowed to rest about three minutes after insertion of the vane rotor.

Turn gear shift on top of viscometer to 162 position (the lowest rpm) and watch reading. After it peaks, turn gear shift to the left. The peak value is used to calculate the unstirred yield stress as follows: peak value (as percent of full scale) $\times 29.72 =$ yield stress in pascals (Pa).

Yield stress can also be measured using a Brookfield (Model 5XHBTDV-II) viscometer or a Bohlin (Model VOR) viscometer, fitted with a rotor having the same geometry and dimensions (on the probe end) as the Haake rotor described above. The yield stress values obtained using any of the above can be compared to the values generated by the Haake and a correlation curve established, thus allowing the use of any of the above viscometers to measure yield stress.

"b" Value:

The "b" value is obtained by measuring the viscosity of the hydrolysis slurry at different shear rates so that a power fraction can be calculated. The viscosity of a starch hydrolysate reaction slurry (at 30% to 40% solids, neutralized to a pH of 4-4.5 with sodium hydroxide (but optionally without neutralization) and cooled from the reaction temperature to room temperature) is measured with a Brookfield (BV) viscometer (Spindle #4). The Brookfield Apparent Viscosity is measured in cps at 50 rpm and 5 rpm. The "b" value is then calculated as the log of the ratio of the Brookfield Apparent Viscosity in cps at 50 rpm multiplied by 50 rpm to the Brookfield Apparent Viscosity in cps at 5 rpm multiplied by 5 rpm, i.e.:

$$\text{"b" value} = \log\left[\frac{(\text{Brookfield Apparent Viscosity})(50)}{(\text{Brookfield Apparent Viscosity})(5)}\right]$$

YSI dextrose

The dextrose content of the supernatant from a lab-centrifuged hydrolysis slurry (after neutralization) can be measured as follows:

Reagents
1. Distilled water.
2. YSI standard No. 2355, 200 and 500 mg/dl dextrose: Fisher Scientific No. 11-396-5 and 11-396-6. Must be kept refrigerated.
3. YSI buffer No. 2357: Fisher Scientific No. 11-396-14.
4. Purified water.

Apparatus
1. Yellow Springs Instrument, Model 27 Analyzer, Yellow Springs Instrument Co., Yellow Springs, Ohio.
2. Glucose Membrane: Fisher Scientific No. 11-396-18.
3. Syringepets, 25 μl: Fisher Scientific No. 11-396-28.
4. Volumetric Flasks, 10 ml capacity: Fisher Scientific No. 10-206-1A.
5. Disposable Pipets, 5.0 ml capacity, 1.0 ml×0.25: Samco, Catalog No. 222, Saint Amand Mfg. Co., San Fernando, Calif.
6. Disposable Cups, 5 ml: Fisher Scientific No. 11-396-10, or Yellow Springs Instrument Co. or equivalent.
7. Dispo Cup Holder: Yellow Springs Instrument Co.

Procedure
1. Tare a 10 ml volumetric flask on the balance.
2. Accurately weigh (or pipet) sample of supernatant into vial. Record weight.
3. With flask still on balance, bring total volume up to 10.0 ml mark with the distilled water. Record weight.
4. Put stopper on flask and shake well several times.
5. Allow samples to stand at room temperature, until equilibrated.
6. Calibrate YSI instrument.
7. Filter diluted sample into a plastic dispo sample cup.
8. Fill the 25 μl syringe with filtered sample from cup, rinsing the syringe two times with sample.
9. When YSI reads "0" and "INJECT", insert needle into septum and depress plunger. Hold plunger down until needle is pulled out of the septum.
10. The digital face on the YSI will display "WAIT". Wait for reading to appear on screen. Screen will display "READ".
11. Record the Reading.
12. After a sample is injected and read, the calibrant should be reinjected and the YSI recalibrated.

Calculations

Assuming density of diluted sample = 1,000 g/ml $$\% \text{ Dextrose} = [\text{mg/dl reading}] \times \left[\frac{1 \text{ dl}}{100 \text{ ml}}\right] \times \left[\frac{\text{g dil. soln.}}{\text{g sample}}\right] \times \left[\frac{1 \text{ g}}{1000 \text{ mg}}\right] \times 100\%$$

or $$\% \text{ Dextrose} = \frac{YSI \text{ mg/dl reading} \times (\text{sample wt. (g)} + \text{water wt. (g)})}{\text{Sample wt. (g)} \times 1000}$$

Molecular Weight Determination

Molecular weights were determined according to the principles set forth in Bouchard et al., above, and the experimental details set forth below.

Reagents and Standards
1. Dimethyl Sulfoxide, Burdick and Jackson, Cat. No. 081-4.
2. Sodium Nitrate, AR Grade, Mallenckrodt.
3. Milli-Q water, from Millipore Milli-Q system.
4. Polysaccharide Standards: M=853000, 100000, 12200, 5800, Polymer Laboratories Ltd., Essex Road, Church Stretton, United Kingdom.
5. Dextrose—NBS-41a, National Bureau of Standards.
6. Chromatographic Solv.: 0.01N $NaNO_3$ in 99.9/0.1: DMSO/Water(V/V).

Apparatus and Supplies
1. Waters Model 150C GPC, Waters Associates, Milford, Mass.
2. Spectra—Physics Model 4400 Chrom—Jet Integrator, Spectra—Physics, San Jose, Calif.
3. Winner 386, Laboratory Data Station, Spectra—Physics, San Jose, Calif.
5. Spectrum Electronic Signal Conditioner/Filter, Model 1021A.
6. Nylon Acrodisc 13, 0.45 micron disposable filters, Gelman Sciences, Ann Arbor, Mich.
7. WISP Autosampler Vials, 4 ml, Waters Associates.
8. 3.0 ml disposable syringes.

Procedure

Set instrument parameters as follows.
Waters 150C
1. External Reservoir=0.01N $NaNO_3$ in 99.9/0.1: DMSO/Water (V/V).
2. Flow Rate=0.5 ml/min.
3. Column/Detector Temp=35° C.
4. Injector Temp=35° C.
5. Pump Temp=35° C.
6. Detector Sensitivity=−128 (rel)
7. Scale Factor=4
8. Output via +/− integrator terminals
9. Injection Volume=100 microliters
10. Run Time=90 minutes
11. Max Pressure=50 Bars
12. Equil Delay=0
13. Initial Delay=0
14. Spin=Off
15. Filter=Off Spectra—Physics 4400 Integrator Out of dialog:
1. TW=0
2. PW=24
3. PT=1250
4. AT=64 mv
5. CS=0.1
6. OF=−80

Spectrum Filter
1. Cut Off Frequency=0.01
2. Attenuation/Gain=1

Standard Preparation
1. Into a clean, dry 4 dram screw cap vial weigh 10 milligram quantities of 853000, 100000, 12200, 5800 molecular weight polysaccharide standards and NBS 41a dextrose.
2. Pipet 10 ml of Chromatographic Solvent into the via and cap with a poly lined cap.
3. Warm the standard in a 50° C. bath, then shake to dissolve the components.
4. Filter 3 ml of standard solution to 4 ml WISP autosampler vials, using a Nylon Acrodisc 13 filter. Freeze standard when not in use.

Calibration
Calibrate using the standards set forth above and calculate a cubic fit of the data. The calibration is considered acceptable if the correlation factor is greater than 0.999.

Sample Preparation
1. Into a clean, dry 4 dram screw cap vial, weigh 8–10 mg of starch hydrolysate.
2. Pipet 4.0 ml of chromatographic solvent into the vial and cap with a poly lined cap.
3. Warm the sample and shake to dissolve sample (autoclave, if necessary, with high amylose starch hydrolysates, but not all of the sample need dissolve).
4. Filter 3 ml of the solution into a 4 ml WISP autosampler via using a Nylon Acrodisc 13 filter.

Sample Analysis
1. Using the sample function of the integrator, enter the sample number and sample identification for each sample.
2. Inject 100 microliters of each sample, capturing the data to the Winner 386 Laboratory Data Station Computer.
3. Inspect the chromatograms for normal area response and for normal baseline before and after sample elution.
4. Integrate using the software package and by estimating the appropriate curve parameters.

I. and II. GRANULAR HYDROLYSIS METHOD AND GRANULAR STARCH HYDROLYSATE COMPOSITION

Hydrolysis Study 1

Seventeen hydrolyses were run by the following method. Hydrochloric acid was prepared to a given concentration and heated to a specified temperature in a constant temperature water bath. Waxy maize starch was then added to the acid at 35% starch solids, the water of the starch diluting the acid to the molar concentration shown below. Zero time was arbitrarily designated as the time when all of the starch had been added to the acid. The reactions were carried out in a three-neck, round bottom flask. The center neck housed the stirring apparatus. One neck was set up with a cold water condenser to prevent loss of moisture during the reaction. The remaining neck was used as an addition port and for temperature monitoring. The reaction was stirred and the temperature maintained for a specified number of hours.

At the end of the specified time, the reaction was transferred to an ice bath, cooled and the pH adjusted to a pH of about 4–5 simultaneously. The product was then centrifuged. The supernatant was decanted, the sediment reslurried in water and centrifuged again. This procedure was repeated until the supernatant had a conductivity between 2,500 and 3,000 micromhos.

The product was then transferred to a stainless steel tray and oven dried at 65° C. overnight. The product was weighed and the yield calculated. After grinding, the product was passed through a U.S. #40 mesh sieve. The finished product was then submitted for dependent response evaluation. The conditions and analytical response data for each of the seventeen experiments are in Table 1. The starch hydrolysates were suspended in water at 20% solids and mechanically disintegrated using a MICROFLUIDIZER (as described below) employing an inlet temperature of 48°–49° C. and a pressure of 8,000 psi. The Dextrose Equivalent (DE) was measured as prescribed by the methods of A.O.A.C., 10th Ed., Lane-Eynon Volumeteric Method and Standard Analytical Methods of C.I.R.F., 2nd Ed., Methods E-26 and F-22.

TABLE 1

ACTUAL RESULTS OF HYDROLYSIS STUDY

| Sample | Time (Hours) | Temp. (°C.) | Acid Concentration (N) | "b" Value | Yield (Wt. %) | Dextrose Equivalent (DE) | Yield Stress (Pascals at 20% Dry Solids by Wt.) | Peak Molecular Weight (by GPC) |
|---|---|---|---|---|---|---|---|---|
| 1 | 5 | 56 | 0.50 | 1.26 | 94.3 | 0.95 | — | 105,114 |
| 2 | 20 | 56 | 0.50 | 0.63 | 73.9 | 2.66 | 24 | 13,251 |
| 3 | 20 | 56 | 1.00 | 0.14 | 50.9 | 5.48 | 347 | 4,923 |
| 4 | 5 | 56 | 1.00 | 0.92 | 81.8 | 2.03 | 10 | 35,722 |
| 5 | 5 | 64 | 1.00 | 0.33 | 43.0 | 4.80 | 461 | 5,350 |
| 6 | 20 | 64 | 1.00 | 0.22 | 15.5 | 9.70 | — | 4,618 |
| 7 | 20 | 64 | 0.50 | 0.05 | 36.4 | 6.90 | 798 | 5,350 |
| 8 | 5 | 64 | 0.50 | 0.31 | 75.1 | 3.00 | 71 | 11,529 |
| 9 | 10 | 60 | 0.75 | 0.40 | 59.6 | 3.80 | 203 | 5,350 |
| 10 | 10 | 60 | 0.75 | 0.40 | 61.9 | 3.62 | 155 | 5,350 |
| 11 | 10 | 60 | 0.75 | 0.42 | 59.2 | 3.85 | 123 | 5,350 |
| 12 | 20 | 60 | 0.75 | 0.04 | 40.8 | 6.42 | 733 | 4,973 |
| 13 | 10 | 64 | 0.75 | 0.05 | 38.2 | 5.71 | 894 | 4,973 |
| 14 | 10 | 56 | 0.75 | 0.62 | 81.4 | 2.59 | 27 | 14,216 |
| 15 | 10 | 60 | 0.50 | 0.55 | 72.6 | 2.74 | 51 | 12,358 |
| 16 | 5 | 60 | 0.75 | 0.47 | 70.1 | 2.20 | 19 | 27,783 |

TABLE 1-continued

| | | | ACTUAL RESULTS OF HYDROLYSIS STUDY | | | | |
|---|---|---|---|---|---|---|---|
| Sample | Time (Hours) | Temp. (°C.) | Acid Concentration (N) | "b" Value | Yield (Wt. %) | Dextrose Equivalent (DE) | Yield Stress (Pascals at 20% Dry Solids by Wt.) | Peak Molecular Weight (by GPC) |
| 17 | 10 | 60 | 1.00 | 0.19 | 49.8 | 6.80 | 429 | 5,328 |

The actual results shown in Table 1 were used to generate a mathematical model capable of predicting the results of using conditions within the parameters of the study design. The equations which comprise the model are set forth below, where Time is in hours, Temperature is in °C., Acid Concentration is in normality, Peak Molecular Weight is by gel permeation chromatography in g/mole and Yield Stress is in pascals.

"b" Value = .29855 − (.06753 * B) − (.02884 * A) + (.004304 * A * B) + (.1275 * A * C) − (.4000 * C) + (1.8197 * C$^2$) + (.004921 * B$^2$)

Peak Molecular Weight = e$^x$
where x = (8.62256 − (.1599 * B) − (.12065 * A) + (.01529 * A$^2$) − (1.5303 * C) + (.01255 * A * B) + (.1443 * A * C))

Yield (Wt. %) = 57.277 − (4.3525 * B) − (1.9380 * A) − (44.520 * C) + (.3617 * A * B * C) − (2.5598 * A * C) + (49.2619 * C$^2$)

DE = e$^x$
where x = (1.4853 + (.07156 * A) + (.1081 * B) + (1.2807 * C) − (.004772 * A$^2$) − (.08394 * A * C))

Yield Stress (Pascals) = (e$^x$)/2
where x = (6.1473 + (.4710 * A) + (.2545 * B) + (4.6661 * C) − (.01949 * A$^2$) − (.009686 * A * B) − (.2197 * B * C)) − 1 where:
A = (Time − 11.4706)
B = (Temperature − 60)
C = (Acid Concentration − 75)

This model was used to predict the following data in Table 1A.

TABLE 1A

| | PREDICTED VALUES FROM HYDROLYSIS STUDY | | | | | | |
|---|---|---|---|---|---|---|---|
| Data Point No. | Acid Concentration (N) | Temp. (°C.) | Time (Hours) | Peak Molecular Weight | Yield Stress (Pascals) | Yield (Wt. %) | "b" Value | Dextrose Equivalent (DE) |
| 1 | 0.5 | 62 | 14 | 4,766 | 333 | 58.70 | 0.282 | 4.83 |
| 2 | 0.5 | 62 | 16 | 4,885 | 405 | 54.46 | 0.242 | 5.20 |
| 3 | 0.5 | 63 | 12 | 4,348 | 395 | 59.18 | 0.250 | 4.90 |
| 4 | 0.5 | 63 | 14 | 4,044 | 550 | 54.76 | 0.218 | 5.49 |
| 5 | 0.5 | 63 | 16 | 4,251 | 656 | 50.34 | 0.186 | 5.92 |
| 6 | 0.5 | 64 | 10 | 4,264 | 416 | 60.02 | 0.210 | 4.79 |
| 7 | 0.6 | 61 | 14 | 4,890 | 315 | 56.06 | 0.256 | 4.78 |
| 8 | 0.6 | 61 | 16 | 4,888 | 390 | 52.07 | 0.207 | 5.16 |
| 9 | 0.6 | 62 | 12 | 4,641 | 358 | 56.04 | 0.235 | 4.81 |
| 10 | 0.6 | 62 | 14 | 4,210 | 509 | 51.95 | 0.195 | 5.39 |
| 11 | 0.6 | 62 | 16 | 4,315 | 618 | 47.86 | 0.154 | 5.82 |
| 12 | 0.6 | 62 | 18 | 4,998 | 643 | 43.76 | 0.114 | 6.04 |
| 13 | 0.6 | 63 | 10 | 4,734 | 362 | 56.25 | 0.207 | 4.66 |
| 14 | 0.7 | 60 | 14 | 4,874 | 311 | 54.72 | 0.250 | 4.82 |
| 15 | 0.7 | 60 | 16 | 4,751 | 393 | 50.85 | 0.192 | 5.19 |
| 16 | 0.7 | 61 | 12 | 4,813 | 339 | 54.37 | 0.241 | 4.81 |
| 17 | 0.7 | 61 | 14 | 4,257 | 491 | 50.45 | 0.192 | 5.39 |
| 18 | 0.7 | 61 | 16 | 4,255 | 609 | 46.54 | 0.143 | 5.81 |
| 19 | 0.7 | 61 | 18 | 4,807 | 646 | 42.63 | 0.094 | 6.03 |
| 20 | 0.7 | 62 | 12 | 4,099 | 546 | 50.13 | 0.184 | 5.38 |
| 21 | 0.7 | 63 | 10 | 4,242 | 541 | 49.88 | 0.169 | 5.17 |
| 22 | 0.8 | 59 | 14 | 4,720 | 321 | 54.71 | 0.265 | 4.93 |
| 23 | 0.8 | 59 | 16 | 4,487 | 413 | 50.79 | 0.199 | 5.32 |
| 24 | 0.8 | 59 | 18 | 4,821 | 455 | 46.88 | 0.133 | 5.52 |
| 25 | 0.8 | 60 | 12 | 4,849 | 336 | 54.15 | 0.268 | 4.88 |
| 26 | 0.8 | 60 | 14 | 4,183 | 496 | 50.27 | 0.210 | 5.47 |
| 27 | 0.8 | 60 | 16 | 4,077 | 626 | 46.40 | 0.152 | 5.90 |
| 28 | 0.8 | 60 | 18 | 4,492 | 677 | 42.52 | 0.095 | 6.13 |
| 29 | 0.8 | 61 | 12 | 4,190 | 529 | 49.68 | 0.214 | 5.42 |
| 30 | 0.8 | 62 | 10 | 4,511 | 502 | 49.01 | 0.210 | 5.16 |
| 31 | 0.9 | 57 | 16 | 4,466 | 306 | 56.40 | 0.280 | 5.04 |
| 32 | 0.9 | 57 | 18 | 4,563 | 351 | 52.20 | 0.196 | 5.23 |
| 33 | 0.9 | 58 | 14 | 4,441 | 346 | 56.00 | 0.301 | 5.14 |
| 34 | 0.9 | 58 | 16 | 4,117 | 454 | 51.91 | 0.226 | 5.54 |
| 35 | 0.9 | 58 | 18 | 4,314 | 510 | 47.82 | 0.151 | 5.76 |
| 36 | 0.9 | 59 | 12 | 4,746 | 347 | 55.39 | 0.315 | 5.05 |
| 37 | 0.9 | 59 | 18 | 4,078 | 742 | 43.44 | 0.116 | 6.33 |
| 38 | 0.9 | 60 | 12 | 4,161 | 535 | 50.68 | 0.264 | 5.55 |
| 39 | 0.9 | 61 | 10 | 4,660 | 488 | 49.74 | 0.272 | 5.25 |
| 40 | 1.0 | 56 | 20 | 4,403 | 419 | 49.58 | 0.141 | 5.58 |
| 41 | 1.0 | 57 | 14 | 4,060 | 389 | 58.62 | 0.358 | 5.44 |
| 42 | 1.0 | 57 | 20 | 4,330 | 586 | 45.36 | 0.107 | 6.09 |
| 43 | 1.0 | 58 | 12 | 4,513 | 375 | 58.09 | 0.383 | 5.30 |
| 44 | 1.0 | 58 | 20 | 4,258 | 818 | 41.14 | 0.084 | 6.65 |

TABLE 1A-continued

PREDICTED VALUES FROM HYDROLYSIS STUDY

| Data Point No. | Acid Concentration (N) | Temp. (°C.) | Time (Hours) | Peak Molecular Weight | Yield Stress (Pascals) | Yield (Wt. %) | "b" Value | Dextrose Equivalent (DE) |
| --- | --- | --- | --- | --- | --- | --- | --- | --- |
| 45 | 1.0 | 59 | 12 | 4,014 | 566 | 53.14 | 0.335 | 5.78 |
| 46 | 1.0 | 60 | 10 | 4,677 | 495 | 52.08 | 0.355 | 5.42 |
| 47 | 1.0 | 61 | 10 | 4,057 | 761 | 46.95 | 0.318 | 5.91 |

Hydrolysis Study 2

An expanded statistical design study was conducted to evaluate the effects of altering the temperature, time and hydrochloric acid concentration during the production of starch hydrolysate. Parameters of control were temperature (56° to 66° C.), time (5 to 24 hours), and acid concentration (0.4 to 1.0N). The design of Study 1 called for 11 preparations to find the interactions and see the basic contours. An additional 22 preparations were made for this study which cut down the variance by 13%. The additional experiments more clearly define the optimum conditions. The dependent responses used to determine optimum conditions were molecular weight by gel permeation chromatography (GPC), yield stress of a 20% d.s. salve (as measured by the Haake), and product yield.

Model equations were developed which predict the combination of independent variables which will result in dependent responses within a desired range. Using predicted independent variables, a starch hydrolysate was prepared at a lower level of acid. These conditions should produce less salt to be removed during product isolation. The product from this run met all dependent response criteria.

EXPERIMENTAL METHODS

A Box-Behnken experimental design was used to design this study. The Box-Behnken is a type of second order design that allows responses to be modeled as functions of linear, quadratic, and interaction of the independent variables. The independent variables chosen were temperature, acid level and reaction time. These were determined as critical for production by cursory formulation and reaction evaluation.

The temperature range was 56° to 66° C. The acid levels were 0.4N to 1.0N HCl. This means the actual concentration of aid in the liquid phase was at a set normality. The time range was 5 to 24 hours. All hydrolysis were run on 35% d.s. waxy starch. Thirty-three experiments were run by the following method.

The acid was prepared to a given concentration and heated to a specified temperature in a constant temperature water bath. The acid concentration was calculated on the basis of all of the water in the system. Zero time was arbitrarily designated as the time when all of the starch had been added to the acid. It required 20 minutes to add the 1,600 g of d.s. starch to the acid. The reactions were carried out in a three neck, 5 L, round bottom flask. The center neck housed the stirring apparatus. One neck was set up with a cold water condenser to prevent loss of moisture during the reaction. The remaining neck was used as an addition port and temperature check. The reaction was stirred at 200 rpm and the temperature maintained for the specified number of hours.

At the end of the specified time, the slurry was transferred to an ice bath and cooled to room temperature. The pH was adjusted to pH 4.0–4.5 with 14% sodium carbonate. The product was then centrifuged in the GSA rotor of an RC-5 Sorvall Superspeed centrifuge, at 8,000 rpm for 20 minutes. The supernatant was decanted and the sediment reslurried to the original weight then centrifuged again. This procedure was continued until the resulting supernate from centrifuging had a conductivity between 2,500 and 3,000 $\mu$mhos. The washed product was then transferred to a stainless steel tray and oven dried at 50° C. overnight.

After grinding in an electric coffee grinder, the product was passed through a U.S. #40 mesh sieve. The finished product was then submitted for dependent response evaluation. A specific example of the formulation follows.

HYDROLYSIS STUDY 2; DESIGN FORMULATION EXAMPLE

Conditions: 0.5N HCl, 35% d.s., 64° C., 12 hour hydrolysis 4571 g total slurry
1,600 g d.s. granular waxy maize starch, 1,844 g as is
2,971 g acid and water
18.24 g HCl/L for 0.5N
2,971 g acid and water/1.0073 g/ml=2,949 ml 0.5N HCl
2.949 L × 18.24 g/L=53.80 g HCl
53.80 g HCl/37.7%=142.7 g of 37.7% HCl (conc.)
2,971 g acid and water—142.7 g 37.3% HCl—244 g water in the starch=2,584 g water needed Weigh 2,584 g deionized water into a 5 L three neck flask and stir at 200 rpm.

Add 142.7 g 37.7% HCl and heat to 62° C. (The flask should have a cold water condenser in one of the necks to prevent loss of moisture during the reaction.)

When the acid solution reaches 62° C., add 1,844 g as is granular waxy maize starch (1,600 g d.s.). It takes about 20 minutes to add the starch. Zero time is considered to be when all the starch has been added.

The normality of the liquid phase is checked by a titer. 10 g of slurry is titrated with 0.1N sodium hydroxide to a methyl orange end point pH 4.0. From this, one can calculate meq HCl/g of slurry. Theoretically, there should be 0.322 meq HCl/g of slurry.

The hydrolysis is normally monitored by the "b" value which is the slope of the log ratio of two Brookfield viscosities taken at two different speeds. In this study, the viscosities were taken at the end of the reaction and recorded.

When the reaction has proceeded 12 hours, 1,500 g of slurry was transferred to an ice bath and neutralization was started simultaneously with 14% sodium carbonate. The reaction was adjusted to pH 4.0–4.5. The pH of the remainder of slurry was adjusted to 3.0 and stored in the refrigerator for possible use at a later time.

The pH 4.0 slurry was then placed in six large mouth, 300 ml centrifuge jars and centrifuged at 8,000 rpm for 20 minutes in the Sorvall centrifuge using the GSA rotor.

The supernatant was decanted and deionized water was added back to the original weight and centrifuged again. The amount decanted varied depending on the yield of the individual reaction. This procedure was repeated until the conductivity of the supernatants was less than 3,000 μmhos. This reaction required five washes. The number of times the wash was repeated depended on the normality of the acid used in the individual reaction.

The sediment was then placed on a stainless steel tray and dried overnight in a 50° C. forced air oven. The dried product was then ground in an electric coffee grinder and sifted through a U.S. #40 screen. The yield was calculated on the basis of the dry substance recovered after drying relative to the initial quantity of starch in the neutralized aliquot. In this example: 1,500 g slurry×0.35 (35% starch)=525 g starch, 252 g product recovered (252 g/525 g)×100=48.1%.

ANALYTICAL METHODS EMPLOYED

"b" Value

This method was run as above, but on unneutralized slurry.

Salve Preparation

Salves or creams were prepared using the Microfluidics Model 110T MICROFLUIDIZER. The dried product was dispersed in water at 20% solids and equilibrated to 50° C. before processing at a pressure of 8,000 psi.

Yield Stress

The yield stress of the salves was measured as above (using the Haake Rotovisco 1 at 3.6 rpm). It is expressed in pascals and correlates well with the molecular weight results.

Gel Permeation Chromatography

The molecular weight distribution of the products was determined by Gel Permeation Chromatography. The results are expressed as weight average molecular weight ($M_w$), number average molecular weight ($M_n$), ration $M_w/M_n$ and peak molecular weight (PMW). The results are very reproducible and do predict the yield/stress values.

% Product Yield

The percent product yield was calculated on the quantity of washed, dried product on a d.s. basis relative to the quantity of original dry starch.

Ash %

The ash values were determined in a conventional manner using a muffle furnace.

LOD %

Loss on drying was measured in the analytical department by oven losses.

Lubricity

Lubricity evaluation was determined for the first 17 preparations using an Instron. Lubricity measurement is the coefficient of friction defined by the ratio of sliding force to the normal force. The sliding force is measured under constant speed and the normal force is a non-applied weight. Because of the interference of bulk properties, this measurement could not be used to generate useful information and was dropped from the rest of this study.

RESULTS AND DISCUSSION

Table 1A below lists the conditions of preparation and the measured responses (actual results) for each reaction in this study.

TABLE 1A

ACTUAL RESULTS OF HYDROLYSIS STUDY 2

| Sample | Time (hrs.) | Temp. (°C.) | Acid Concentration (N) | "b" Value | Yield (wt. %) | Ash (wt. %) | Yield Stress (Pa) | Peak Molecular Weight | Mw | Mn | Mw/Mn |
|---|---|---|---|---|---|---|---|---|---|---|---|
| 1 | 5.0 | 56 | 0.50 | 1.26 | 94.3 | 0.18 | — | 91,066 | 106,224 | 21,297 | 5.00 |
| 2 | 20.0 | 56 | 0.50 | 0.63 | 73.9 | 0.31 | 48 | 12,392 | 16,382 | 6,929 | 2.40 |
| 3 | 20.0 | 56 | 1.00 | 0.14 | 50.9 | 0.46 | 693 | 4,512 | 6,031 | 3,418 | 1.80 |
| 4 | 5.0 | 56 | 1.00 | 0.92 | 81.8 | 0.19 | 19 | 28,862 | 24,683 | 8,390 | 2.90 |
| 5 | 5.0 | 64 | 1.00 | 0.33 | 43.0 | 0.52 | 921 | 4,849 | 7,294 | 3,916 | 1.90 |
| 6 | 20.0 | 64 | 1.00 | 0.22 | 15.5 | 0.72 | — | 4,512 | 4,106 | 1,929 | 2.10 |
| 7 | 20.0 | 64 | 0.50 | 0.05 | 36.4 | 0.53 | 1,595 | 4,734 | 6,246 | 2,841 | 2.20 |
| 8 | 5.0 | 64 | 0.50 | 0.31 | 75.1 | 0.26 | 142 | 11,274 | 14,268 | 6,185 | 2.30 |
| 9 | 10.0 | 60 | 0.75 | 0.40 | 59.6 | 0.29 | 406 | 8,204 | 9,359 | 4,406 | 2.10 |
| 10 | 10.0 | 60 | 0.75 | 0.40 | 61.9 | 0.22 | 310 | 8,780 | 9,840 | 5,118 | 1.90 |
| 11 | 10.0 | 60 | 0.75 | 0.42 | 59.2 | 0.34 | 246 | 8,978 | 9,840 | 5,019 | 2.00 |
| 12 | 20.0 | 60 | 0.75 | 0.04 | 40.8 | 0.38 | 1,466 | 4,734 | 5,579 | 3,306 | 1.70 |
| 13 | 10.0 | 64 | 0.75 | 0.05 | 38.2 | 0.37 | 1,788 | 4,734 | 6,094 | 3,585 | 1.70 |
| 14 | 10.0 | 56 | 0.75 | 0.62 | 81.4 | 0.20 | 53 | 22,874 | 18,050 | 6,807 | 2.70 |
| 15 | 10.0 | 60 | 0.50 | 0.55 | 72.6 | 0.17 | 101 | 12,392 | 15,800 | 6,426 | 2.50 |
| 16 | 5.0 | 60 | 0.75 | 0.47 | 70.1 | 0.27 | 37 | 27,187 | 20,994 | 7,499 | 2.80 |
| 17 | 10.0 | 60 | 1.00 | 0.19 | 49.8 | 0.93 | 857 | 4,734 | 6,305 | 2,730 | 2.30 |
| 18 | 14.0 | 61 | 0.70 | 0.17 | 51.5 | 0.56 | 1,199 | 5,100 | 7,184 | 2,989 | 2.40 |
| 19 | 16.0 | 62 | 0.50 | 0.43 | 51.8 | 0.33 | 878 | 4,734 | 6,962 | 3,435 | 2.00 |
| 20 | 18.0 | 62 | 0.50 | — | 51.7 | 1.07 | 939 | 7,816 | 7,843 | 3,273 | 2.40 |
| 21 | 8.0 | 66 | 0.40 | 0.45 | 75.4 | 0.28 | 208 | 20,264 | 15,915 | 5,403 | 2.90 |
| 22 | 10.0 | 66 | 0.40 | 0.49 | 62.8 | 0.55 | 269 | 20,265 | 15,915 | 3,448 | 2.90 |
| 23 | 10.0 | 64 | 0.50 | 0.45 | 53.2 | 0.42 | 593 | 11,537 | 13,913 | 4,768 | 2.90 |
| 24 | 12.0 | 64 | 0.50 | 0.39 | 48.1 | 0.28 | 893 | 7,816 | 8,332 | 3,448 | 2.40 |
| 25 | 22.5 | 64 | 0.40 | 0.28 | 57.0 | 1.25 | 832 | 4,746 | 6,153 | 1,281 | 4.80 |
| 26 | 24.0 | 64 | 0.40 | 0.10 | 51.3 | 1.41 | 870 | 4,746 | 5,565 | 1,167 | 4.80 |
| 27 | 18.5 | 64 | 0.70 | 0.11 | 34.7 | 2.07 | 1,123 | 4,526 | 3,873 | 891 | 4.30 |
| 28 | 24.0 | 64 | 0.70 | 0.04 | 31.0 | 2.16 | 5,290 | 4,746 | 3,615 | 798 | 4.50 |
| 29 | 17.5 | 56 | 0.70 | 0.60 | 74.7 | 0.73 | 194 | 9,212 | 10,174 | 2,594 | 3.90 |
| 30 | 24.0 | 56 | 0.70 | 0.57 | 64.8 | 1.03 | 202 | 7,425 | 7,581 | 1,911 | 4.00 |
| 31 | 8.0 | 56 | 0.40 | 1.34 | 90.1 | 0.29 | 240 | 79,447 | 80,592 | 7,269 | 11.10 |
| 32 | 16.0 | 56 | 0.40 | 1.08 | 80.7 | 0.17 | 300 | 29,886 | 30,061 | 6,722 | 4.50 |

TABLE 1A-continued

| | | | ACTUAL RESULTS OF HYDROLYSIS STUDY 2 | | | | | | | |
|---|---|---|---|---|---|---|---|---|---|---|
| Sample | Time (hrs.) | Temp. (°C.) | Acid Concentration (N) | "b" Value | Yield (wt. %) | Ash (wt. %) | Yield Stress (Pa) | Peak Molecular Weight | Mw | Mn | Mw/Mn |
| 33 | 24.0 | 56 | 0.40 | 0.68 | 67.9 | — | 710 | 22,526 | 18,013 | 5,362 | 3.40 |

The actual results shown in Table 1A were used to generate a mathematical model capable of predicting the results of using conditions within the parameters of the study design. The equations which comprise the model are set forth below.

MODEL OF STUDY 2

Yield Stress (Pascals) = $e^x$
where x = 6.21800 + 28.65331*TEMPX + 150.33889*TIMEX + 2.25031*ACIDX − 88.82924*TIME2 + 80.53618*ACID2 + 76.78657*TEMACI + 192.95592*TIMACI
(Std. dev. of fit in LOGe (yield stress) units = 0.606)
Yield (wt. %) = 53.65659 − 361.28054*TEMPX − 1590.33888*TIMEX − 48.10537*ACIDX + 719.23090*TIME2 − 422.89938*TEMACI + 172.98626*TEMP2
(Std. dev. of fit = 4.51)
Molecular Weight ($M_w$) = $e^x$
where x = 8.95612 − 12.35071*TEMPX − 79.76531*TIMEX + 29.22853*TIME2 − 2.17669*ACIDX + 47.37487*TIMTEM + 12.13814*TEMACI + 12.11837*TEMP2 + 64.59947*TIMACI + 24.31195*ACID2
(Std. dev. of fit in LOGe (molecular wt.) = 0.142)
wherein:
ACIDX = 0.63787878
TEMPX = 60.63636363
TIMEX = 13.98484848
ACID2 = ACIDX**2
TEMP2 = TEMPX**2
TIME2 = TIMEX**2
TEMACI = TEMPX*ACIDX
TIMACI = TIMEX*ACIDX
TIMTEM = TIMEX*TEMPX

TABLE 2A

| | PREDICTED RESULTS OF HYDROLYSIS STUDY 2 | | | | | |
|---|---|---|---|---|---|---|
| Data Point No. | Acid (N) | Temp. (°C.) | Time (hr.) | Mw | Yield Stress (Pa) | Yield (wt. %) |
| 1 | 0.5 | 60 | 24 | 6,447.98 | 541.37 | 53.5740 |
| 2 | 0.5 | 61 | 22 | 6,272.44 | 697.58 | 51.0842 |
| 3 | 0.5 | 61 | 24 | 5,857.17 | 648.56 | 50.4971 |
| 4 | 0.5 | 62 | 20 | 6,279.14 | 837.20 | 49.5157 |
| 5 | 0.5 | 62 | 22 | 5,782.44 | 835.70 | 48.3533 |
| 6 | 0.5 | 62 | 24 | 5,451.01 | 776.98 | 47.7662 |
| 7 | 0.5 | 63 | 18 | 6,468.67 | 935.85 | 48.8686 |
| 8 | 0.5 | 63 | 20 | 5,874.70 | 1,002.97 | 47.1308 |
| 9 | 0.5 | 63 | 22 | 5,461.50 | 1,001.18 | 45.9683 |
| 10 | 0.5 | 63 | 24 | 5,197.48 | 930.83 | 45.3812 |
| 11 | 0.5 | 64 | 18 | 6,142.02 | 1,121.15 | 46.8297 |
| 12 | 0.5 | 64 | 20 | 5,631.15 | 1,201.57 | 45.0918 |
| 13 | 0.5 | 64 | 22 | 5,284.92 | 1,199.42 | 43.9293 |
| 14 | 0.5 | 64 | 24 | 5,077.32 | 1,115.14 | 43.3422 |
| 15 | 0.7 | 58 | 22 | 6,007.36 | 511.89 | 53.9615 |
| 16 | 0.7 | 58 | 24 | 5,595.15 | 514.11 | 53.3745 |
| 17 | 0.7 | 59 | 18 | 6,401.79 | 572.78 | 52.2472 |
| 18 | 0.7 | 59 | 20 | 5,744.27 | 663.12 | 50.5094 |
| 19 | 0.7 | 59 | 22 | 5,276.23 | 715.04 | 49.3469 |
| 20 | 0.7 | 59 | 24 | 4,960.97 | 718.14 | 48.7598 |
| 21 | 0.7 | 60 | 16 | 6,387.70 | 643.69 | 50.2918 |
| 22 | 0.7 | 60 | 18 | 5,652.46 | 800.09 | 47.9786 |
| 23 | 0.7 | 60 | 20 | 5,120.19 | 926.29 | 46.2407 |
| 24 | 0.7 | 60 | 22 | 4,747.77 | 998.82 | 45.0782 |
| 25 | 0.7 | 60 | 24 | 4,506.59 | 1,003.15 | 44.4911 |
| 26 | 0.7 | 61 | 16 | 5,723.89 | 899.15 | 46.3691 |
| 27 | 0.7 | 61 | 18 | 5,113.28 | 1,117.63 | 44.0559 |
| 28 | 0.7 | 61 | 20 | 4,675.88 | 1,293.90 | 42.3180 |
| 29 | 0.7 | 61 | 22 | 4,377.05 | 1,395.22 | 41.1555 |
| 30 | 0.7 | 61 | 24 | 4,194.25 | 1,401.27 | 40.5685 |
| 31 | 0.7 | 62 | 14 | 5,964.81 | 941.15 | 45.6810 |
| 32 | 0.7 | 62 | 16 | 5,254.90 | 1,255.99 | 42.7924 |
| 33 | 0.7 | 62 | 18 | 4,739.01 | 1,561.18 | 40.4791 |
| 34 | 0.7 | 63 | 12 | 6,396.64 | 917.53 | 45.9143 |
| 35 | 0.7 | 63 | 14 | 5,557.51 | 1,314.66 | 42.4503 |
| 36 | 0.7 | 64 | 12 | 6,048.49 | 1,281.67 | 43.0295 |
| 37 | 1.0 | 56 | 20 | 6,314.32 | 648.40 | 56.8417 |
| 38 | 1.0 | 56 | 22 | 5,860.07 | 784.99 | 55.6793 |
| 39 | 1.0 | 56 | 24 | 5,567.18 | 885.17 | 55.0922 |
| 40 | 1.0 | 57 | 18 | 5,930.31 | 877.33 | 52.0043 |
| 41 | 1.0 | 57 | 20 | 5,427.68 | 1,140.37 | 50.2665 |
| 42 | 1.0 | 57 | 22 | 5,085.18 | 1,380.60 | 49.1040 |
| 43 | 1.0 | 57 | 24 | 4,877.00 | 1,556.77 | 48.5169 |
| 44 | 1.0 | 58 | 16 | 5,731.66 | 1,105.64 | 48.0882 |
| 45 | 1.0 | 58 | 18 | 5,173.41 | 1,542.98 | 45.7750 |
| 46 | 1.0 | 58 | 20 | 4,780.00 | 2,005.60 | 44.0371 |
| 47 | 1.0 | 58 | 22 | 4,521.00 | 2,428.10 | 42.8747 |
| 48 | 1.0 | 58 | 24 | 4,377.20 | 2,737.95 | 42.2876 |
| 49 | 1.0 | 59 | 14 | 5,700.77 | 1,297.79 | 45.0935 |
| 50 | 1.0 | 59 | 16 | 5,074.46 | 1,944.53 | 42.2049 |
| 51 | 1.0 | 60 | 12 | 5,834.96 | 1,418.84 | 43.0202 |
| 52 | 1.0 | 61 | 10 | 6,146.01 | 1,444.77 | 41.8682 |

The results of this study indicate it is possible to prepare a microcrystalline product with as low as 0.4N acid which will give a yield stress of greater than 800 pascals and slightly greater than 50% yield. Increasing the temperature to as high as 66° C. or increasing the reaction time makes it possible to tailor the process to optimize production conditions and still produce a starch hydrolysate product that meets desired characteristics.

EXAMPLE 1

Hydrochloric Acid Hydrolysis

An agitated reactor was charged with 103 gallons of tap water. To the highly stirred water was added 700 lbs. starch (at about 11% moisture, i.e., at 620 lbs. d.s. starch) slurry was heated to 54° C. (130° F.). (Prior to heating, the slurry was adjusted to 22.0°-22.6° Baumé, necessary, due to any variation in precise amount of water added or moisture content of the starch.) Concentrated (31.5%) hydrochloric acid, 112 lbs., was then added and the slurry was heated with low stirring to 60° C. (140° F.) and allowed to react for 10 to 12 hours, until a "b" value of about 0.08 to 0.10 was achieved.

A 14% solution of soda ash was then used to neutralize the slurry to a pH of 4.0–4.5 and then cooled to less than 100° F. The slurry was then diluted to 8–10% dry substance and centrifuged using a horizontal decanter centrifuge (Model 66 Sharples Super-D-Canter Centrifuge, Alfa-Laval Separation, Inc., Oak Brook, Ill.). The sediment was reslurried to 20% solids and centrifuged and washed to a wash water conductivity of 2,000 micromhos and the resulting wet solids were spray dried to 4–6% moisture using a Swenson 5'-0" diameter Parallel Flow Spray Dryer at air flow rate of 4,000–6,000 cfm, inlet temperature of 390°14 410° F., outlet temperature of 190°–210° F., slurry feed rate (with Manton Gaulin pump at 3,500–4,500 psi) 1–3 gpm, single fluid high pressure spray nozzle (53 orifice and 27 core from Spraying Systems Company, Wheaton, Ill.).

EXAMPLE 2

Sulfuric Acid Hydrolysis

A hydrolysis using sulfuric acid was run substantially as in Example 1 as described above with the following exceptions. Deionized water, 499 lbs., was employed with 354 lbs. of starch (at about 11% moisture) and 58 lbs. of concentrated sulfuric acid, and the reaction was run for about 10 hours to a "b" value of about 0.30. The reaction was neutralized to a pH of 3.8–4.2 and was centrifuged using a perforated basket centrifuge (12" diameter basket from Western States Machine Company, Hamilton, Ohio) and then reslurried and centrifuged until the soluble solids of the filtrate was 0.5% or less. The sediment was then tray dried at 105°–115° F. to a moisture of 8%.

EXAMPLE 3

The materials and procedure of Example 1 were employed with the exceptions that (i) a stacked disk, nozzle discharge centrifuge (Model C-9 Merco from Dorr-Oliver, Stamford, Conn.) was employed in the starch hydrolysate centrifugation and wash to produce a slurry at 10–15% solids having a conductivity of less than 4000 micromhos, and (ii) an alkaline pre-wash was performed according to the general teachings of U.S. Pat. No. 4,477,480, i.e., a slurry of granular starch starting material (at 22.0°–22.6° Baumé at 60° F.) was adjusted to a pH of 11.3–11.5 by the addition of aqueous sodium hydroxide (3% d.s. caustic), the slurry was then washed (by reslurry and recentrifuging using the centrifuge described immediately above) to 38–40% dry solids and 200–600 micromhos of conductivity and neutralized to a pH of 2.0 to 6.0 (with 20° Baumé hydrochloric acid).

EXAMPLE 4

The materials and procedure of Example 1 were employed with the exceptions that (i) the amounts of water, starch and hydrochloric acid were scaled back to 88 gallons of water, 600 lbs. of starch (at about 11% moisture), and 103 lbs. of concentrated (31.5%) hydrochloric acid, respectively, (ii) sodium hydroxide in the amount of 36 lbs. was used in place of the soda ash, (iii) the "b" value was measured after neutralization of a sample of the slurry, and (iv) a continuous, horizontal, vacuum belt filter (1.0M² Rigidbolt Horizontal Filtration Unit, Dorr-Oliver, Inc., Stamford, Conn.) was used to reduce the conductivity of the slurry to less than 3,000 micromhos (by reslurrying to 15% d.s. prior to each wash pass).

EXAMPLE 5

The materials and procedure of Example 4 were employed with the exceptions that (i) the slurry was heated to and reacted at 140° F. rather than 130° F. and (ii) a solid bowl, batch centrifuge (14" Solid Bowl S.T.M. 1000-146 Lab Unit Centrifuge, Western States Machine Company, Hamilton, Ohio) was employed by diluting the slurry to 5–10% d.s. and then separating the insoluble residue by centrifugation prior to any further washing (by reslurrying to 5–10% d.s. and recentrifuging).

EXAMPLE 6

An agitated reactor was charged with 219 gallons of tap water. To the highly stirred water was added 1,300 lbs. of starch, at about 11% moisture, i.e., 1,150 lbs. d.s. starch. (The slurry was then adjusted to 20.2°–21.2° Baumé at 60° F., if necessary, due to any imprecision in addition of water or any variation in moisture content of the starch). Then, 160 lbs. of 20 Baumé hydrochloric acid was added and the titer adjusted to 0.45 meq/g, if necessary. With the stirrer/agitator on low, the contents of the reactor were then heated to 141.8° F. and held at that temperature until a "b" value of less than 0.35 was obtained. (A sample was taken from the reactor, neutralized and analyzed for its "b" value at the sixth hour of reaction time and at each succeeding hour thereafter; typically the reaction was held at temperature for approximately 12–14 hours.)

A 5% caustic solution, prepared from 120 gallons of tap water and 100 lbs. 50% caustic, was then used to neutralize the slurry to a pH of 3.0–4.5. The neutralized slurry was then transferred to a holding tank and diluted to approximately 10% d.s. prior to dewatering and washing (by reslurrying to 10% d.s. dewatering) to an ash content of less than 2%, using the horizontal decanter centrifuge described in Example 1.

The dewatered starch hydrolysate was then diluted and spray dried substantially as in Example 1.

EXAMPLE 7

An agitated reactor was charged with 149 gallons of tap water. To the lightly stirred water was added 800 lbs. of starch (at about 11% moisture; i.e., about 708 lbs. d.s. starch) and the resulting slurry was adjusted to 20.2°–20.7° Baumé, if necessary. The slurry was then heated to 139° F. Then, 76 lbs. of 20° Baumé hydrochloric acid was added and the titer was adjusted to 0.322 meq/g, if necessary. The reactor agitator was the set on low and the contents were heated to 140° F. and held at 140° F. for 25 hours. After 8 hours, and every 2 hours thereafter, a sample was taken, neutralized and analyzed for "b" value and the dextrose content of the supernatant (by YSI Dextrose Method). After 25 hours, the slurry was neutralized to a pH of 3.0–4.0 with 50% caustic solution (sodium hydroxide), cooled to less than 100° F., and then diluted to 7% d.s. with tap water. The diluted slurry was then centrifuged using the solid bowl centrifuge described in Example 5, and then washed (by reslurrying to 7% and recentrifuging) until an ash content of 1–3% by weight was obtained. The centrifuge cake was then reslurried to 12% d.s. and spray dried as described in Example 1.

EXAMPLE 8

A granular starch hydrolysis can be performed using the equipment set forth in Example 7, but according to the following procedure.

Waxy maize starch is slurried to 36–37% d.s. and heated to 140° F. with tempered water. When the water temperature reaches 140° F., 20° Baumé hydrochloric acid is added to a 0.50N acid concentration and 35% reaction d.s. The temperature is then held at 140° F. for approximately 25 hours. The batch is reacted with minimal agitation throughout (agitator speed averaging 105 rpm). Reaction conversion rates may average 35–40% under these conditions, but as high as 48% may be possible. The dextrose content of the supernatant should be between about 1.9% and 2.2% "as is" (based on total supernatant weight) and the $M_w$ should be between about 5,450 g/mol and 5,775 g/mol.

At 35% d.s., the batch should not develop the high viscosity toward the end of the reaction as it has been found to develop at 37% d.s. This allows for quicker, more even neutralization with less localized "hot spots" from the caustic addition.

At the end of the reaction, the batch is cooled to 135° F. and 50% caustic (sodium hydroxide) is added (preferably metered through a dip leg at high flow rates) to adjust the pH to 3-4. A 5-7 degree exotherm may be observed. (Whereas it took approximately eight hours to neutralize with sodium carbonate in many of the runs described above, the neutralization time of Run No. 7 was down to 45-60 minutes.)

(A comparison of the insoluble solids weights before and after neutralization should indicate that very little solubilization of the product occurs from the addition when the pH target is met. Caustic strength and rate of addition may have very little effect compared to the effect of significantly overshooting the pH. At pHs over 8.0, some solubilization can occur and the starch picks up a yellow color. This color should revert somewhat when brought back to the acid side and eventually washes out altogether in the centrifuge. To prevent overshooting the pH, the slurry should be titered prior to neutralization.)

After pH adjustment, the batch is cooled to under 100° F. and diluted to approximately 7% insoluble solids for centrifugation. The dilution is calculated such that a 2% ash in the cake is achieved in only one wash pass. The solid bowl centrifuge is still the equipment of choice for the separation. Operating at 2500 g and low feed rates of 0.25-0.50 gpm, losses as low as 1-2% should be possible.

(By dropping from two and three wash passes to only one, it appears that the purity of the final product has dropped, i.e., the soluble solids fraction in the final product will be higher than a product produced with multiple wash passes.) Even though the ash target may be met, one wash pass may not remove enough of the soluble solids fraction for certain food formulations.

The cake from the centrifuge is reslurried to 12% total d.s., adjusted to 4.0-5.0 pH, and transferred to the spray dryer feed tank. The slurry is spray dried on the Swenson dryer with a single fluid, high pressure nozzle to 4-6% moisture. (This material spray dries very well. Very little accumulation occurs in the dryer; however, it appears that significant losses may occur out the exhaust stack, which indicates a need for a fine particle collection system on the dryer exhaust, e.g., bag house.) The product is packed in poly-lined fiber drums.

STARCH HYDROLYSATE RUNS

A series of runs were made based on each of the procedures described generally above in Examples 1-7. The details of each run, including any changes from the materials and procedures described above, are set forth in the tables below. Each run is denoted by a letter (A, B, C, D, etc.) that is distinctive within each Example. Thus, Run No. 4B was accomplished using the general procedure set forth in Example 4, but with any changes noted in following tables, Tables I-VII.

The reaction conditions for each run are shown in Table I, below. The starch used as a starting material was a granular waxy maize starch ("W") with the exception of Run Nos. 1A, 1D, 3A, 3B, which used dent corn starch (pure food product grade, "P") and Run No. 1C, which used a granular high amylose starch (HI-SET ™ C from National Starch and Chemical Co., "H"). In Table I, the 'Maximum Variance' column represents the maximum differential in the reaction temperature in degrees Fahrenheit. The 'A' and 'N' in the 'Final "b"' Value' column represent acid and neutralized "b" value tests (on final reaction samples before the batch was neutralized). The '*' for Run No. 4C means that the "b" value was run after the batch was neutralized. In the 'Base' column, 'S' stands for soda ash and 'N' stands for NaOH (sodium hydroxide), with the numerals indicating the % d.s. of each in the solution added to the slurry.

TABLE I

| | | | | | | | | Reaction Temperature | | | |
|---|---|---|---|---|---|---|---|---|---|---|---|
| | | | | | REACTION CONDITIONS | | | | | | |
| Run No. | Batch Size (lbs) | Base Starch | Acid Concentration (meq/gm) | Acid Concentration (N) | Reaction Solids (% d.s.) | Reaction Solids (lbs. d.s.) | Reaction Time (hrs.) | Average (°F.) | Maximum Variance (Δ °F.) | Final "b" Value | Neutralizing Base (wt. % d.s.) |
| 1A | 700 | P | — | 1.00 | 39.0 | 643.5 | 12.00 | 137.3 | 16.0 | 0.06 A | 14 S |
| 1B | 700 | W | — | 0.97 | 37.5 | 618.1 | 9.50 | 139.1 | 12.0 | 0.06 A | 14 S |
| 1C | 700 | H | — | 0.94 | 37.8 | 621.6 | 10.75 | 142.9 | 8.7 | 0.03 A | 14 S |
| 1D | 700 | P | — | 0.97 | 37.8 | 623.0 | 12.00 | 140.4 | 3.0 | 0.06 A | 14 S |
| 3A | 700 | P | — | 0.81 | 31.9 | 427.0 | 24.50 | 141.2 | 15.0 | 0.03 A | 14 S |
| 3B | 700 | P | — | 0.91 | 36.9 | 516.0 | 16.33 | 140.4 | 13.6 | 0.03 A | 14 S |
| 3C | 700 | W | 0.640 | 0.85 | 30.6 | 478.0 | 21.00 | 137.4 | 12.4 | 0.24 N | 14 S |
| 1E | 700 | W | 0.850 | 0.97 | 38.1 | 628.0 | 9.00 | 139.1 | 12.1 | 0.37 N | 3 N |
| 1F | 700 | W | 0.784 | 0.90 | 36.3 | 628.0 | 10.50 | 137.6 | 6.6 | 0.37 N | 5 N |
| 4A | 615 | W | 0.594 | 0.93 | 36.6 | 529.2 | 9.00 | 139.4 | 3.0 | 0.16 A | 5 N |
| 4B | 615 | W | 0.576 | 0.93 | 39.7 | 561.4 | 9.50 | 140.3 | 5.5 | 0.29 N | 5 N |
| 4C | 600 | W | 0.590 | 0.95 | 37.7 | 542.7 | 10.25 | 139.9 | 3.5 | *0.21 N | 5 N |
| 4D | 600 | W | 0.586 | 0.94 | 35.5 | 511.7 | 13.50 | 140.1 | 4.0 | 0.36 N | 5 N |
| 5A | 650 | W | 0.574 | 1.03 | 38.0 | 569.8 | 8.75 | 140.2 | 6.0 | 0.40 N | 5 N |
| 5B | 600 | W | 0.600 | 0.94 | 35.5 | 530.5 | 10.50 | — | — | 0.38 N | 5 N |
| 5C | 675 | W | 0.587 | 1.03 | 39.1 | 597.4 | 9.00 | 140.4 | 3.3 | 0.36 N | 5 N |
| 5D | 700 | W | 0.590 | 1.99 | 38.4 | 616.0 | 8.00 | 140.7 | 3.3 | 0.35 N | 5 N |
| 5E | 344 | W | 0.478 | 0.63 | 36.5 | 300.6 | 12.00 | 142.0 | 2.8 | 0.35 N | 5 N |
| 5F | 347 | W | 0.322 | 0.34 | 38.6 | 307.0 | 14.00 | 143.2 | 5.0 | 0.32 N | 5 N |
| 6A | 1,300 | W | 0.455 | 0.66 | 34.0 | 1,111.9 | 18.17 | 141.5 | 1.0 | 0.36 N | 5 N |
| 6B | 658 | W | 0.336 | 0.48 | 33.8 | 580.0 | 18.58 | 143.6 | 2.5 | 0.37 N | 10 N |
| 6C | 658 | W | 0.340 | 0.53 | 34.2 | 540.8 | 19.67 | 143.4 | 6.2 | 0.34 N | 25 N |
| 6D | 900 | W | 0.438 | 0.64 | 34.6 | 780.0 | 18.25 | 139.9 | 1.4 | 0.36 N | 25 N |
| 6E | 800 | W | 0.440 | 0.59 | 34.9 | 677.6 | 16.67 | 139.9 | 2.0 | 0.37 N | 50 N |

TABLE I-continued

REACTION CONDITIONS

| Run No. | Batch Size (lbs) | Base Starch | Acid Concentration (meq/gm) | Acid Concentration (N) | Reaction Solids (% d.s.) | Reaction Solids (lbs. d.s.) | Reaction Time (hrs.) | Reaction Temperature Average (°F.) | Reaction Temperature Maximum Variance (Δ °F.) | Final "b" Value | Neutralizing Base (wt. % d.s.) |
|---|---|---|---|---|---|---|---|---|---|---|---|
| 6F | 800 | W | 0.334 | 0.50 | 35.2 | 689.7 | 25.17 | 139.9 | 1.8 | 0.36 N | 50 N |
| 6G | 800 | W | 0.322 | 0.50 | 35.1 | 688.5 | 18.00 | 145.0 | 1.1 | 0.33 N | 50 N |
| 6H | 800 | W | 0.320 | 0.50 | 35.4 | 690.7 | 40.00 | 135.0 | 1.4 | 0.32 N | 50 N |
| 6J | 800 | W | 0.328 | 0.50 | 34.6 | 649.1 | 32.00 | 140.4 | 2.8 | 0.32 N | 50 N |
| 7 | 800 | W | 0.319 | 0.48 | 35.6 | 674.7 | 25.25 | 140.3 | 3.0 | 0.41 N | 50 N |

Tables II, III, IV, and V, set forth below describe the circumstances of each wash pass (for wash passes 1, 2, 3, and 4, respectively) of each run described in Table I. However, only those runs for which there was such a wash pass are listed in Tables II-IV. For example, only Run Nos. 4A, 4C, and 4D are listed in Table IV because only those runs employed 4 wash passes. The separation equipment used for each run shown in each table by the abbreviations set forth below.

| Abbreviation | Equipment |
|---|---|
| DNC | (Stacked) Disk, Nozzle (discharge) Centrifuge of Example 3 |
| HDC | Horizontal Decanter Centrifuge of Example 1 |
| HBF | Horizontal (vacuum) Belt Filter of Example 4 |
| SBC | Solid Bowl Centrifuge of Example 2 |

TABLE II

WASH PASS NO. 1

| Run No. | Wash Equipment | Feed Solids (% d.s.) | Conductivity of Feed (mmhos) | pH of Feed | Feed Solids (lbs., d.s.) | Wash Time (hrs) | Underflow Composition (% d.s.) | Underflow Composition (mmhos) | Overflow Composition (% d.s.) | Overflow Composition (mmhos) |
|---|---|---|---|---|---|---|---|---|---|---|
| 1A | HDC | 7.0 | 21,800 | 4.32 | 265.0 | 6.50 | 13.3 | 8,140 | 1.9 | 20,200 |
| 2B | HDC | 7.5 | 20,500 | 3.71 | 266.0 | 4.00 | 13.3 | 8,290 | 3.9 | 19,900 |
| 1C | DNC | 7.2 | 18,900 | 4.45 | 300.0 | 10.25 | 7.3 | 4,400 | 0.4 | 4,810 |
| 1D | DNC | 7.1 | 16,400 | 3.28 | 271.8 | 6.50 | 8.3 | 3,480 | 0.8 | 5,490 |
| 3A | DNC | 4.6 | 21,800 | 4.33 | 123.0 | 13.00 | 1.9 | 2,300 | 1.0 | 4,100 |
| 3B | DNC | 5.7 | 20,300 | 2.52 | 233.0 | 15.00 | 6.0 | 2,580 | 0.5 | 4,250 |
| 3C | DNC | 2.8 | 27,500 | 4.47 | 50.1 | 17.25 | 1.0 | 3,440 | 0.6 | 2,500 |
| 1E | DNC | 9.8 | 30,200 | 3.18 | 294.0 | 3.50 | — | 14,500 | — | 16,700 |
| 1F | DNC | 11.5 | 22,100 | 3.15 | 172.0 | 4.00 | 7.5 | 11,000 | 4.3 | 16,200 |
| 4A | HBF | 11.6 | 21,900 | 3.74 | 257.0 | 13.50 | 8.0 | 14,730 | 0.5 | 12,600 |
| 4B | HBF | 11.6 | 20,000 | 3.47 | 245.0 | 13.50 | 4.5 | 8,120 | 2.2 | 8,350 |
| 4C | HBF | 10.1 | 20,200 | 4.36 | 229.0 | 12.00 | 9.1 | 15,960 | 3.0 | 13,750 |
| 4D | HBF | 9.6 | 23,100 | 2.92 | 192.6 | 9.50 | 7.3 | 18,000 | 4.9 | 18,250 |
| 5A | SBC | — | 19,200 | 3.80 | 232 | 46.00 | 11.9 | 8,000 | 0.3 | 21,900 |
| 5B | SBC | 6.9 | 20,000 | 3.63 | 223.0 | — | 7.2 | 7,780 | 0.9 | 20,100 |
| 5C | SBC | 8.2 | — | 3.10 | 188.0 | — | — | — | — | — |
| 5D | SBC | 9.2 | 20,300 | 2.88 | 204.1 | 39.92 | 10.9 | 10,400 | 0.2 | 23,800 |
| 5E | SBC | 10.6 | 15,700 | 3.37 | 125.3 | — | — | — | — | — |
| 5F | SBC | — | 12,600 | 2.67 | — | — | — | 5,330 | — | — |
| 6A | HDC/SBC | 7.5 | 15,800 | 4.19 | 397.2 | 23.12 | 8.1 | 8,420 | — | — |
| 6B | SBC | 9.2 | 16,560 | 3.94 | 217.0 | — | — | — | 4.8 | — |
| 6C | SBC | 7.9 | 12,300 | 4.60 | 193.0 | — | — | — | 1.7 | — |
| 6D | SBC | 7.5 | 16,400 | 3.55 | 284.7 | 34.42 | 11.6 | 11,830 | 1.4 | 17,360 |
| 6E | SBC | — | 17,400 | 3.54 | — | — | — | — | — | — |
| 6F | SBC | 9.9 | 9,970 | 5.02 | 334.8 | 12.25 | 6.2 | 4,480 | 6.8 | 10,890 |
| 6J | SBC | 3.5 | 8,000 | 3.84 | 212.0 | 30.53 | 8.1 | 6,460 | — | 6,150 |
| 7 | SBC | — | — | — | — | — | — | — | — | — |

TABLE III

WASH PASS NO. 2

| Run No. | Wash Equipment | Feed Solids (% d.s.) | Conductivity of Feed (mmhos) | pH of Feed | Feed Solids (lbs., d.s.) | Wash Time (hrs.) | Underflow Composition (% d.s.) | Underflow Composition (mmhos) | Overflow Composition (% d.s.) | Overflow Composition (mmhos) |
|---|---|---|---|---|---|---|---|---|---|---|
| 1A | HDC | 7.8 | 6,610 | 2.35 | 202 | 4.25 | 18.5 | 3,040 | 2.50 | 6,390 |
| 1B | HDC | 4.8 | 4,470 | 3.20 | 72 | 3.00 | 18.7 | 1,600 | 1.60 | 4,500 |
| 1E | DNC | — | 14,500 | — | — | 8.00 | 5.6 | — | — | — |
| 1F | DNC | 7.9 | 12,220 | 3.78 | 155 | 3.25 | 5.0 | 6,200 | 0.30 | 8,100 |
| 4A | HBF | 8.0 | 14,730 | 5.50 | 141 | 9.75 | 3.4 | 5,660 | 0.40 | 10,200 |
| 4B | HBF | 4.5 | 8,120 | 3.47 | 174 | 20.00 | 4.7 | 3,530 | 0.04 | 6,200 |
| 4C | HBF | 9.1 | 15,960 | 3.22 | 109 | 6.40 | 9.6 | — | 3.40 | 11,630 |
| 4D | HBF | 5.6 | 16,000 | 3.50 | 145 | 12.00 | 5.3 | 9,680 | 4.30 | 16,840 |
| 5A | SBC | 7.9 | 6,200 | 4.75 | 200 | 27.50 | 9.5 | 2,000 | 0.68 | 7,000 |
| 5B | SBC | 7.2 | 7,780 | 5.88 | — | — | — | — | — | — |
| 5D | SBC | 7.7 | 8,240 | 3.40 | 168 | 23.00 | 10.7 | 2,095 | 2.26 | 8,990 |
| 5E | SBC | — | — | — | — | — | — | — | — | — |
| 6A | SBC | 7.4 | 7,500 | 3.50 | 127.9 | 17.10 | 5.5 | 2,390 | 1.83 | 6,980 |

TABLE III-continued

| | | | | WASH PASS NO. 2 | | | | | |
|---|---|---|---|---|---|---|---|---|---|
| Run No. | Wash Equipment | Feed Solids (% d.s.) | Conductivity of Feed (mmhos) | pH of Feed | Feed Solids (lbs., d.s.) | Wash Time (hrs.) | Underflow Composition (% d.s.) | (mmhos) | Overflow Composition (% d.s.) | (mmhos) |
| 6B | SBC | 5.8 | — | — | — | — | — | — | — | — |
| 6C | SBC | 16.7 | — | — | — | — | — | — | 0 | — |
| 6D | SBC | 5.0 | 7,000 | 3.39 | 193.8 | 21.07 | 11.2 | 2,260 | 1.22 | — |

TABLE IV

| | | | | WASH PASS NO. 3 | | | | | |
|---|---|---|---|---|---|---|---|---|---|
| Run No. | Wash Equipment | Feed Solids (% d.s.) | Conductivity of Feed (mmhos) | pH of Feed | Feed Solids (lbs., d.s.) | Wash Time (hrs.) | Underflow Composition (% d.s.) | (mmhos) | Overflow Composition (% d.s.) | (mmhos) |
| 1A | HDC | 9.9 | 2,780 | 4.30 | 156 | 2.50 | 11.1 | 917 | 2.9 | 3,000 |
| 1E | DNC | — | — | — | — | 2.10 | 1.5 | 2,580 | 0.0 | 4,500 |
| 1F | DNC | 5.5 | 6,200 | 3.81 | 154 | 2.25 | 4.4 | 2,350 | 1.7 | 3,700 |
| 4A | HBF | 3.4 | 5,660 | 3.00 | 69 | 6.30 | — | 3,530 | 0.4 | 4,870 |
| 4B | HBF | 4.7 | 3,530 | 3.40 | 114 | 18.70 | 11.0 | 1,703 | 0.6 | 3,150 |
| 4C | HBF | 9.6 | — | 3.26 | 42 | 6.00 | 5.8 | 7,590 | 1.2 | 5,010 |
| 4D | HBF | 5.3 | 9,680 | 3.50 | 64 | 5.60 | 6.8 | 8,240 | 3.8 | 11,160 |

TABLE V

| | | | | WASH PASS NO. 4 | | | | | |
|---|---|---|---|---|---|---|---|---|---|
| Run No. | Wash Equipment | Feed Solids (% d.s.) | Conductivity of Feed (mmhos) | pH of Feed | Feed Solids (lbs., d.s.) | Wash Time (hrs.) | Underflow Composition (% d.s.) | (mmhos) | Overflow Composition (% d.s.) | (mmhos) |
| 4A | HBF | — | 3,530 | 4.41 | 35 | 2.75 | 12.6 | 1,900 | 0.6 | 4,000 |
| 4C | HBF | 5.8 | 7,590 | 2.80 | 45 | 4.00 | 7.4 | 6,900 | — | 6,190 |
| 4D | HBF | 3.2 | 5,000 | 2.88 | 34 | 3.75 | 5.5 | 3,840 | 2.8 | 5,280 |

Table VI sets forth the circumstances of drying and the results for each run described in Table I. The "Orifice/Core" column sets forth the orifice and core part numbers (Spraying System Company, Wheaton, Ill.) used in the spray drying nozzle (except Run No. 4D wherein a rotary atomizer nozzle was used). The Feed Solids values are insolubles and total Dried Product is total solids, soluble and insoluble, salt, and moisture. In Run No. 1A, a portion of the starch hydrolysate product was tray dried to yield 30 lbs. In Run Nos. 5E and 5F, a portion of the starch hydrolysate product (81 lbs. and 91 lbs., respectively) was not washed, but it was dried. (These "total hydrolysate" portions were then used "as is" in various formulations described more fully below.)

TABLE VI

| | DRYING CONDITIONS | | | | | | |
|---|---|---|---|---|---|---|---|
| Run No. | Dryer Feed (% ds) | Conductivity of Feed (mmhos) | Feed Solids (lbs ds) | Pump Pressure (psig) | Orifice/ Core | Dried Product (lbs) | Final Moisture (%) |
| 1A | 11.0 | 1,050 | 66 | 2,500 | 52/28 | 16 | 7.3 |
| 1B | 4.5 | 1,280 | 54 | 3,800 | 52/28 | 49 | 5.5 |
| 1C | 4.8 | 3,980 | 190 | 4,700 | 56/27 | 180 | 4.7 |
| 1D | 8.3 | 3,330 | 188 | 5,500 | 56/27 | 148 | 5.5 |
| 3A | 1.9 | 2,300 | 22 | 4,700 | 56/27 | 11 | 6.5 |
| 3B | 6.0 | 2,500 | 90 | 5,000 | 56/27 | 74 | 5.5 |
| 3C | 1.0 | 3,760 | 12 | 4,000 | 56/27 | 12 | 4.8 |
| 1E | 1.5 | 2,710 | — | 4,000 | 56/27 | 57 | 5.0 |
| 1F | 4.3 | 2,350 | 88 | 4,500 | 56/27 | 84 | 4.4 |
| 4A | 4.1 | 1,900 | 22 | 3,700 | 56/27 | 22 | 6.8 |
| 4B | 9.8 | 1,703 | 60 | 5,000 | 56/27 | 81 | 4.0 |
| 4C | 4.6 | 5,580 | 6 | 5,000 | 55/27 | 16 | 6.1 |
| 4D | 5.5 | 3,840 | 7 | 15 | R.A. | 3 | — |
| 5A | 6.8 | 2,150 | 141 | 4,100 | 55/27 | 149 | 6.0 |
| 5B | — | — | — | — | — | 0 | — |
| 5C | — | — | — | — | — | 0 | — |
| 5D | 10.7 | 3,000 | 120 | 3,250 | 53/27 | 112 | 6.8 |
| 5E | 2.8 | — | 32 | 4,100 | 53/27 | 24 | 7.1 |
| 5F | — | 5,330 | — | 4,000 | 53/27 | 12 | 6.2 |
| 6A | 5.5 | 2,390 | 77 | 3,900 | 53/27 | 92 | 5.3 |
| 6B | — | — | — | — | — | 0 | — |
| 6C | — | — | — | — | — | 0 | — |
| 6D | 11.1 | 1,870 | 164 | 4,200 | 53/27 | 138 | 6.1 |
| 6E | — | — | — | — | — | 0 | — |
| 6F | — | 4,480 | — | 3,800 | 53/27 | 63 | 6.6 |
| 6G | — | — | — | — | — | 0 | — |
| 6H | — | — | — | — | — | 0 | — |
| 6J | 8.5 | 6,460 | 164 | 4,000 | 53/27 | 153 | 6.2 |

TABLE VI-continued

| | DRYING CONDITIONS | | | | | | |
|---|---|---|---|---|---|---|---|
| Run No. | Dryer Feed (% ds) | Conductivity of Feed (mmhos) | Feed Solids (lbs ds) | Pump Pressure (psig) | Orifice/ Core | Dried Product (lbs) | Final Moisture (%) |
| 7 | — | — | — | 4,100 | 53/27 | 0 | 5.4 |

Table VII sets forth the approximated losses of insoluble starch hydrolysate residue at each of the steps based on the calculated reaction conversion. The asterisk in the Calculated Reaction Conversion column denotes values calculated from samples taken after neutralization. (The reaction slurry was sampled and the insoluble residue of the samples was isolated using high g-force lab centrifuges followed by oven drying of the insoluble residue.) The remaining values were calculated based on solids isolated from samples taken after the reaction just prior to neutralization. In Run Nos. 3A, 3B, and 3C, the amounts recovered after alkaline wash were 202 lbs., 110 lbs. and 165 lbs., respectively. The percentages of losses and recoveries for these runs was based on total insoluble solids recovered after conversion.

TABLE VII

| | PRODUCT LOSSES | | | | | |
|---|---|---|---|---|---|---|
| Run No. | Reaction Conversion (%) | Neutralization Step (lbs.) | Wash No. 1 (lbs.) | Wash No. 2 (lbs.) | Wash No. 3 (lbs.) | Wash No. 4 (lbs.) |
| 1A | 37.3 | — | 63 | 46 | 90 | — |
| 1B | 56.0 | 58 | 217 | 18 | — | — |
| 1C | 52.2 | — | 110 | — | — | — |
| 1D | 43.6 | — | 84 | — | — | — |
| 3A | 39.5 | 45 | 101 | — | — | — |
| 3B | 49.2 | 21 | 143 | — | — | — |
| 3C | 10.5 | — | 38 | — | — | — |
| 1E | 46.8 | — | — | — | — | — |
| 1F | 44.1 | 105 | 17 | 1 | 66 | — |
| 4A | 48.6 | — | 116 | 72 | 34 | 15 |
| 4B | 45.1 | 0 | 71 | 60 | 54 | — |
| 4C | 45.3 | 17 | 120 | 67 | 0 | 36 |
| 4D | 37.6 | 0 | 48 | 81 | 30 | 27 |
| 5A | 40.7 | — | 32 | 59 | — | — |
| 5B | 47.4 | 28 | — | — | — | — |
| 5C | 31.4 | — | — | — | — | — |
| 5D | 40.4 | — | 36 | 48 | — | — |
| 5E | 45.9 | 13 | — | — | — | — |
| 5F | — | — | — | — | — | — |
| 6A | 36.2 | 5 | 269 | 51 | — | — |
| 6B | 42.4 | 29 | — | — | — | — |
| 6C | 46.8 | 33 | — | — | — | — |
| 6D | 36.5 | — | 89 | 32 | — | — |
| 6E | — | — | — | — | — | — |
| 6F | — | — | — | — | — | — |
| 6G | 41.2 | — | — | — | — | — |
| 6H | 17.7 | — | — | — | — | — |
| 6J | 32.7 | — | 0 | 64.2 | — | — |
| 7 | 45.5 | — | — | — | — | — |

| Run No. | Dryer Losses (lbs.) | Total Losses (%) | Total Recovered (%) | Total Recovered (lbs.) |
|---|---|---|---|---|
| 1A | 51 | 93.8 | 6.2 | 16 |
| 1B | 8 | 86.6 | 13.4 | 49 |
| 1C | 18 | 47.2 | 52.8 | 180 |
| 1D | 48 | 48.5 | 51.5 | 148 |
| 3A | 12 | 93.8 | 6.2 | 11 |
| 3B | 20 | 64.3 | 35.7 | 74 |
| 3C | 1 | 77.2 | 22.8 | 12 |
| 1E | — | 81.6 | 18.4 | 57 |
| 1F | 8 | 70.0 | 30.0 | 84 |
| 4A | 0 | 92.0 | 8.0 | 22 |
| 4B | 0 | 85.7 | 14.3 | 81 |
| 4C | 0 | 97.2 | 2.8 | 16 |
| 4D | 4 | 98.5 | 1.5 | 3 |
| 5A | 1 | 39.6 | 60.4 | 149 |

TABLE VII-continued

| 5B | — | — | — | 0 |
| 5C | — | — | — | 0 |
| 5D | 16 | 83.1 | 16.9 | 112 |
| 5E | 10 | 28.8 | 71.2 | 106 |
| 5F | — | 72.6 | 27.4 | 103 |
| 6A | 0 | 78.4 | 21.6 | 92 |
| 6B | — | — | — | 0 |
| 6C | — | — | — | 0 |
| 6D | 34 | 54.5 | 45.5 | 138 |
| 6E | — | — | — | 0 |
| 6F | — | — | — | 63 |
| 6G | — | — | — | 0 |
| 6H | — | — | — | 0 |
| 6J | 21 | 32.2 | 67.8 | 153 |
| 7 | — | — | — | 582 |

Table VIII sets forth the analytical values measured on the starch hydrolysate product recovered after drying (if any was recovered). The yield stress values were taken measured at 20% dry solids after fragmentation using the MICROFLUIDIZER ™ described above. Run No. 5F (TH), a total hydrolysate product, was also fragmented at 40% dry solids and a yield stress of 521 Pa was measured. The abbreviations in parentheses following certain run numbers indicate the drying of the product ("s" for spray dried; "t" for tray dried; or its distinction as total hydrolysate (TH)). No analysis was made of any product from Run No. 6G; thus, no entry therefore appears in Table VIII.

TABLE VIII

| | ANALYTICAL VALUES | | | | |
|---|---|---|---|---|---|
| Run No. | Moisture (%) | Foreign Matter (ppm) | Color (Hunter) | pH | 20% Yield Stress (Pa) |
| 2A | 9.16 | 5 | 10.4 | 7.90 | — |
| 2B | 7.41 | 2 | 7.0 | 3.70 | — |
| 2C | 7.56 | 2 | 17.8 | 8.53 | — |
| 2D | 9.21 | 2 | — | 5.45 | — |
| 1A(s) | 6.80 | 2 | 6.0 | 5.10 | — |
| 1A(t) | 7.50 | 2 | 6.3 | 5.20 | — |
| 1B | 4.95 | 2 | 8.6 | 4.10 | 545 |
| 1C | 4.65 | 5 | 7.7 | 3.24 | 525 |
| 1D | 5.55 | 5 | 7.8 | 5.30 | 458 |
| 3A | 6.27 | 5 | 5.5 | 3.80 | 327 |
| 3B | 5.14 | 4 | 5.3 | 3.30 | 550 |
| 3C | 4.57 | 10 | 6.4 | 4.40 | 115 |
| 1E | 4.44 | 2 | 4.9 | 4.30 | 372 |
| 1F | 4.67 | 2 | 7.9 | 4.00 | 223 |
| 4A | 3.56 | 2 | 5.8 | 4.63 | 559 |
| 4B | 3.88 | 2 | 12.6 | 3.86 | 481 |
| 4C | 5.74 | 2 | 9.0 | 3.69 | 337 |
| 4D | 4.90 | <50 | 8.2 | 4.00 | 493 |
| 5A | 5.78 | 5 | 9.0 | 4.40 | 503 |
| 5B | 6.26 | 2 | 11.2 | 4.80 | 503 |
| 5C | — | — | — | — | — |
| 5D | 6.84 | 2 | 7.4 | — | 503 |
| 5E(TH) | 6.83 | 8 | 7.4 | 4.08 | 606 |
| 5E | 6.74 | 5 | 7.2 | 6.58 | 636 |
| 5F(TH) | 6.61 | 2 | 11.4 | 3.33 | 86 |
| 5F | 5.45 | 5 | 9.0 | 4.04 | 296 |
| 6A | 4.74 | 2 | 7.9 | 3.90 | 598 |
| 6B | 7.60 | — | — | — | 513 |
| 6C | 5.50 | — | — | — | 381 |
| 6D | 5.66 | 3 | 9.7 | 5.47 | 743 |
| 6E | 6.40 | — | — | — | 330 |

TABLE VIII-continued

| | | | | | |
|---|---|---|---|---|---|
| 6F | 7.06 | 5 | 9.6 | 5.23 | 431 |
| 6H | — | — | — | — | 892 |
| 6J | 6.10 | 2 | 15.3 | 4.50 | 580 |
| 7 | — | — | — | — | — |

| Run No. | Ash (%) | GPM-Mw | Mw/Mn | GPC-PMW | Protein (%) |
|---|---|---|---|---|---|
| 2A | — | — | — | 4,150 | — |
| 2B | — | — | — | 4,150 | — |
| 2C | — | — | — | 4,000 | — |
| 2D | — | — | — | 5,060 | — |
| 1A( | — | — | — | 4,618 | — |
| 1A | — | — | — | 4,618 | — |
| 1B | 1.17 | 5,499 | 1.8 | 4,541 | — |
| 1C | 4.43 | 4,574 | 4.1 | 4,541 | — |
| 1D | 2.28 | 5,026 | 2.7 | 4,326 | — |
| 3A | 8.22 | 2,918 | 6.0 | 4,326 | — |
| 3B | 2.36 | — | — | — | 0.17 |
| 3C | 0.96 | 2,653 | 6.0 | 4,326 | 0.20 |
| 1E | — | 5,068 | 3.7 | 4,541 | 0.06 |
| 1F | 3.55 | 5,778 | 3.8 | 4,653 | 0.16 |
| 4A | 1.35 | 6,229 | 1.9 | 4,764 | 0.27 |
| 4B | 1.04 | 5,994 | 1.8 | 4,764 | 0.24 |
| 4C | 4.72 | 4,352 | 4.5 | 4,541 | 0.21 |
| 4D | 3.71 | 4,551 | 3.6 | 4,541 | — |
| 5A | 0.83 | 6,574 | 2.1 | 4,764 | 0.27 |
| 5B | 1.35 | 5,533 | 1.8 | 4,541 | 0.13 |
| 5C | — | — | — | — | — |
| 5D | 1.98 | 5,755 | 3.9 | 4,629 | 0.23 |
| 5E(TH) | 6.96 | 3,378 | 6.7 | 4,417 | 0.17 |
| 5E | 1.77 | 5,844 | 3.7 | 4,739 | 0.32 |
| 5F(TH) | 6.61 | 4,340 | 6.9 | 4,629 | 0.15 |
| 5F | 2.82 | 6,014 | 5.4 | 4,848 | 0.18 |
| 6A | 2.44 | 4,699 | 4.9 | 4,679 | 0.27 |
| 6B | — | 5,446 | 4.7 | 4,401 | — |
| 6C | — | 4,220 | 4.8 | 4,401 | — |
| 6D | 1.04 | 5,733 | 1.9 | 4,737 | 0.66 |
| 6E | — | 3,972 | 5.3 | 4,401 | — |
| 6F | 2.35 | 5,015 | 5.1 | 4,717 | 0.40 |
| 6H | — | — | — | — | — |
| 6J | 2.18 | 4,401 | 3.9 | 4,334 | 0.36 |
| 7 | — | — | — | — | — |

ALTERNATIVE METHODS OF MONITORING HYDROLYSIS

Samples of neutralized slurry from three different runs (each run using a different acid normality) were obtained during hydrolysis and were centrifuged. The supernatants were analyzed by (1) refractive index and (2) YSI dextrose analysis to assess these methods for following the hydrolysis. Correlation coefficients vs. yield stress values are reported below.

| Run No. | Acid Normality | Hydrolysis Time (hr) | Hydrolysate Yield (%, fb) | YSI Dextrose (%) | Refractive Index (@ 45 deg) | Yield Stress (Pa) |
|---|---|---|---|---|---|---|
| 5D | 1.0 | 4 | 60.6 | .55 | 1.3555 | 241 |
| 5D | 1.0 | 5 | 58.1 | .69 | 1.3570 | 317 |
| 5D | 1.0 | 6 | 54.4 | .87 | 1.3585 | 428 |
| 5D | 1.0 | 7 | 50.1 | 1.11 | 1.3600 | 583 |
| 5D | 1.0 | 8 | 46.6 | 1.48 | 1.3614 | 806 |
| 5E | 0.7 | 6 | 58.6 | .65 | 1.3575 | 382 |
| 5E | 0.7 | 8 | 52.7 | 1.03 | 1.3601 | 669 |
| 5E | 0.7 | 10 | 48.8 | 1.41 | 1.3621 | 971 |
| 5E | 0.7 | 12 | 45.3 | 1.84 | 1.3643 | 1112 |
| 5E | 0.7 | 14.38 | 44.2 | 2.00 | 1.3649 | 1359 |
| 5F | 0.5 | 8 | 53.9 | .55 | 1.3587 | 222 |
| 5F | 0.5 | 10 | 49.2 | .79 | 1.3618 | 341 |
| 5F | 0.5 | 12 | 45.0 | 1.16 | 1.3648 | 474 |
| 5F | 0.5 | 14 | 41.3 | 1.63 | 1.3671 | 911 |

The linear correlation of yield stress with YSI dextrose and refractive index is shown below for each run.

| | Linear Correlation Between Yield Stress and: | |
|---|---|---|
| Run No. | YSI Dextrose | Refractive Index |
| 5D | 0.999 | 0.977 |
| 5E | 0.988 | 0.985 |
| 5F | 0.979 | 0.920 |
| Compilation | 0.969 | 0.733 |

Thus, it appears that YSI dextrose values correlate much better than refractive index over all three runs and are considerably less dependent on reaction parameters such as acid concentration.

MELTING ONSET TEMPERATURE AS A FUNCTION OF WATER CONTENT

A sample of waxy starch hydrolysate powder was equilibrated with various levels of water and the melting onset temperatures determined using differential scanning calorimetry (substantially as described by White et al., above). The results are reported below.

| Hydrolysate Slurry Water Content, % | Melting Onset Temperature, °C. |
|---|---|
| 60 | 70 |
| 40 | 79 |
| 30 | 132 |
| 20 | 158 |
| 10 | 182 |

It can be seen that at relatively low moisture levels hydrolysate can be quite stable to heat. The actual water content is critical for high temperature stability.

EXAMPLE 9

Hydrochloric Acid Hydrolysis of Waxy Maize Starch

Waxy maize starch was hydrolyzed at 37% solids in 1.0N hydrochloric acid as follows. Deionized water 2,832 g, and 313 g concentrated hydrochloric acid were agitated and heated to 60° C. in a 3-neck, 5 liter, round bottom flask. 2,260 g (2,000 g dry basis at 11.5% moisture) of waxy corn starch was added. The slurry was agitated and heated for 10½ hours, then "b" values were taken every hour after that until optimum "b" value was reached (0.10 "b" value). The "b" values are recorded below:

| Time | Brookfield "b" Value (Average of 4 Readings) |
|---|---|
| 10½ hrs. | 0.46 |
| 11½ hrs. | 0.38 |
| 12½ hrs. | 0.22 |
| 13½ hrs. | 0.07 |

The slurry was harvested at 13½ hours and neutralized to pH about 4.5 with sodium carbonate. The neutralized slurry was centrifuged and then washed by six cycles of resuspension in fresh water and re-centrifuged, after which it had no salty taste. The wet cake was placed on two stainless steel trays and dried overnight in a forced-air oven at about 60° C. The dried product was then ground and passed through a 35 mesh sieve.

EXAMPLE 10

Hydrochloric Acid Hydrolysis of Common Corn Starch

Common (dent) corn starch was hydrolyzed at 35% dry solids in about 1.0N hydrochloric acid as follows.

Into a 12 liter, 3-neck, round bottom tank equipped with constant temperature bath, condenser, stirrer and thermometer, 3,315 g of deionized water and 365.75 g of concentrated 37.2% hydrochloric acid (density 1.0075 g/ml) was placed.

The solution was heated to 65° C. with continuous stirring, then 2,369 g of common corn starch (at about 10% moisture) was added in portions (about 20.0 g) over a period of approximately 25 minutes. The slurry was allowed to react at 65° C. with stirring for 10 hours, then cooled to 25° C. with cold water/ice through a period of 20-25 minutes.

The viscosity of the slurry at 25° C. was measured at 50 and 5 rpm on Brookfield viscometer after $9\frac{1}{2}$ hours and $10\frac{1}{2}$ hours of reaction time. The "b" value at $9\frac{1}{2}$ hours averaged about 0.15 and at $10\frac{1}{2}$ hours averaged about 0.09.

At $10\frac{1}{2}$ hours, the slurry was cooled to 25° C. and a 14% aqueous solution of sodium carbonate was added in portions and pH was constantly monitored until it reached a pH of about 4.5 (total consumption of $Na_2CO_3$ solution about 1,290 ml). The neutralized slurry was then centrifuged and washed three times by resuspension in 7,000 ml of deionized water each time and centrifuged after each resuspension.

After washing, the starch cake was dried at 53°-56° C. in an oven overnight (16 hours).

EXAMPLE 11

Hydrochloric Acid Hydrolysis of Alkaline Washed Waxy Maize Starch

A waxy maize starch was alkaline washed according to the general teachings of U.S. Pat. No. 4,477,480. To a three-necked, 5-liter flasks, 1,200 grams of alkaline washed waxy maize starch (at 9% moisture) was added along with 150 ml of 37% HCl and 1,650 ml of deionized water. The resulting slurry was heated over a steam bath at 60° C. for eight hours, removed from the bath, and placed in an ice bath, which in turn was placed in a refrigerated room overnight. The next day, the slurry was neutralized to a pH of 4.2 with 1M sodium carbonate. The slurry was centrifuged, and the sediment was resuspended in water and centrifuged three more times. The sediment was then dried in a forced-air oven at 48° C. for four days.

EXAMPLE 12

Sulfuric Acid Hydrolyzed Waxy Maize Starch

A waxy maize starch was hydrolyzed in 2.0N sulfuric acid as follows:

Into a 12 liter, round bottom flask equipped with stirrer, thermometer, heating bath and condenser was placed 3,882 g deionized water and 434 g concentrated sulfuric acid (about 2N $H_2SO_4$). This is 13.0% sulfuric acid (100% basis) based on the dry weight of starch to be used. To the acidified water solution, after heating to 60° C., was added 3,692 g (3,200 g dry basis) of waxy maize starch with stirring. The slurry was heated with stirring at 60° C. for 10 hours. After heating for 10 hours, the slurry was cooled to about 50° C. and then the pH was adjusted to 4.0 by adding 14% sodium carbonate solution. The resulting slurry was cooled to about 25° C. with stirring using a cold water bath. The cooled slurry was centrifuged using an International perforated bowl centrifuge at 3,500 rpm (4,000 rpm max. allowed) with a non-woven fine cloth as the filter cloth. There appeared to be no problem in obtaining a good cake buildup and little material escaped into the liquid phase. The wet cake was resuspended in a like amount of water and recentrifuged but this time washed while centrifuging with an equal amount of deionized water. To check the efficiency of washing, a small sample of centrifuged and washed product was slurried with a very small quantity of deionized water, then filtered. The resulting filtrate contained only 0.5% dry substance as estimated from a refractive index, Brix measurement.

The product was dried overnight in a Big Blue-M electric oven at about 48° C. It was weighed (2,227.5 g) then ground using a Wiley mill and 0.5 mm screen. The product had a moisture analysis determined (4.4% moisture) and the yield was calculated to be 66.5% dry basis product.

III. MECHANICAL DISINTEGRATION STUDY USING A HOMOGENIZER

The MICROFLUIDIZER, Model #M-110T, Microfluidics Corporation, is a device which can apply high shear, impact, and cavitation to a slurry of solid material in water. The device consists of a feed reservoir, air pump, pressure module (backpressure module, maximum pressure 8,000 psi or interaction chamber, maximum pressure 16,000 psi) and associated plumbing. The device functions by forcing the slurry through a fixed sized opening contained in the pressure modules under high pressure. The size of the opening will affect the maximum pressure attained and can be changed by changing modules. The pressure is provided by a high pressure, air actuated pump. The working pressure is controlled by varying the air pressure delivered to the pump and/or by changing the module. The actual internal configuration of the modules is a proprietary design and is said to provide a large amount of impact and cavitation as well as shear. To mechanically disintegrate a starch hydrolysate using this device, one simply passes a slurry of starch hydrolysate and water through the device at the desired solids level and appropriate temperature and pressure.

The actual preparation method involves preparation of a starch hydrolysate/water slurry in the proper ratio by adding the appropriate amount of water to the appropriate amount (dry solids basis) of starch hydrolysate to yield a slurry containing the appropriate solids level. The inlet temperature of the slurry is especially critical because it will have a direct bearing on the final temperature reached during dispersion formation. It is best if the water added to the starch hydrolysate is at a temperature equal to the desired inlet temperature. This solution is covered with plastic wrap and equilibrated at the appropriate temperature in a water bath for 2 hours with occasional stirring of the slurry. This allows the solution to attain an equilibrium temperature and fully hydrate all starch particles. The equilibration period is especially critical when preparing samples for analytical measurements.

After the equilibration period, the slurry is passed through the MICROFLUIDIZER equipped with an appropriate pressure module and air pressure source. It is essential that the device be preheated prior to use by passing water at a temperature equal to the desired inlet temperature through the system until the water exiting from the MICROFLUIDIZER has attained an equilibrium temperature. These conditions will yield a consistent product outlet temperature which is dependent on inlet temperature and pressure.

For evaluation of yield stress, the product is extruded into three 2 oz. glass vials and stored at room temperature for 3-4 hours prior to yield stress measurements. The yield stress of the material in each vial is measured in pascals using the test described above. The results of the three measurements are averaged and reported.

A statistically designed study using starch hydrolysate from a single batch was initiated which evaluated the effects of pressure, inlet temperature, outlet temperature and concentration on the yield stress of samples produced by the homogenizer. The first series of experiments using 15%, 20% and 25% concentrations were completed. For these experiments, the pressures used were 8,000 psi and 16,000 psi. Based on the results, a second series of experiments which concentrated on the 5% solids level were conducted. Outlet temperature was measured using a digital thermometer with bimetallic probe. The data from both sets of experiments is shown below in Table 2.

TABLE 2

| Data Point No. | Inlet Temp. (°C.) | Outlet Temp. (°C.) | Pressure (psi) | Dry Solids (wt. %) | Yield Stress (Pascals) |
|---|---|---|---|---|---|
| 1 | 24 | 38.5 | 8,000 | 15 | 125 |
| 2 | 24 | 39.4 | 8,000 | 25 | 977 |
| 3 | 24 | 49.6 | 16,000 | 15 | 258 |
| 4 | 24 | 50.4 | 16,000 | 25 | 1,657 |
| 5 | 41 | 63.2 | 16,000 | 20 | 595 |
| 6 | 41 | 63.1 | 16,000 | 20 | 587 |
| 7 | 41 | 53.0 | 8,000 | 20 | 483 |
| 8 | 41 | 63.0 | 16,000 | 20 | 605 |
| 9 | 41 | 54.0 | 8,000 | 20 | 523 |
| 10 | 41 | 54.0 | 8,000 | 20 | 513 |
| 11 | 59 | 69.5 | 8,000 | 25 | 1,494 |
| 12 | 59 | 68.5 | 8,000 | 15 | 185 |
| 13 | 59 | 68.5 | 8,000 | 15 | 180 |
| 14 | 59 | 77.0 | 16,000 | 25 | 1,033 |
| 15 | 59 | 76.4 | 16,000 | 15 | 19 |
| 16 | 59 | 76.0 | 16,000 | 15 | 19 |

TABLE 2-continued

| Data Point No. | Inlet Temp. (°C.) | Outlet Temp. (°C.) | Pressure (psi) | Dry Solids (wt. %) | Yield Stress (Pascals) |
|---|---|---|---|---|---|
| 17 | 31 | 46.0 | 8,000 | 25 | 1,028 |
| 18 | 31 | 47.5 | 16,000 | 25 | 1,694 |
| 19 | 31 | 50.4 | 12,000 | 25 | 1,457 |
| 20 | 31 | 50.1 | 12,000 | 25 | 1,464 |
| 21 | 41 | 63.0 | 16,000 | 25 | 1,509 |
| 22 | 41 | 53.7 | 8,000 | 25 | 1,199 |
| 23 | 41 | 57.5 | 12,000 | 25 | 1,570 |
| 24 | 41 | 58.3 | 12,000 | 25 | 1,556 |
| 25 | 24 | 44.8 | 12,000 | 25 | 1,362 |
| 26 | 24 | 38.1 | 8,000 | 25 | 892 |
| 27 | 24 | 49.9 | 16,000 | 25 | 1,655 |
| 28 | 24 | 44.9 | 12,000 | 25 | 1,387 |

The actual results shown in Table 2 were used to generate a mathematical model capable of predicting the results of using conditions within the parameters of the study design. The equations which comprise the model are set forth below, where yield stress is in pascals, inlet temperature is in °C., and pressure is in psi.

| | |
|---|---|
| Yield Stress = | $2995.528 - (.009496 * A * B) + (.05773 * B) - (1.0096 * A^2) - (1.02647 * 10^{-5} * B^2)$ |
| Where: | $A = $ (Inlet Temperature - 39.3) |
| | $B = $ (Pressure - 12000) |

PARTICLE SIZE ANALYSIS

A series of starch hydrolysates prepared as in Example 1, above, were suspended in water at 20% solids and subjected to mechanical disintegration by shear in a water-jacketed Waring blender held at about 60° C. The dispersions were then diluted to 5% solids and analyzed for particle size distribution using a model LS-130 particle size analyzer from Coulter Electronics, Inc., Hialeah, Fla. The nature of the starting starch, the time period of mechanical disintegration and the resulting mean particle size by volume-average are shown below in Table 3, and by number-average are shown in Table 4. The particle sizes of the dry powders of starch hydrolysate prior to suspension and mechanical disintegration are also shown for comparison.

TABLE 3

| Sample | PARTICLE SIZE ANALYSIS BY VOLUME | | | | |
|---|---|---|---|---|---|
| | % of Particles of Various Size (by Volume) | | | | |
| Starch Hydrolysate | Shearing (Min.) | 0.1 to 0.5 (Micrometers) | 0.5 to 2.0 (Micrometers) | 0.1 to 3.0 (Micrometers) | Mean (Micrometers) | Median (Micrometers) |
| Common Corn | 8½ | 0 | 4.61 | 9.38 | 14.75 | 11.06 |
| Common Corn | 8½ | .09 | 5.00 | 10.24 | 12.25 | 10.9 |
| Common Corn | 2 | .09 | 4.82 | 9.59 | 12.64 | 11.39 |
| Common Corn | 4 | 0 | 4.50 | 9.12 | 14.45 | 11.32 |
| Waxy Maize | 8½ | .29 | 5.13 | 12.07 | 14.23 | 9.80 |
| High Amylose Corn | 8½ | .59 | 10.17 | 20.63 | 7.99 | 7.38 |
| High Amylose, Powder | — | .40 | 4.85 | 10.13 | 19.60 | 17.88 |
| Common Corn, Powder | — | .09 | 5.98 | 9.13 | — | — |
| Waxy Maize, Powder | — | .01 | 4.41 | 6.05 | 32.97 | 32.80 |

TABLE 4

| Sample | PARTICLE SIZE ANALYSIS BY NUMBER | | | |
|---|---|---|---|---|
| | % of Particles of Various Size (by Number) | | | |
| Starch Hydrolysate | Shearing (Min.) | 0.1 to 0.5 (Micrometers) | 0.5 to 2.0 (Micrometers) | 2.0 to 3.0 (Micrometers) | <0.1 to 3.0 (Micrometers) |
| Common Corn | 8½ | 31.9 | 53.4 | 8.1 | 93.4 |
| Common Corn | 8½ | 89.6 | 8.3 | 1.2 | 99.1 |
| Common Corn | 2 | 83.3 | 13.8 | 1.7 | 98.8 |

TABLE 4-continued

| Sample | PARTICLE SIZE ANALYSIS BY NUMBER | | | | |
|---|---|---|---|---|---|
| | | % of Particles of Various Size (by Number) | | | |
| Starch Hydrolysate | Shearing (Min.) | 0.1 to 0.5 (Micrometers) | 0.5 to 2.0 (Micrometers) | 2.0 to 3.0 (Micrometers) | <0.1 to 3.0 (Micrometers) |
| Common Corn | 4 | 8.9 | 73.4 | 9.9 | 92.2 |
| Waxy Maize | 8½ | 90.7 | 7.6 | 1.0 | 99.3 |
| High Amylose Corn | 8½ | 92.5 | 6.5 | 0.6 | 99.6 |
| High Amylose, Powder | — | 96.0 | 3.4 | 0.4 | 99.8 |
| Common Corn, Powder | — | 66.6 | 31.3 | 1.5 | 99.4 |
| Waxy Maize, Powder | — | 3.9 | 91.8 | 3.2 | 98.9 |

SEPARATION PROCESSES

Laboratory Centrifugation of Starch Hydrolysate

Series 1

A sample of neutralized starch hydrolysate was obtained from Run No. 2D. A number of centrifuge bottles were filled to about 90% full with the neutralized slurry and the quantity of all bottles was finely adjusted so that each one weighed the same. One at a time, the bottles of neutralized slurry were centrifuged using the Sorvall GSA head at about 15° C. for varying amounts of time and at varying rpm to estimate the relative centrifugal force (RCF) needed to give good separation of the solid and liquid phases. "Good separation" was subjectively determined by slowly inverting the centrifuged bottle. If some solids were mobile enough to decant with the liquid, then the separation was judged to be incomplete ("I"). If no or nearly no solids decanted with the liquid, then the separation was judged to be complete ("C"). Centrifugation studies were also done in a like manner using instead of neutralized slurry, the unneutralized, acidic slurry from the same run. The results are shown immediately following.

SERIES 1 CENTRIFUGATION

| | | Separation at Various Centrifuge Times | | |
|---|---|---|---|---|
| rpm | RCF × g | 15 min. | 5 min. | 2 min. |
| Neutralized Slurry: | | | | |
| 2,000 | 653 | I | — | — |
| 3,000 | 1,469 | I | — | — |
| 4,000 | 2,611 | C | — | — |
| 5,000 | 4,080 | C | I | — |
| 6,000 | 5,875 | — | I | — |
| 7,000 | 7,996 | — | C | I |
| 8,000 | 10,444 | — | C | C |
| 9,000 | 13,218 | — | — | C |
| 10,000 | 16,319 | — | — | C |
| 11,000 | 19,745 | — | — | — |
| Acidic Slurry (Unneutralized): | | | | |
| 9,000 | 13,218 | — | I | — |
| 10,000 | 16,319 | — | C | I |
| 11,000 | 19,745 | — | — | I |

Lab Centrifugation Series 2

Samples of neutralized slurry were obtained during the Run No. 5A and subsamples of each were subjected to centrifugation at various speeds using a Sorvall centrifuge (with GSA head). The time needed to accelerate up to speed (from 1,000 rpm) and to stop (down to 1,000 rpm) was measured and recorded. After centrifugation, the samples were slowly decanted and the liquid portion drained off. If no solids poured off with the liquid, then the separation was judged to be complete. If some solids was mobile enough to be poured off with the liquid, then the separation was judged to be incomplete. The weight of sample remaining after decanting was called the decanted weight of sediment and was recorded. In each case, 238 g of sample was used to start. The results are shown immediately following.

(The asterisk below indicates that it was clear that at lower RCF, the separation of this sample would be incomplete.)

| | Centrifugation Conditions (held 2 min @ rpm specified) | | | | | |
|---|---|---|---|---|---|---|
| Sample | rpm | RCF × g | Acceleration Time (sec.) | Stopping Time (sec.) | Separation | Decanted Weight of Sediment, (g) |
| 6 hr | 8,000 | 10,400 | 103 | 366 | C | 125 |
| 7 hr | 8,000 | 10,400 | 103 | 366 | C | 122 |
| 8 hr | 8,000 | 10,400 | 103 | 366 | C | 121 |
| Final | 8,000 | 10,400 | 103 | 366 | C | 119 |
| 6 hr | 7,000 | 7,996 | 83 | 348 | C | 123 |
| 7 hr | 7,000 | 7,996 | 83 | 348 | C | 127 |
| 8 hr | 7,000 | 7,996 | 83 | 348 | C | 133 |
| Final | 7,000 | 7,996 | 83 | 348 | C | 127 |
| 6 hr | 6,000 | 5,875 | 63 | 285 | C | 130 |
| 7 hr | 6,000 | 5,875 | 63 | 285 | C | 132 |
| 8 hr | 6,000 | 5,875 | 63 | 285 | C | 139 |
| Final | 6,000 | 5,875 | 63 | 285 | C | 136 |
| 6 hr | 5,000 | 4,080 | 51 | 260 | C* | 137 |
| 7 hr | 5,000 | 4,080 | 51 | 260 | I | 134 |
| 8 hr | 5,000 | 4,080 | 51 | 260 | I | 134 |
| Final | 5,000 | 4,080 | 51 | 260 | I | 131 |

Lab Centrifugation Series 3

Neutralized starch hydrolysate samples were obtained at various hydrolysis time periods from starting solids in acidic slurry.

The neutralized slurries were subjected to centrifugation at 2,000, 3,000 and 4,000 rpm and the samples were carefully inverted. If some insoluble solids were poured off with the liquid, then the separation was judged to be incomplete. If no insoluble solids were poured off, then the separation was judged to be complete. If the separation was incomplete, then the total weight of liquid material decanted was weighed and recorded. The weight of initial alkaline slurry used was 238 g for each slurry. After decanting, the quantity of insoluble solids decanted was measured after repeated washing to remove all soluble solids. The results are shown immediately following.

| Hydrolysis Time (hr.) | Centrifuging Conditions | | | Separation | Decanted Weight (g) | Insoluble Solids in Decantate | |
|---|---|---|---|---|---|---|---|
| | rpm | Time @ rpm (min.) | RCF | | | (g, db) | % of Total |
| 4 | 3,000 | 2 | 1,469 | I | 123 | .44 | 1.3 |
| 5 | 3,000 | 2 | 1,469 | I | 126 | .24 | 0.8 |
| 6 | 3,000 | 2 | 1,469 | I | 126 | .27 | 1.0 |
| 7 | 3,000 | 2 | 1,469 | I | 125 | .36 | 1.4 |
| 8 | 3,000 | 2 | 1,469 | I | 125 | .54 | 2.3 |
| Final | 3,000 | 2 | 1,469 | I | 104 | 4.90 | 21.9 |

-continued

| Hydro-lysis Time (hr.) | Centrifuging Conditions | | | Separation | Decanted Weight (g) | Insoluble Solids in Decantate | |
|---|---|---|---|---|---|---|---|
| | rpm | rpm (min.) | RCF | | | (g, db) | % of Total |
| (11) | | | | | | | |
| 4 | 4,000 | 2 | 2,611 | I | 122 | .30 | 0.9 |
| 5 | 4,000 | 2 | 2,611 | I | 124 | .18 | 0.6 |
| 6 | 4,000 | 2 | 2,611 | I | 123 | .13 | 0.5 |
| 7 | 4,000 | 2 | 2,611 | I | 123 | .18 | 0.7 |
| 8 | 4,000 | 2 | 2,611 | I | 123 | .28 | 1.2 |
| Final (11) | 4,000 | 2 | 2,611 | I | 103 | 5.26 | 23.5 |
| 4 | 2,000 | 15 | 653 | C | 125 | 0 | 0 |
| 5 | 2,000 | 15 | 653 | C | 126 | 0 | 0 |
| 6 | 2,000 | - 15 | 653 | C | 126 | 0 | 0 |
| 7 | 2,000 | 15 | 653 | I | 127 | 0.08 | 0.3 |
| 8 | 2,000 | 15 | 653 | I | 129 | .04 | 0.2 |
| Final (11) | 2,000 | 15 | 653 | I | 111 | 3.14 | 14.2 |
| 4 | 3,000 | 15 | 1,469 | C | 122 | 0 | 0 |
| 5 | 3,000 | 15 | 1,469 | C | 122 | 0 | 0 |
| 6 | 3,000 | 15 | 1,469 | C | 121 | 0 | 0 |
| 7 | 3,000 | 15 | 1,469 | C | 122 | 0 | 0 |
| 8 | 3,000 | 15 | 1,469 | C | 122 | 0 | 0 |
| Final (11) | 3,000 | 15 | 1,469 | I | 112 | 2.56 | 11.4 |
| Final (11) | 4,000 | 15 | 2,611 | I | 118 | 2.20 | 9.8 |
| Final (11) | 4,000 | 30 | 2,611 | C | 134 | 0 | 0 |

Separation Scale-up

The recovery of the granular starch hydrolysates from the slurry following neutralization is quite difficult. Extensive acid hydrolysis in the reaction step makes the residual starch granules susceptible to breakage which produces particles in the submicron range. In fact, a portion of the starch is hydrolyzed completely to dextrose, thus, there are a tremendous number of submicron particles in a phase. These submicron particles, along with insoluble particles in the 1–5 micron range, make filtration of the slurry poor at best. Further, the densities of the separable fractions are almost identical and the insoluble starch particles are flocculent in nature, making gravity separation almost impossible. These conditions make separation with traditional techniques very difficult.

FILTRATION TECHNIQUES

A number of filtration techniques were attempted. Laboratory experiments demonstrated that granular starch hydrolysates filter poorly under vacuum. Filtration experiments using pilot scale equipment proved equally fruitless. The results of those experiments are summarized below. The slurry utilized in the experiments was prepared by hydrolyzing a waxy maize starch with 0.5N HCl at 35% d.s. The slurry was neutralized with a sufficient amount of 50% NaOH.

Plate and Frame Filter Press: Filtration on a 24" plate and frame filter press was attempted. (25" Poly Press Plate and Frame Filter, 24" Frames from T. Shiver & Co., Harrison, N.J.) Twenty of the plates were clothed with a dense weave, heavy cotton cloth folded over filter paper (three layers total). Initially, the slurry seemed to filter well with minimal product loss to the filtrate. However, after only 15 minutes of feeding, the pump reached 60 psi and the surface area became totally blinded as filtration stopped. When the press was disassembled, a sloppy, 20% d.s., ¼" cake was found covering each cloth.

Tube Filter Press: The Alfa-Dyne High Pressure Tube Filter Press (Aerodyne Development Corporation, Cleveland, Ohio) was tested. The slurry did not filter well on this device. Initially, the filtration rates through the 0.5 CFM screen were very slow. As pressure was increased to over 300 psi, it was noticed that the slurry began to bleed through the filter. At about 1000 psi, total breakthrough occurred.

Horizontal Vacuum Belt Filtration: A 1.0 m² horizontal vacuum belt filtration unit was tested. (Rigidbelt Horizontal Filtration Unit from Dorr-Oliver, Inc., Stamford, Conn.) The following table summarizes the conditions and results.

| VACUUM BELT FILTRATION TEST RESULTS | | | | | | | | |
|---|---|---|---|---|---|---|---|---|
| Run No. | Pass No. | Belt Cloth | Belt Speed (Setting) | Feed Rate (gpm) | Average Vacuum (Bar) | Cake Moisture (%) | Filtration Rate (lb/ft²/hr) | Insoluble Solids Losses (%) |
| 4A | 1 | 5–10 CFM Nylon | 1 | 0.16 | 0.64 | 60.0 | 15.2 | 45 |
| 4B | 1 | 5–10 CFM Nylon w/ Backing | 5 | 0.29 | 0.59 | 60.3 | 14.5 | 33 |
| 4C | 2 | 3 CFM Polyester | 6 | 0.26 | 0.62 | 71.0 | 17.4 | 61 |
| 4C | 3 | 35 CFM Polyester | 6.5 | 0.28 | 0.54 | 76.3 | 6.8 | 0 |
| 4C | 4 | 35 CFM Polyester | 3.5 | 0.18 | 0.65 | — | 18.0 | 87 |
| 4D | 1 | 10 CFM Mono-Multi | 7.5 | 0.15 | 0.55 | 59.8 | 19.6 | 25 |
| 4D | 2 | 10 CFM Mono-Multi | 5.5 | 0.61 | 0.65 | 70.0 | 20.0 | 56 |
| 4D | 3 | 10 CFM Mono-Multi | 5.0 | 0.42 | 0.65 | 78.2 | 20.0 | 47 |
| 4D | 4 | 10 CFM Mono-Multi | 5.5 | 0.53 | 0.66 | 82.8 | 26.3 | 79 |

Although the results were inconsistent, in general, higher filtration rates resulted in higher losses. The lab filtration rate of 1–3 lb/ft²/hr was not approached. The third wash pass of Lot No. E27 was closest at 6.8 lb/ft²/hr and losses from this pass were not detectable. This indicates that if a set of conditions could be found which resulted in low filtration rates, acceptable losses may be possible. Lower filtration rates, however, would result in higher retention of the mother liquor and more wash passes.

The cake moistures indicated above were dependent on which part of the cake was sampled. Throughout most of the tests, a small stream of mother liquor constantly ran off the end of the belt making the top layer very wet (an average cake moisture of 72.7% was used for calculations). The problem of not being able to dewater the cake well forced as many as four wash passes to reduce the ash to an acceptable level. The large volume of side stream generated by the multiple washes is commercially unattractive.

Larox Filtration: A 1 ft$^2$ Larox PF2.5 pressure Automatic Pressure Filter unit was tested. (Larox, Inc., Columbia, Md.) Filtration rates were very poor (1.0 lb/ft$^2$/hr) and losses to the filtrate were unacceptably high (23–37%).

CENTRIFUGATION TECHNIQUES

Using a slurry prepared as described above, several pilot scale centrifugation techniques were tested. The results are summarized below.

Perforated Basket Centrifuge: A 12" perforated basket centrifuge (Western States Machine Co., Hamilton, Ohio) was tested. Recoveries were very low as material either passed through the various cloths or blinded them off, stopping filtration altogether.

Stacked Disk, Nozzle Discharge Centrifuge: Testing was done on a Model C-9 Merco (Dorr-Oliver, Inc., Stamford, Conn.). This unit is capable of centrifugal forces as high as 9600 g. Many different operating conditions were tried in an attempt to minimize the loss of insoluble solids to the overflow stream. The most significant of these tests are summarized below.

| Run No. | Pass No. | Avg. Feed (lb/min) | Avg. Wash (gpm) | Feed Solids (%) | Centrifugal Force (g) | Nozzle Size (No.) | Final Ash (%) | Insoluble Solids Losses (%) |
|---|---|---|---|---|---|---|---|---|
| 1C | 1 | 7.9 | 3.8 | 7.2 | 9600 | 56 | 4.43 | 37 |
| 1D | 1 | 10.5 | 4.0 | 7.1 | 9600 | 56 | 2.28 | 31 |
| 3A | 1 | 5.6 | 4.2 | 4.6 | 9600 | 65 | 8.22 | 82 |
| 3B | 1 | 5.8 | 3.3 | 5.7 | 6300 | 60,65 | 2.36 | 61 |
| 3C | 1 | 6.9 | 3.6 | 2.8 | 6300 | 65 | 0.96 | 76 |
| 1F | 1 | 5.4 | 1.7 | 11.5 | 9600 | 53 | — | 10 |
| 1F | 2 | 9.7 | 1.1 | 7.9 | 9600 | 53 | — | 1 |
| 1F | 3 | 21.0 | 2.3 | 5.5 | 9600 | 53 | 3.55 | 43 |

In the test work, it was found that even without putting wash water to the machine, the solids in the overflow stream were unacceptably high. This indicates that something was interfering with the separation.

The best overall recovery obtained on this apparatus was 69% for Run No. 1D. Even at the highest g-forces, high product losses to the overflow stream was a problem regardless of nozzle size or wash water rate. Not only were the recoveries as a whole disappointing, but because the material did not concentrate well, tremendous hydraulic loads were necessary to wash the salt down to an acceptable ash level. The large volume of side stream generated from this technique, coupled with the unacceptably high product losses, eliminated it from serious consideration as the equipment of choice for this separation.

Peeler Centrifuge: A small peeler centrifuge (Model HZ225, 10" Peeler Centrifuge from Krauss Maffei Corp., Florence, Ky.). This unit is a perforated basket centrifuge, on a horizontal axis, with a skimmer and plough attachment. The results were not acceptable. After several recycle additions, a thin cake formed but wash water would not penetrate the surface. After a few minutes of spinning, the cake cracked and the wash simply flushed through. Another problem was found when the ploughing step was attempted. The starch hydrolysate cake plugged the removal chute apparently because the wet cake is very sticky in nature.

Horizontal Decanter Centrifuge: Tests were conducted on the Model 660 Sharples Super-D-Canter centrifuge (Alfa-Laval Separation, Inc., Sharples Division, Oak Brook, Ill.). In theory, this horizontal decanter design is capable of separating difficult sludges by using relatively high g-forces and residence times as long as two minutes. Pilot plant test results on the horizontal decanter are summarized below.

| Run No. | Pass No. | Average Feed (lb/min) | Back Drive (Setting) | Cake Solids (%) | Centrate Solids (%) | Insoluble Solids Losses (%) |
|---|---|---|---|---|---|---|
| 1A | 1 | 10.7 | 1 | 36.2 | 1.9 | 24 |
| 1A | 2 | 8.3 | 1 | 31.8 | 2.5 | 23 |
| 1B | 3 | 5.6 | 1 | 31.8 | 2.9 | 35 |
| 1B | 1 | 14.0 | 1 | 36.1 | 3.9 | 73 |
| 1B | 2 | 8.3 | 5 | 29.3 | 1.6 | 25 |
| 6A | 1 | 3.3 | 1 | 34.5 | 4.8 | 78 |

Overall, the product did not separate well on this machine.

Stacked Disk, Split Bowl Centrifuge: Only one attempt was made to separate this material on a 5" Westfalia split bowl centrifuge (Centrico, Inc., Northvale, N.J.). The results were very poor. Even at the highest rotational speed (equivalent to 1080 g), no separation of the product was seen.

Solid Bowl, Batch Centrifuge: A 14" Solid Bowl S.T.M. 100-146 Lab Unit Centrifuge (Western States Machine Company, Hamilton, Ohio) was tested. Although too small for a plough and bottom discharge features, many tests, including interim production runs, were made on this machine. The most significant test results are summarized in the table below.

| Test No. | Run No. | Pass No. | Bowl Speed (rpm) | Feed Rate | Spin Time (min) | Cake Solids (%) | % I.S. Loss to Centrate | % S.S. Loss to Centrate |
|---|---|---|---|---|---|---|---|---|
| 1 | 5B | 1 | 2250 | 0.25 gpm | 5 | 34.5 | 1.5 | 69.6 |
| 2 | 5B | 1 | 2253 | 0.20 gpm | 5 | 35.7 | 1.4 | 69.0 |
| 3 | 5B | 1 | 2882 | 0.25 gpm | 5 | 34.6 | 2.1 | 71.5 |
| 4 | 5B | 1 | 3190 | 0.25 gpm | 5 | 37.6 | 2.4 | 73.8 |
| 5 | 5B | 1 | 3499 | 0.25 gpm | 5 | 36.5 | 0.6 | 72.7 |
| 6 | 5B | 1 | 3500 | 0.20 gpm | 5 | 36.4 | 0 | 72.7 |

-continued

SOLID BOWL CENTRIFUGE SUMMARY

| Test No. | Run No. | Pass No. | Bowl Speed (rpm) | Feed Rate | Spin Time (min) | Cake Solids (%) | % I.S. Loss to Centrate | % S.S. Loss to Centrate |
|---|---|---|---|---|---|---|---|---|
| 1 | 5E | 1 | 3720 | 0.28 gpm | 5 | 36.2 | 0 | 57.6 |
| 2 | 5E | 1 | 3720 | 0.38 gpm | 5 | 35.2 | 2.6 | 61.4 |
| 3 | 5E | 1 | 3720 | 0.68 gpm | 5 | 37.0 | 7.0 | 67.7 |
| 4 | 5E | 1 | 3550 | 500 psi | 5 | — | 11.9 | 68.4 |
| 5 | 5E | 1 | 3550 | 500 psi | 5 | — | 17.0 | 69.5 |
| 6 | 5E | 1 | 3550 | 100 psi | 6 | — | 14.0 | 69.1 |
| 7 | 5E | 1 | 3722 | 100 psi | 5 | 38.9 | 7.9 | 61.3 |
| 8 | 5F | 1 | 3585 | 0.29 gpm | 5 | 38.8 | 4.3 | 54.0 |
| 9 | 5F | 1 | 3585 | 100 psi | 5 | 39.2 | 8.5 | 56.0 |
| 10 | 5F | 1 | 3585 | 41 lbs | 5 | 39.0 | 5.4 | 53.2 |
| 11 | 5F | 1 | 3585 | 46 lbs | 5 | 40.5 | 14.7 | 56.4 |
| 12 | 5F | 1 | 3585 | 0.29 gpm | 5 | 38.4 | 1.6 | 51.7 |
| 1 | 6B | 1 | 2557 | 19 lbs | 5 | 33.3 | 1.8 | 51.7 |
| 2 | 6B | 1 | 2557 | 18 lbs | 15 | 33.3 | 0 | 53.2 |
| 3 | 6B | 1 | 3500 | 18 lbs | 7 | 34.4 | 0 | 52.4 |
| 4 | 6B | 1 | 3510 | 18 lbs | 7 | 36.8 | 1.8 | 60.0 |
| 5 | 6B | 2 | 3508 | 18 lbs | 7 | 25.6 | 0.7 | 81.8 |
| 1 | 6D | 2 | 3530 | 0.32 gpm | 5 | 26.3 | 3.0 | 74.9 |
| 2 | 6D | 2 | 3563 | 0.32 gpm | 5 | 20.7 | 6.2 | 84.0 |
| 3 | 6D | 2 | 3559 | 0.32 gpm | 5 | 25.6 | 23.2 | 87.4 |
| 4 | 6D | 2 | 3556 | 0.32 gpm | 6 | 19.8 | 8.4 | 90.0 |
| 6 | 6D | 2 | 3560 | 0.32 gpm | 5 | 15.6 | 34.1 | 90.3 |
| 1 | 6F | 1 | 3540 | 0.30 gpm | 3 | 34.5 | 1.1 | 73.6 |
| 2 | 6F | 1 | 3539 | 0.29 gpm | 3 | 33.4 | 2.3 | 64.3 |
| 3 | 6F | 1 | 3539 | 0.29 gpm | 3 | 35.1 | — | — |
| 4 | 6F | 1 | 3542 | 18 lbs | 3 | 33.4 | — | — |

All tests listed were run with first pass slurry material except Run No. 6B, test 5, and all 6D tests which were run with second pass slurry. In Run Nos. 5E and 5F, tests 4–7 and 9 were done with a high pressure feed pump at pressures of 100–500 psi through a Spraying Systems No. 0004 solid stream tip nozzle (Spraying Systems Co., Wheaton, Ill.).

Results from Run Nos. 5B, 6B and 6F represent some of the best conditions for separating this slurry. Losses of insoluble solids to the filtrate stream average 1% to 2% with low feed rates (around 0.25 gpm) and 3 to 5 minutes spin time. Although it was possible on some runs to get acceptably low losses at only 2250 to 2550 rpms (1000–1300 g), cake moistures as a whole were higher, forcing more wash passes to reduce the salt content in the product.

Tests with Run Nos. 5E and 5F were done to evaluate the potential advantages from an accelerated feed system. No advantages were found; losses were higher even at equivalent feed rates.

Individual data points in this series also point out that two different lots of granular starch hydrolysate centrifuged under similar conditions will not necessarily separate the same. Test 8 was supposed to be a repeat of test 1, but the results were significantly different; 4.3% of the insoluble fraction was lost to the centrifugate as opposed to almost none in test 1. Particle sensitivity to shear and differences in the soluble to insoluble solids ratio is suspected as the reason for this variance; however, these effects have not yet been quantified.

Tests 2, 4 and 6 with Run No. 6D were conducted to test a bowl without baffles. In general, losses with this bowl were significantly higher. There were also problems with balance of the machine with the baffleless bowl; it was very unstable when not decanting.

The losses seen were highly dependent on variables that should be more easily controlled on an automated production unit. For instance, it was found in some of the later tests that the distance the skim tube was drawn into the filtrate layer had a tremendous effect on the overall losses and the apparent cake moistures. Additional tests on a larger, semi-automated machine are necessary before setting specific design criteria for the production units.

Overall, at centrifugal forces greater than 2000 g, the solid bowl batch centrifuge design adequately separates granular starch hydrolysate product from the mother liquor. Losses as low as 2% insoluble solids have been consistently attainable under low flow rates and long retention times. In addition, because the cake can be dewatered to 35% to 40% d.s., this option requires the least amount of water to remove the salt fraction. At traditional g-forces of 1300, cake solids of 30% to 35% should be expected and losses of 3% to 10% may be unavoidable.

A comparison of the overall efficiency of the most competitive separation techniques is found in the following table.

TABLE 5
COMPARISON OF SEPARATION TECHNIQUES

| Equipment | Cake Solids (%) | No. of Passes | Hydraulic Load (lb Waste/ lb Product) | Overall I.S. Losses (%) |
|---|---|---|---|---|
| Belt Filter | 27.3 | 2 | 20.5 | 51.2 |
| Merco | 7.3 | 2 | 16.4 | 37.8 |
| Sharples | 33.3 | 1 | 11.9 | 25.0 |
| Solid Bowl | 35.0 | 1 | 7.5 | 2.0 |
| Microfiltration | 26.0 | — | — | 0 |

Clearly the solid bowl batch centrifugation is superior to the other options. The losses obtained are acceptable on a commercial scale and hydraulic load of side stream is the lowest of all methods tested.

For best results, the neutralized starch hydrolysate is diluted prior to centrifugation. Preferably, it is cooled below about 38° C. and diluted to approximately 7% insoluble solids for centrifugation. The dilution is calculated so that 2% ash in the cake is achieved in only one wash pass. Certain end use applications may require additional wash passes to remove soluble solids even though the ash target is met.

It has been found to be particularly advantageous (in terms of obtaining a desirably bland flavor for the hydrolysate) if the neutralization of the slurry is only partially carried out prior to separation. Preferably, the slurry will be neutralized to a weakly acidic pH (e.g., from about 1.5 to about 3.5 and preferably from about 2 to about 3) prior to isolation. To avoid flavor and color pickup, pH values of 8 and above are to be avoided. Subsequent to separation and washing, the pH is adjusted to between about 4 to 5 prior to spray drying.

Due to the susceptibility of granular starch hydrolysate residues to physical fragmentation, the separation of the starch hydrolysate residue from the mother liquor must be controlled to prevent fragmentation of the residue. Although some fragmentation may occur during separation, solid or imperforate bowl centrifuges of the type previously discussed allow separation while avoiding fragmentation of a substantial portion of the granular starch hydrolysate residue.

This separation is effected by introducing a slurry of the granular starch hydrolysate residue into an imperforate bowl centrifuge. The centrifuge is operated at a sufficiently high velocity to sediment at least a majority, by weight, of the starch hydrolysate residue from the liquid phase and while doing so to create insufficient shear to physically fragment a substantial portion, by weight, of the starch hydrolysate residue which would make separation in said centrifuge impractical.

ALCOHOL FILTRATION

Series 1, AF Run Nos. 1 and 2

A sample (1,800 gms) of neutralized granular waxy starch hydrolysate slurry from Run No. 6A was diluted with ethanol (95% in water) to a 50/50 and a 75/25 weight ratio of alcohol to water. The slurries were then filtered (on a Buchner funnel with 9 cm Whatman No. 1 filter paper and an aspirated vacuum flask) and filtration time, % yield (based on starch dry solids), and yield stress were compared.

Series 2, AF Run Nos. 3–5

Another series of alcohol filtrations were performed as in Series 1, but employing neutralized slurry from Run No. 6E and dilution to 60/40, 70/30 and 75/25 for each of three separate samples, respectively. The results for AF Run Nos. 1–5 are shown in Table Z, immediately following.

TABLE Z

| Alcohol Filtration Run No. | Alcohol/ Water Ratio | Filter Time (sec.) | % Yield | % Ash | Mw | Haake Yield Stress (Pa) at d.s. | | |
|---|---|---|---|---|---|---|---|---|
| | | | | | | 20% | 25% | 30% |
| 1 | 50/50 | 4860 | 31.4 | 0.35 | 5613 | 641 | — | — |
| 2 | 75/25 | 120 | 52.8 | 0.42 | 4299 | 223 | — | — |
| 3 | 75/25 | 95 | 71 | 1.09 | 3701 | 147 | 485 | 504 |
| 4 | 70/30 | 180 | 61.7 | 0.71 | 4103 | 191 | 369 | 587 |
| 5 | 60/40 | 990 | 52.8 | 1.18 | 4493 | 299 | 574 | — |

In Series 1, at the 75/25 ratio, filtration time was very fast and yield was slightly improved compared to the 50/50 ratio. The yield stress was much lower, however. This may be due to increased amount of lower DP oligosaccharides and/or salt. A higher solids salve would have to be used to offset this, which may eliminate any advantage of filtration time or increased yield.

In Series 2, it was found that at an alcohol/water weight ratio of 60/40 or higher, filtration rates and yields were improved. However, product yield stress, after microfluidization, increased more or less in inverse proportion to the yield increase. For example, in the Series 2, 75/25 ratio experiment, a 71% yield of insolubles was obtained compared to 45–50% typically obtained by separation from the aqueous slurry. This sample had a low yield stress at 20% solids, but increased to about 504 Pa at 30% solids which is comparable to the yield stress of the hydrolysate from aqueous separation at 20% solids. Hence, the increased yield is offset by the need to increase solids to achieve an equal yield stress compared to normal aqueous hydrolysate.

MICROFILTRATION OF NEUTRALIZED SLURRY OF STARCH HYDROLYSATE

The use of a microfiltration unit (Millipore Corporation) to isolate the insoluble starch hydrolysate residue was examined in a series of microfiltration runs. The slurry used was from Run No. 7, taken from the batch after neutralization.

The runs were made on small test unit with a cartridge having a single ceramic element, with 12 "lumens" (or channels), each lumen being 4 mm in diameter and having a membrane layer (with 0.2 micron pores) (1.4 ft$^2$ total membrane surface area). A larger scale unit may have 2 cartridges, each having 1 element, each element having 6–12 lumens (each lumen 6 mm in diameter). The purpose of the tests was to investigate microfiltration as an option for separating the insoluble hydrolysate solids from the salt and soluble solids fractions. The primary concern was the viscosity of the slurry and how it would affect both fouling and the ability to concentrate after diafiltration. Three tests were conducted.

In the first run, flux rates were determined at three inlet pressures before concentrating the slurry from 24.5% to 26.4% total solids. Flux rates ranged from 23 to 43 gal/ft$^2$/day before concentration. (To convert from 1/m$^2$/hr to gal/ft$^2$/day, divide by 1.7.) As the insoluble solids to soluble solids ratio increased, flux rates dropped off to 15.2 gal/ft$^2$/day (with 32 psi back pressure on the element). It is not clear at this time whether the drop in flux was due to an increase in slurry viscosity or fouling of the membrane after the 4.4 hours run time.

In the second run, the ash content in the slurry was reduced from 4.81% to 0.5% via diafiltration. Total solids in the feed dropped from 24.5% to 18.5% as the solubles were removed. It is interesting to note that flux rates were much higher during this test (primarily due to higher cross flow rates and lower solids). In the two hours run time of this test, no apparent fouling occurred.

The third run was a combination of concentration and diafiltration steps. First, the slurry was concentrated from 24.5% to 28.2% total solids by removing the permeate stream at flux rates of 36 to 125 gal/ft$^2$/day (flux rates dropped steadily as the stream was concentrated). Then the material was diafiltered, reducing the ash from 3.81% to 2.44% in only 1.6 hours. Flux rates seemed to improve slightly with diafiltration.

Overall, the run results were positive. Flux rates observed were very reasonable. We were able to concentrate the slurry to fairly high viscosities, and the membrane cleaned easily when fouled.

MICROFILTRATION RESULTS

| Microfiltration Run No. | Run Time (min) | Inlet Pressure (psig) | Outlet Pressure (psig) | Fresh Water (liter) | Permeate Volume (liter) | Permeate Rate (ml/min) | Cross Flow (gpm) | Flux Rate (l/m²/hr) |
|---|---|---|---|---|---|---|---|---|
| MF1 | 45 | 11 | 0 | 0 | 0 | 110 | 7.4 | 50.8 |
| | 61 | 22 | 11 | 0 | 0 | 120 | 7.7 | 55.4 |
| | 113 | 50 | 38 | 0 | 0 | 160 | 7.8 | 73.8 |
| | 154 | 49 | 37 | 0 | 0 | 85 | 7.8 | 39.2 |
| | 172 | 40 | 30 | 0 | 0 | 90 | 8.0 | 41.5 |
| | 200 | 42 | 30 | 0 | 2.0 | 66 | 7.7 | 30.5 |
| | 240 | 42 | 30 | 0 | 4.6 | 63 | 7.6 | 29.1 |
| | 266 | 44 | 32 | 0 | 6.2 | 56 | 7.6 | 25.8 |
| MF2 | 9 | 39 | 6 | 2.0 | 1.0 | 200 | 15.4 | 92.3 |
| | 24 | 40 | 6 | 5.0 | 4.0 | 212 | 15.6 | 97.8 |
| | 46 | 42 | 8 | 11.0 | 10.0 | 317 | 17.5 | 146.3 |
| | 61 | 43 | 8 | 16.0 | 15.0 | 356 | 17.9 | 164.3 |
| | 101 | 40 | 8 | 30.0 | 29.0 | 322 | 17.5 | 148.6 |
| | 119 | 40 | 8 | 36.0 | 35.0 | 336 | 17.7 | 155.1 |
| | 134 | 40 | 8 | 41.0 | 40.0 | 357 | 16.8 | 164.8 |
| MF3 | 2 | 42 | 4 | 0 | 1.0 | 461 | 16.8 | 212.8 |
| | 10 | 42 | 4 | 0 | 4.0 | 356 | 16.7 | 164.3 |
| | 21 | 44 | 5 | 0 | 8.0 | 345 | 16.9 | 159.2 |
| | 31 | 44 | 6 | 0 | 11.0 | 257 | 17.0 | 118.6 |
| | 43 | 44 | 7 | 0 | 11.5 | 132 | 17.8 | 60.9 |
| | 44 | 40 | 7 | 1.0 | 11.5 | — | 17.6 | — |
| | 64 | 42 | 5 | 5.0 | 13.5 | 91 | 17.0 | 42.0 |
| | 83 | 40 | 5 | 8.0 | 15.5 | 101 | 16.7 | 46.6 |
| | 93 | 40 | 5 | 10.0 | 17.5 | 153 | 16.8 | 70.6 |
| | 105 | 40 | 5 | 12.0 | 19.5 | 156 | 16.8 | 72.0 |
| | 127 | 38 | 5 | 15.0 | 22.5 | 147 | 16.6 | 67.8 |
| | 141 | 38 | 5 | 17.0 | 24.5 | 144 | 16.2 | 66.4 |

IV. GRANULAR STARCH HYDROLYSATE INTERACTION WITH CO-INGREDIENT

The utility of granular starch hydrolysates depends on the development of a fat-like character when sheared (fragmented) in aqueous compositions. Retention of that fat-like character during additional processing or storage is important and expands the utility of the granular starch hydrolysate. For example, dairy products are typically processed at a minimum of 72° C. and more commonly at 85° C. Additives that interact with the starch hydrolysate or otherwise aid in the retention of its fat-like character make possible utilization in this area. Similar benefits would be found with additives that aid in preserving the fat-like character following freezing.

Certain ingredients have been found to interact with the granular starch hydrolysates previously described to yield compositions with superior properties. Carbohydrate saccharides interact favorably with granular starch hydrolysate to yield superior compositions that retain their fat-like character following either heating or freezing. Emulsifiers interact with granular starch hydrolysates to yield composition with improved retention of fat-like character following heating. Relatively low levels of salt provide enhanced fat-like character to granular starch hydrolysate compositions.

Suitable salts that can be combined with the granular starch hydrolysates include the alkali metal chlorides and sulfates, the alkaline metal chlorides and sulfates, and mixtures of two or more thereof, e.g., sodium potassium sulfate or chloride. Suitable carbohydrate saccharides include fructose, dextrose, sucrose, corn syrup solids, corn syrups, maltodextrins (e.g., having a DE of about 5 or more and a DP of less than about 20) and mixtures of two more thereof. Suitable emulsifiers include food grade emulsifiers. Examples of such emulsifiers are mixed mono- and diglycerides, propylene glycol esters, lactylated esters, sorbitan esters, polyglycerol esters, polysorbates and ethoxylates. Many compositions will contain mixtures of carbohydrate saccharide, salt and/or emulsifiers.

Both salt and saccharides occur as by-products in the production of granular starch hydrolysates. Particularly in the case of salt, the beneficial amounts described below may be controlled by the extent of washing of the granular starch hydrolysate. Typically, additional saccharide will be necessary to obtain the beneficial interactions.

The amount of salt necessary to effect a beneficial interaction with a granular starch hydrolysate can be determined from examination of yield stress values. Yield stress values increase with addition of salt. Accordingly, the amount of salt necessary is that that produces a composition having a yield stress sufficient to produce an organoleptically acceptable product. In the case of sodium chloride, the increase in yield stress levels off at about 1% to 2% (based on dry starch hydrolysate). Accordingly, it is preferred to have salt present at a level of at least 1 part salt per 1,000 parts starch hydrolysate. In order to maximize yield stress at least about 10 parts per thousand is preferred. Additional salt may be added to provide proper taste.

Emulsifiers aid in the retention of fat-like character of starch hydrolysate composition. The amount of emulsifier necessary to effect the beneficial effects is generally in the range of about 0.1% to about 5%. The precise amount will be dependent upon the emulsifier and the other ingredients present and can be determined easily.

The saccharides listed above have shown particular utility in enhancing the fat-like properties of compositions that experience elevated temperatures or freeze/thaw cycles. The amount of saccharide necessary to provide such enhancement will depend on the saccharide, the granular starch hydrolysate, the other ingredients and their relative concentrations. The saccharide should be present in an amount sufficient to provide the enhanced fat-like properties to compositions that will undergo heating or freeze/thaw cycles. Determination of this amount can easily be determined by experiments such as those detailed below and is well within the skill in the art. Amounts of saccharide beyond that necessary to provide the enhancement may be added to provide proper taste.

As previously described, the utility of starch hydrolysates in the replacement of fats depends on their ability to produce compositions exhibiting fat-like organoleptic properties. Many applications entail thermal cycling such as heating of the composition and/or repeated freeze/thaw cycles. Combinations of ingredients that retain their fat-like organoleptic property after being heated and/or frozen are particularly desirable due to their increased utility in such formulations. The salts and saccharides described have been found to enhance the ability of granular starch hydrolysates to retain their fat-like properties after being heated and/or frozen.

Evaluation of Properties Retention Subsequent to Thermal Cycling

The stability of compositions that have undergone thermal cycling was evaluated. Stability was evaluated by yield stress measurements, water mobility measurements using $O^{17}$ NMR spectroscopy, and sensory evaluations.

Yield Stress Tests

Yield stress was measured on a Haake Rotoviscometer at room temperature on each sample following the various heat treatments described below. Data collected from 3 samples of each treatment was averaged. The following Haake Rotoviscometer settings were selected: torque switch=500, vane inserted into sample for three minutes before the rotation starts, speed setting=162=3.61 rpm. Yield stress was calculated by multiplying 29.72 times the Haake reading.

Water Mobility

Water mobility of the samples following the treatments was studied. Water mobility was evaluated by $H^1$ decoupled $O^{17}$ NMR experiments, A GN 300 NB multinuclear NMR spectrometer was operated at 40.68 $MH_2$, Measurements were made at natural abundance levels. A single pulse $O^{17}$ measurement with proton decoupling was done at room temperature (20°–27° C.). A 90 degree pulse of 35 $\mu$sec and a recycling time of 205.87 msec were used.

The mobility of water molecules for each sample was monitored by measuring the $O^{17}$ NMR transverse relaxation rate ($R_2$, $sec^{-1}$). The line width ($\nu_{obs}$) at half height of each spectrum was obtained by using the computer line fit routine available on the GN 300 NIC 1280 computer software (General Electric, Inc., Fremont, Calif.). The $R_2$ ($sec^{-1}$) or transverse relaxation time ($T_2$, sec) was then calculated from the line width by the following equation:

$$R_2 (sec^{-1}) = \pi \nu_{obs} (sec^{-1}) = 1/T_2 (sec)$$

The net or differential transverse relaxation rate ($\Delta R_2$, $sec^{-1}$) was calculated by subtracting the line width of liquid water ($\nu_{free}$) from line width of the sample ($\nu_{obs}$) before multiplying by $\pi$:

$$\Delta R_2 (sec^{-1}) = \pi(\nu_{obs} - \nu_{free})(sec^{-1})$$

In general, as $R_2$ or $\Delta R_2$ increases, the mobility of the water decreases. Decreased water mobility is believed to correlate to superior organoleptic properties and storage stability properties.

Sensory Evaluations

Sensory evaluations were performed on samples from each treatment by a panel of five to ten participants. Each sample was evaluated for fat-like mouthfeel on a scale of 1 to 9 (1 as not fat-like and 9 as the most fat-like), texture characteristics, and overall acceptability. Samples were prescreened before evaluation and if obvious grittiness or fluidity was detected, the samples were declared unacceptable and given a score of 1.

Preparation of Composition

Waxy maize starch hydrolysate from Run No. 6D. After drying, the hydrolyzed waxy maize starch was analyzed and the following data collected:

| Moisture | 5.66% |
|---|---|
| Ash | 1.04% |
| $M_w$-GPC | 5733 |
| $M_w/M_n$ | 1.9 |

A slurry of the dry starch hydrolysate and each ingredient to be evaluated was then prepared. The dry starch hydrolysate was sifted with an 80 mesh (180 micrometer opening) screen to prevent plugging the MICROFLUIDIZER with large particles. Thirteen hundred grams (1,300 g) starch hydrolysate/water slurry was prepared by combining 273 g dry as is starch hydrolysate with the appropriate amount of tested ingredient and water to yield a starch hydrolysate slurry. Each composition contained 20% starch hydrolysate, the indicated amount of co-ingredient and water. Deionized water was used and added at 45° C., the desired MICROFLUIDIZER input temperature.

The starch hydrolysate/ingredient blend was added into water with the agitation of a Servodyne mixer at 60 rpm. Emulsifiers evaluated were added directly to 45° C. deionized water to allow melting. Increasing the agitation to 170 rpm, vigorous mixing was applied for 5 to 10 minutes to form a homogeneous slurry devoid of any lumps. Slurries were covered with aluminum foil and kept for 1.5 to 2 hours in a 49° C. water bath and periodically stirred manually; this allowed the solution to attain an equilibrium temperature of 47° C. and all starch particles to hydrate. Heating to 47° C. allowed the slurry to maintain a 45° C. temperature when transferred to the MICROFLUIDIZER reservoir.

Tap water was heated in the water bath along with the slurry and passed through the MICROFLUIDIZER to equalize the MICROFLUIDIZER reservoir and interior temperature. The slurry was transferred to the reservoir and sheared through the MICROFLUIDIZER using module 15-31, as described above. Output temperature was measured consistently at 56° C. to 59° C. and the pressure was adjusted to 10,000 psi.

STUDY I

Collection of Samples

Fifteen (15) 2 oz. glass bottles of the finished compositions were collected and all allowed to remain at room temperature (approximately 23° C.) for 3 hours. The following treatments were then conducted:

Treatments 1) 3 Hour Room Temperature (3 hr RT): Three of the 15 samples remained at room temperature for the initial 3 hour results.

2) 72° C.: Three samples were heated in a 72° C. water bath for 30 minutes (additional time was allowed to attain a temperature of 72° C. if needed). A temperature probe was placed through a hole in the bottle cap to monitor the central temperature. Samples were not stirred during the incubation period. Samples were cooled for 7 minutes at room temperature. The samples were then cooled in an ice water bath to room temperature.

3) 85° C.: Three samples were subjected to the same procedure as described in 2) except heated in an 85° C. water bath.

4) Freeze/Thaw (F/T): Three samples were frozen at 0° F. (−18° C.) for 20 hours and allowed to thaw to room temperature for 7 hours.

5) Freeze/Thaw Cycles (F/T/F/T): Three samples were frozen for 20 hours at 0° F. (−18° C.) and allowed to thaw to room temperature for 7 hours and again recycled for 20 hours freezing/7 hours thawing.

STUDY II

Due to noticed setback and improved fat-like character of the heated samples after a 24 hour period in Study I, the study was repeated with variations in the time yield stress and sensory evaluations were made. Water mobility responses were not measured on the repeated Study II samples. F/T/F/T treatment was not measured due to relative indifference noticed between F/T and F/T/F/T samples. Yield stress tests continued to be taken 3 hours after preparing the composition and immediately after 72° C. and 85° C. heat treatment as a comparison and verification of repeatable results. The details of the experimental methods are listed below.

Collection of Samples

Fourteen (14) glass jars of 2 oz. finished composition samples were collected from the MICROFLUIDIZER and all remained at room temperature for a 3 hour interval.

Treatments 1) 3 Hours Room Temperature (3 hr RT): Two of the 14 samples remained at room temperature for the initial 3 hour results.

2) 24 Hours Room Temperature: Two of the 14 samples remained at room temperature for an additional 2 hours while other samples were heat treated, then kept in a 35° F. (3° C.) refrigerator for 20 hours, removed and warmed for 4 hours to room temperature.

3) 72° C.: Two samples were heated to 72° C. as described in Study I-2).

4) 72° C., 24 Hours: Two samples were heated to 72° C. as described in Study I-2); however, after cooling, they were placed in a 35° F. (3° C.) refrigerator along with the RT 24 hr samples for 20 hours and warmed to room temperature for 4 hours.

5) 85° C.: Two samples were heated to 85° C. as described in Study I-3).

6) 85° C., 24 Hours: Two samples followed treatment 4) procedure except placed in a 85° C. water bath.

7) F/T: Two samples followed the same procedure as in Study I-4).

Yield Stress Measurements

Yield stress measurements were conducted immediately after the above treatments following the procedure for yield stress measurement in Study I except using a 2 minute interval with the vane inserted in the sample before rotation was started.

Sensory Evaluations

One sample from each of the above treatments 2), 4), 6), and 7) were sensory evaluated as described in Study I.

RESULTS

20% D.S. Waxy Maize Starch Hydrolysate Control—A fat-like composition was obtained 3 hours after the preparation. Twenty-four hours later, the compositions had increased in yield stress, which resulted in a slightly more fat-like mouthfeel. Immediately after 72° C. heating, compositions had decreased in yield stress and fat-like mouthfeel but remained acceptable. Twenty-four hours later, the compositions remained acceptable and increased in firmness. Yield stress decreased immediately after 85° C. heating, and reaggregation occurred 24 hours later, resulting in a gritty texture. The F/T treatment produced a gritty, oatmeal-like texture due to syneresis and separation of starch and water. Water mobility was similar to the untreated composition after 72° C. and 85° C. treatment, but greatly reduced with freezing and thawing.

Hydrocolloids

Carboxymethyl Cellulose (CMC)—A composition containing 0.3% CMC (Aqualon Co., 7HOF) was prepared. Twenty-four hours after preparing the composition, the mouthfeel was smooth, creamy and similar to the control. Twenty-four hours after 72° C. heating, yield stress and mouthfeel remained the same as the untreated composition. This composition had the highest yield stress out of all treatments 24 hours after 85° C. heating; however, gritty mouthfeel was detectable. F/T samples exhibited aggregation with syneresis similar to a control and decreased to almost undetectable yield stress demonstrating oatmeal-like consistency. Water mobility was stable with 72° C. and 85° C. treatment, but greatly increased with F/T treatment.

Xanthan (XAN)—A composition containing 0.3% xanthan was prepared. The untreated composition was smooth and creamy. 72° C. heated samples decreased in yield stress 24 hours after setback when compared to the untreated composition; however, the mouthfeel remained acceptable. Compared to the untreated composition, a marked increase in yield stress was measured 24 hours after 85° C. treatment; however, gummy, sticky mouthfeel was characterized. Water mobility was similar in heat treated samples, but increased in samples that were F/T cycled. F/T cycles caused starch reaggregation resulting in separation of water and a gritty mouthfeel, and the yield stress was almost undetectable.

Hemicellulose (HEM)—A composition containing 0.3% corn hull hemicellulose was prepared. A smooth mouthfeel was characterized 24 hours after the composition was prepared. Samples heated to 72° C. and allowed to setback decreased in yield stress slightly compared to the 24 hours untreated composition, and the mouthfeel was characterized as smooth, creamy and acceptable. Yield stress greatly increased due to 85° C. treatment and 24 hour setback, but had detectable lumps when sensory evaluated. Water mobility increased slightly with 72° C. and 85° C. heating and greatly with F/T cycles.

Hydroxypropyl Methyl Cellulose (MC)—A composition containing 0.3% METHOCEL TM F4M (Dow Chemical Co.) was prepared. An acceptable, smooth mouthfeel was characterized 24 hours after the composition was prepared. However, slimy, lumpy texture was obtained 24 hours after 72° C. heating, and yield stress decreased slightly. Yield stress greatly increased with 85° C. treatment after 24 hours setback, but was declared unacceptable due to the chalky texture. F/T compositions also had severe syneresis and reaggregation. Water mobility was similar when untreated, and when heated at both temperatures, but greatly increased with F/T treatment.

Sugars

Sucrose (SUC)—A composition containing 30% sucrose was prepared. Untreated compositions at 24 hours had a smooth and creamy texture. All compositions showed a greatly increased yield stress and firm mouthfeel. Compositions retained a smooth but heavy, pituous, gummy mouthfeel. Upon heating to 72° C. and 85° C., yield stress also increased compared to the untreated composition in both cases. F/T samples maintained a cohesive structure and retained a fat-like, rigid texture. Yield stress was only slightly lower than an untreated composition in F/T samples. Water mobility decreased to half compared to a control in all cases indicating water is more bound in the sucrose system. Water mobility was also relatively stable throughout all treatments with a slightly higher response noted in the F/T cycled samples.

Fructose (FRU)—A composition containing 30% fructose was prepared. Samples that were untreated or heated to 72° C. or 85° C. and evaluated 24 hours after preparation had a smooth, rigid but sticky, oily mouthfeel and thus were declared unacceptable by 2 of the 5 evaluators although an increased yield stress was noted. A very high yield stress of 3685 was measured 24 hours after 85° C. treatment; however, lumpiness was also detectable and thus it was unacceptable. F/T samples were acceptable in creamy smoothness and slightly lower in yield stress (1859) compared to the 24 hour untreated composition (2672). Water mobility was again very low under all treatments, similar to other tested sugars, again indicating water is highly bound in these systems.

Dextrose (DEX)—A composition containing 30% dextrose was prepared. All samples were heavy and rigid, including F/T treated compositions. All samples were acceptable except 24 hours after 85° C. treatment, where increased rigidity and cohesiveness caused a lumpy, cohesive texture. Yield stress and mouthfeel achieved was similar to an untreated sample 24 hours after 72° C. Yield stress increased with both 72° C. and 85° C. treatment after 24 hours. The highest yield stress was measured in 85° C. treated samples, but had a balling, lumpy texture, resulting in an unacceptable rating. Water was again highly bound in all dextrose systems. Water mobility was lowest in the untreated sample and relatively low after both heat and F/T treatments.

Corn Syrup Solids (CSS)—A sample containing 30% CSS was prepared. (STALEY Corn Syrup Solids 24R, from A. E. Staley Manufacturing Co., Decatur, Ill.) The highest yield stress of all tested ingredients was obtained with addition of CSS (1250–2000 Pa) under all treatments. Both 24 hours untreated and 72° C., 24 hours heated compositions had smooth, rigid, slightly gummy mouthfeel. After 85° C. treatment, however, increased cohesive lumpiness caused 4 out of 5 evaluators to declare the compositions unacceptable, even though a yield stress of 2000 Pa was measured. F/T samples were unanimously acceptable and had the lowest yield stress (1250) after 24 hours setback.

Emulsifiers

DUR-LO ® (DUL)—A composition containing 5% mixed mono- and diglycerides was prepared. (DUR-LO from Van Den Bergh Foods). Fat-like mouthfeel greatly increased in the composition upon the addition of DUR-LO except when F/T treated. Yield stress greatly increased as did firm mouthfeel over a 24 hour period. Samples that were prepared and left untreated for 24 hours had smooth, creamy character. Samples heated to 72° C. and immediately tested before setback decreased in yield stress but remained acceptable. The fat-like rigidity and firmness also decreased, but regained the heaviness and high yield stress when allowed to setback for 24 hours. Similar effect was also seen in 85° C. heated samples. Samples were acceptably smooth without reaggregation after 24 hour setback. This effect seen in all emulsifiers may be an interaction or a masking of the grittiness by the fat-like texture of the emulsifiers themselves. F/T samples underwent syneresis and reaggregated starch occurred. Water mobility remained relatively stable following heat treatment but increased greatly following F/T treatment.

Santone 3-1-SH (SAN)—A composition containing 2% mixed polyglycerol esters of fatty acids was prepared (SANTONE 3-1-SH, Van Den Bergh Foods) Twenty-four hours after being prepared, untreated and heat treated samples had good fat-like mouthfeel. 85° C. heated samples improved significantly in mouthfeel with setback compared to a gritty control under the same treatment. Yield stress decreased with 72° C. treatment and increased with 85° C. treatment compared to an untreated composition. Water mobility increased slightly upon heat treatment but increased greatly with F/T. Less bound water was also evidenced by great syneresis.

DUR-EM 207E (DUE)—A composition containing 0.5% mixed mono- and diglycerides was prepared. (Van Den Bergh Foods) Samples untreated after 24 hours were unacceptable by 3 out of 6 panelists due to increased slimy mouthfeel. Samples heated to both 72° C. and 85° C. remained smooth and creamy after setback for 24 hours. Yield stress decreased slightly with 72° C. heating, but increased with 85° C. heating. F/T treatment showed reaggregated starch and severe syneresis, resulting in almost undetectable yield stress. Water mobility was stable with heat treatment, but greatly increased after F/T treatment.

DURFAX 80K (DUF)—A composition containing 0.5% polysorbate 80 was prepared. (Van Den Bergh Foods) All heated and untreated samples had unanimously acceptable, smooth and creamy mouthfeel after 24 hours. A strong bitter taste was detectable at 0.5% level. Yield stress decreased slightly with composition heated to 72° C. or 85° C., but water mobility was stable and similar to the unheated compositions. F/T samples reaggregated with syneresis. Water mobility greatly increased and fat-like mouthfeel were greatly reduced following F/T.

Proteins

Egg White Solids (EWS)—A composition containing 2% egg white solids (P-19, Henningsen Foods) was prepared. Fat-like mouthfeel was only acceptable when samples were untreated. After heating at both 72° C. and 85° C., starch reaggregation or egg white coagulation occurred, resulting in a lumpy texture and unacceptable mouthfeel. F/T treatment reduced the yield stress; however, less syneresis was observed compared to a 20% d.s. waxy maize starch hydrolysate control under the same treatment. Water mobility increased greatly with F/T cycle but was not substantially changed by heat treatment. Compared to the untreated composition, yield stress decreased slightly with 72° C. treatment after 24 hour setback treatment and increased with 85° C. treatment.

Soy Protein (SOP)—A composition containing 2% soy protein isolate (MIRA-PRO 111, A. E. Staley Mfg. Co.) was prepared. This protein offered the most potential out of the four tested proteins for maintenance of fat-like character. No lumpiness nor increased aeration was noticed after 72° C. treatment. Lumpiness due to reaggregation of starch was detected after 24 hour setback on compositions treated at 85° C. Yield stress decreased with 72° C. treatment and increased with 85° C. treatment compared to the untreated samples after 24 hours. Severe syneresis occurred as well as reduction in yield stress and increase in water mobility, indicating more free water was present after F/T treatment. No significant change in water mobility was measured in the heated samples.

Milk Protein (MIP)—A composition containing 2% milk protein (BIPRO, La Seuer) was prepared. Samples showed increased yield stress and significant improvement in smooth, fat-like palatability when allowed to setback up for 24 hours. Samples untreated or heated to 72° C. were acceptable. However, reaggregation and lumpiness were detected in 85° C. treated samples after 24 hour setback even though yield stress was high (2740). The 85° C. treated sample was unanimously unacceptable. F/T composition reaggregated with almost undetectable yield stress and great increase of water mobility.

Sodium Caseinate (SCA)—A composition containing 0.5% Na-caseinate (Alanate 110, New Zealand Milk Products Co.) was prepared. Increased creaminess and aeration was observed in all samples. The sample heated to 72° C. decreased in yield stress, but remained acceptable in fat-like character. Yield stress increased significantly 24 hours after 85° C. heat treatment; however, the sample was unanimously unacceptable because of gritty mouthfeel and decreased fat-like character. Sample properties were degraded by F/T treatment showing less bound water, reduced yield stress and a marked decrease in fat-like mouthfeel due to syneresis and grittiness.

20% Salt and Sugar—Due to the marked synergistic effect of 30% sugars with waxy maize starch hydrolysate, it was hypothesized that increased solids may have increased its stability. As an extension of this study, 20% d.s. waxy maize starch hydrolysate with additional 20% table salt was prepared as a comparison to the addition of 20% sugar. It was determined that increasing the % solids with salt did not cause an increase in yield stress and only slightly decreased the water mobility. However, 20% sugars had a marked increase in yield stress, great decrease in water mobility and maintained the fat-like mouthfeel compared to a control, with or without salt, under the same treatments. For F/T and F/T/F/T treated samples, both 20% salt and 20% sugar compositions maintained a rigid texture. This stability during F/T cycles was believed to result from the freezing point depression effect of the salt.

All data obtained in Studies I and II is represented in Table I, with the exception of the results for 20% salt and 20% sugar, average yield stress calculations from Study I and Study II are reported at 3 hr RT, 72° C., 85° C. and F/T. F/T/F/T data was obtained only from Study I, while 24 hr RT, 72° C. 24 hr and 85° C. 24 hr were determined in Study II. All water mobility measurements were obtained from Study I. Listed along with corresponding ingredient and treatment is: mouthfeel characteristics, $O^{17}$ NMR water mobility, yield stress, overall Acceptability ("A"), Unacceptability ("U"), fat-like mouthfeel score on a scale of 1–9 (1 is nonfat-like–9 is fat-like) and the number of overall Acceptable to Unacceptable (A-U) evaluations.

Samples 1–8 are controls containing 20% d.s. waxy maize starch hydrolysate. Samples 9–136 are 20% d.s. waxy maize starch hydrolysate plus the previously indicated amounts of additional ingredients.

Figure 2:
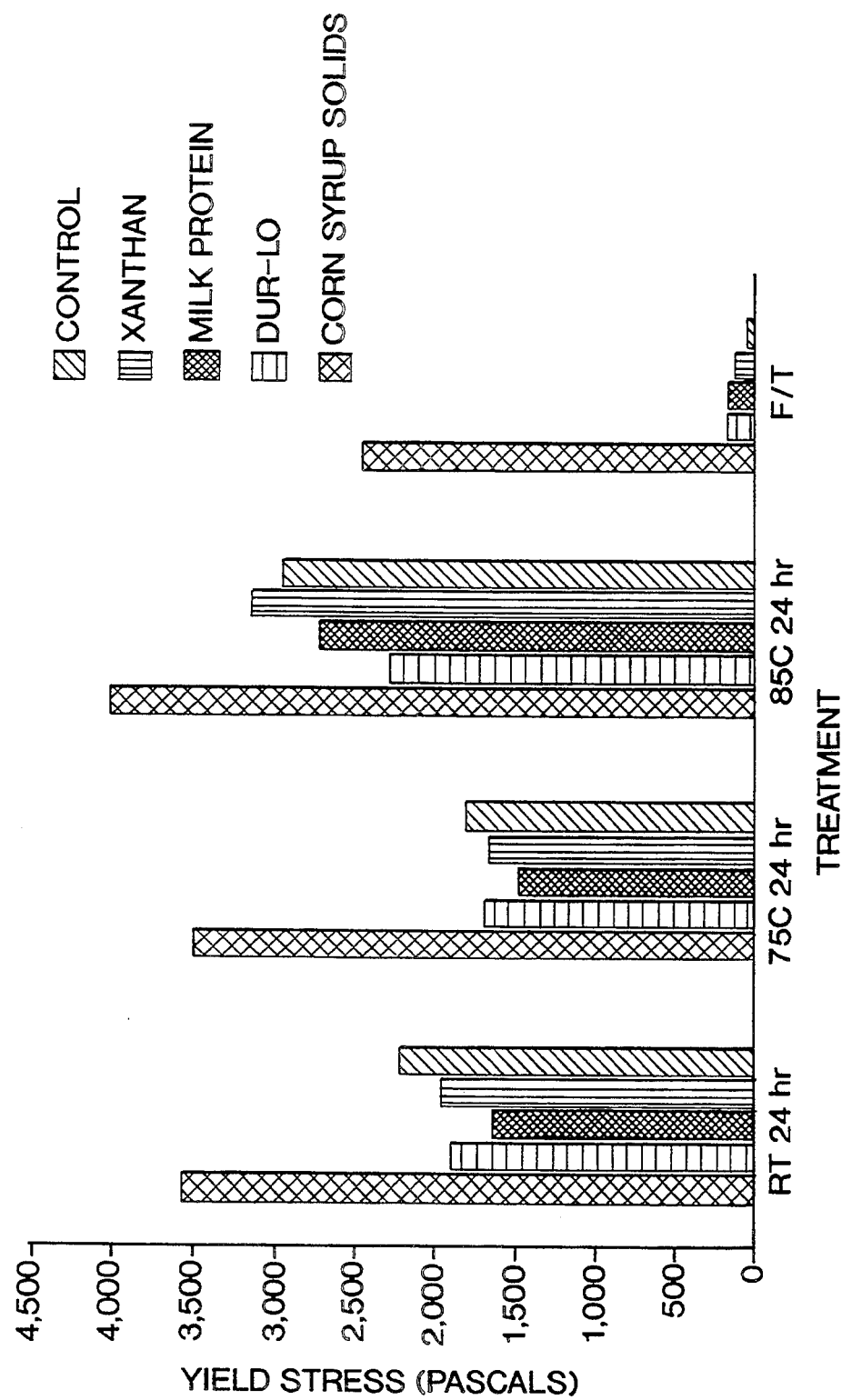
FIG. 2 is a bar graph showing the effect of ingredients on the yield stress of an aqueous dispersion of a fragmented waxy maize starch hydrolysate.

FIG. 2 compares the effect of xanthan, milk protein, DUR-LO and corn syrup solids on the yield stress of a waxy maize starch hydrolysate composition following the indicated thermal events.

Figure 3:
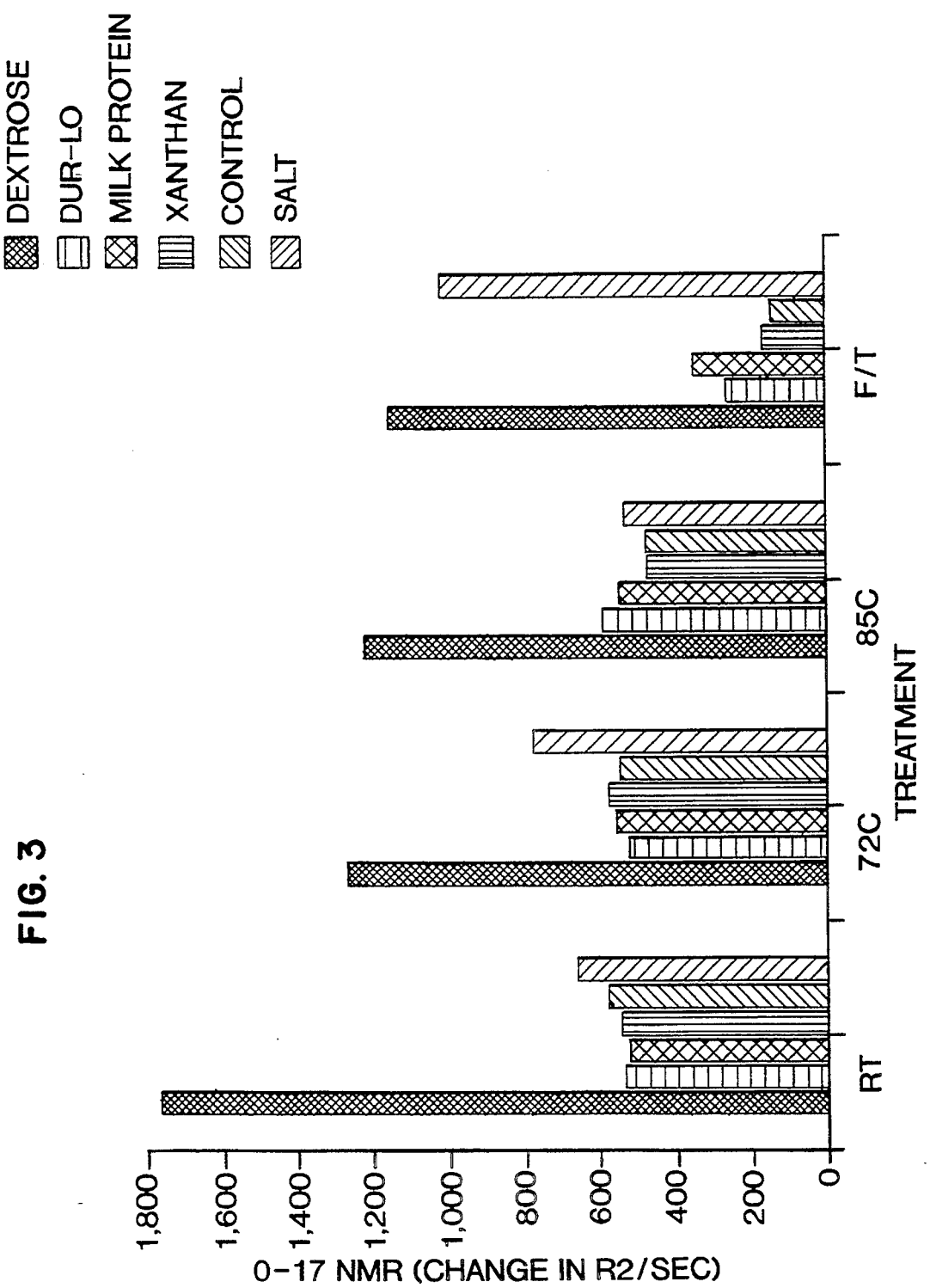
FIG. 3 is a bar graph showing the effect of ingredients on the water mobility of an aqueous dispersion of a fragmented waxy maize starch hydrolysate.

FIG. 3 compares the effect of dextrose, DUR-LO, milk protein, xanthan and sodium chloride on the water mobility of waxy maize starch hydrolysate following the indicated thermal events.

Figure 4:
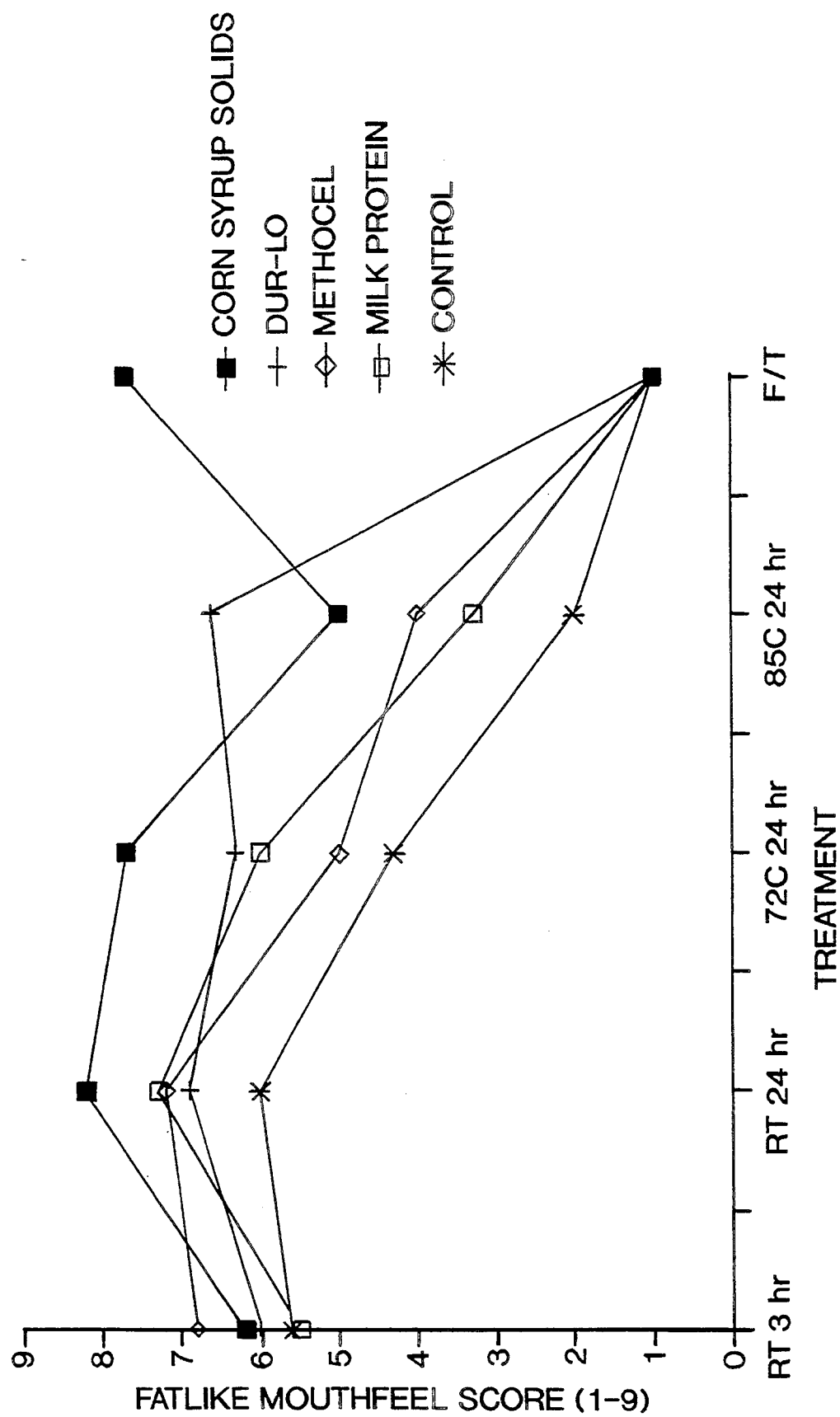
FIG. 4 is a bar graph showing the effect of ingredients on the fat-like mouthfeel of an aqueous dispersion of a fragmented waxy maize starch hydrolysate.

FIG. 4 compares the effect of corn syrup, DUR-LO, METHOCEL and milk protein on the fat-like mouthfeel of waxy maize starch hydrolysate following the indicated thermal events.

The data of Table 1 and the comparative representations of FIGS. 2, 3 and 4 demonstrate unexpected interactions between a granular starch hydrolysate having a weight average molecular weight of less than about 10,000 g/mol and being comprised of a major amount by weight of cold-water insoluble hydrolysate and a minor amount by weight of cold-water soluble hydrolysate and carbohydrate saccharides. These interactions are revealed by evaluating the water mobility, yield stress and mouthfeel of the various compositions. The importance of the interactions is that they allow the utilization of the starch hydrolysates in applications requiring either heat stability or F/T stability.

The exact nature of the interaction between the granular starch hydrolysate and saccharide is not known. One explanation is that the presence of the saccharide raises the temperature at which the granular starch hydrolysate dissolves in water. Another theory relates to the relative amounts of water present to hydrate the starch hydrolysate and the saccharide. In any event, it is known that when present in a sufficient amount, the saccharides enhance the fat-like properties of compositions containing granular starch hydrolysate that must undergo heating or F/T cycles.

The data of Table I and the comparative representation from FIG. 4 also demonstrates the effectiveness of emulsifiers as aids to maintain the fat-like character of compositions that have been heated to temperatures typically used in processing dairy products at both 72° C. and 85° C. The four emulsifiers tested exhibited superior fat-like mouthfeel compared to the control.

TABLE I

INGREDIENT INTERACTIONS

| Observation | Type | Treatment | Character | Water Immobility ΔR2 | Yield Stress (Pa) | Sensory | Score | A-U |
|---|---|---|---|---|---|---|---|---|
| 1 | 20% | 3 HR RT | smooth | — | 718 | A | 5.6 | 6-1 |
| 2 | 20% | 72° C. | smooth, slimy, oily | — | 483 | A | 4.4 | 5-1 |
| 3 | 20% | 85° C. | runny, smooth | — | 145 | U | 1.0 | 0-1 |
| 4 | 20% | F/T | gritty | 144 | 0 | U | 1.0 | 0-1 |
| 5 | 20% | F/T/F/T | gritty | 148 | 0 | U | 1.0 | 0-1 |
| 6 | 20% | 24 HR RT | smooth | 576 | 1108 | A | 6.0 | 6-1 |
| 7 | 20% | 72° C. 24 HR | smooth, slimy | 544 | 913 | U | 4.3 | 3-4 |
| 8 | 20% | 85° C. 24 HR | gritty, lumpy | 474 | 1476 | U | 2.0 | 0-1 |
| 9 | CMC | 3 HR RT | smooth | — | 781 | A | — | 1-0 |
| 10 | CMC | 72° C. | smooth, creamy | 1 | 512 | A | — | 3-0 |
| 11 | CMC | 85° C. | runny, smooth | — | 126 | U | — | 0-1 |
| 12 | CMC | F/T | gritty | 226 | 107 | U | 1.0 | 0-1 |
| 13 | CMC | F/T/F/T | gritty | — | 0 | U | 1.0 | 0-1 |
| 14 | CMC | 24 HR RT | smooth, creamy | 642 | 1117 | A | 6.5 | 7-0 |
| 15 | CMC | 72° C. 25 HR | smooth | 529 | 1117 | A | 4.6 | 5-2 |
| 16 | CMC | 85° C. 24 HR | lumpy | 470 | 1612 | U | 1.0 | 2-3 |
| 17 | XAN | 3 HR RT | smooth, creamy | — | 782 | A | 3.7 | 4-0 |
| 18 | XAN | 72° C. | smooth, creamy | — | 512 | A | 3.0 | 3-1 |
| 19 | XAN | 85° C. | smooth, creamy, runny | — | 135 | U | 1.0 | 0-1 |
| 20 | XAN | F/T | gritty | 166 | 77 | U | 1.0 | 0-1 |
| 21 | XAN | F/T/F/T | gritty | 172 | 0 | U | 1.0 | 0-1 |
| 22 | XAN | 24 HR RT | smooth, creamy | 540 | 984 | A | 6.2 | 4-1 |
| 23 | XAN | 72° C. 24 HR | smooth | 572 | 843 | A | 4.7 | 4-1 |
| 24 | XAN | 85° C. 24 HR | gummy sticky | 469 | 1578 | U | 5.0 | 3-2 |
| 25 | HEM | 3 HR RT | smooth, slimy | — | 724 | A | 6.2 | 5-0 |
| 26 | HEM | 72° C. | smooth, slimy | — | 430 | U | 3.4 | 2-4 |
| 27 | HEM | 85° C | slimy | — | 181 | U | 1.0 | 0-1 |
| 28 | HEM | F/T | gritty | 134 | 86 | U | 1.0 | 0-1 |
| 29 | HEM | F/T/F/T | gritty | 158 | 0 | U | 1.0 | 0-1 |
| 30 | HEM | 24 HR RT | smooth, creamy | 562 | 969 | A | 6.4 | 4-2 |
| 31 | HEM | 72° C. 24 HR | smooth, creamy | 538 | 862 | A | 5.4 | 4-1 |
| 32 | HEM | 85° C. 24 HR | some small lumps | 503 | 1611 | U | 4.9 | 3-2 |
| 33 | MC | 3 HR RT | smooth, oily | — | 771 | A | 6.8 | 5-0 |
| 34 | MC | 72° C. | smooth, slimy | — | 468 | U | 4.7 | 1-4 |
| 35 | MC | 85° C. | runny | — | 162 | U | 1.0 | 0-1 |
| 36 | MC | F/T | gritty | 208 | 94 | U | 1.0 | 0-1 |
| 37 | MC | F/T/F/T | gritty | 172 | 0 | U | 1.0 | 0-1 |
| 38 | MC | 24 HR RT | smooth | 658 | 930 | A | 7.2 | 5-0 |
| 39 | MC | 72° C. 24 HR | smooth | 528 | 800 | U | 5.0 | 1-4 |
| 40 | MC | 85° C. 24 HR | chalky | 531 | 1421 | U | 4.0 | 1-4 |
| 41 | SUC | 3 HR RT | smooth, slimy, rigid | — | 1261 | U | 5.1 | 4-4 |
| 42 | SUC | 72° C. | smooth, slimy, rigid | — | 1227 | A | 5.2 | 6-1 |
| 43 | SUC | 85° C. | smooth, slimy, lumpy | — | 1003 | U | 4.8 | 3-4 |
| 44 | SUC | F/T | smooth, creamy | 1461 | 1157 | A | 6.6 | 7-0 |
| 45 | SUC | F/T/F/T | smooth, oily | 1445 | 1061 | A | 5.5 | 2-0 |
| 46 | SUC | 24 HR RT | smooth, creamy | 1251 | 1272 | A | 6.5 | 7-0 |
| 47 | SUC | 72° C. 24 HR | smooth | 1361 | 1605 | A | 6.4 | 6-1 |
| 48 | SUC | 85° C. 24 HR | smooth | 1245 | 1798 | A | 5.1 | 6-1 |
| 49 | FRU | 3 HR RT | smooth, rigid | — | 890 | A | 4.8 | 6-0 |
| 50 | FRU | 72° C. | rigid, oily, slimy | — | 959 | A | 5.3 | 3-1 |
| 51 | FRU | 85° C. | runny, oily, slimy | — | 526 | U | 1.0 | 0-1 |
| 52 | FRU | F/T | smooth | 1496 | 930 | A | 6.2 | 4-1 |
| 53 | FRU | F/T/F/T | smooth | 1037 | 873 | A | 5.7 | 6-0 |
| 54 | FRU | 24 HR RT | sticky, oily, slimy | 1464 | 1336 | U | 5.9 | 3-2 |
| 55 | FRU | 72° C. 24 HR | slimy, oily | 1240 | 1434 | U | 5.2 | 3-2 |
| 56 | FRU | 85° C. 24 HR | lumpy | 1011 | 1843 | U | 5.4 | 1-4 |
| 57 | DEX | 3 HR RT | smooth, slimy, rigid | — | 1084 | A | 5.3 | 6-0 |
| 58 | DEX | 72° C. | smooth, slimy, oily | — | 1074 | A | 5.3 | 6-0 |
| 59 | DEX | 85° C. | smooth, slimy, rigid | — | 753 | A | 5.8 | 6-0 |
| 60 | DEX | F/T | smooth | 1151 | 992 | A | 5.1 | 4-2 |
| 61 | DEX | F/T/F/T | smooth, rigid | 1068 | 936 | A | 5.4 | 5-0 |
| 62 | DEX | 24 HR RT | smooth | 1764 | 1358 | A | 6.6 | 4-1 |
| 63 | DEX | 72° C. 24 HR | smooth | 1265 | 1534 | A | 6.9 | 5-0 |
| 64 | DEX | 85° C. 24 HR | lumpy | 1216 | 1887 | U | 3.7 | 1-4 |
| 65 | CSS | 3 HR RT | smooth, oily, rigid | — | 1425 | A | 6.2 | 9-0 |
| 66 | CSS | 72° C. | smooth, oily, rigid | — | 1566 | A | 6.0 | 7-2 |
| 67 | CSS | 85° C. | smooth, lumpy, rigid | — | 1252 | A | 5.6 | 6-3 |
| 68 | CSS | F/T | smooth | 1406 | 1237 | A | 7.7 | 5-0 |
| 69 | CSS | F/T/F/T | smooth, rigid | 1215 | 1200 | U | 6.2 | 3-2 |
| 70 | CSS | 24 HR RT | smooth, rigid | 1200 | 1785 | A | 8.2 | 4-1 |
| 71 | CSS | 72° C. 24 HR | smooth | 1145 | 1754 | A | 7.7 | 5-0 |
| 72 | CSS | 85° C. 24 HR | lumpy | 916 | 2014 | U | 5.0 | 1-4 |
| 73 | DUL | 3 HR RT | smooth, rigid | — | 733 | A | 6.0 | 5-0 |

TABLE I-continued

INGREDIENT INTERACTIONS

| Observation | Type | Treatment | Character | Water Immobility ΔR2 | Yield Stress (Pa) | Sensory | Score | A-U |
|---|---|---|---|---|---|---|---|---|
| 74 | DUL | 72° C. | smooth, creamy | — | 481 | A | 6.3 | 4-1 |
| 75 | DUL | 85° C. | smooth, creamy, runny | — | 201 | U | 1.0 | 0-2 |
| 76 | DUL | F/T | gritty | 263 | 98 | U | 1.0 | 0-1 |
| 77 | DUL | F/T/F/T | gritty | 185 | 36 | U | 1.0 | 0-1 |
| 78 | DUL | 24 HR RT | smooth, creamy | 531 | 951 | A | 6.9 | 6-0 |
| 79 | DUL | 72° C. 24 HR | smooth, creamy | 521 | 850 | A | 6.3 | 5-1 |
| 80 | DUL | 85° C. 24 HR | smooth | 588 | 1147 | A | 6.6 | 5-1 |
| 81 | SAN | 3 HR RT | smooth | — | 754 | A | 6.4 | 5-0 |
| 82 | SAN | 72° C. | smooth, slimy | — | 498 | A | 6.6 | 4-1 |
| 83 | SAN | 85° C. | creamy, runny | — | 153 | U | 1.0 | 0-2 |
| 84 | SAN | F/T | gritty | 302 | 112 | U | 1.0 | 0-1 |
| 85 | SAN | F/T/F/T | gritty | 221 | 57 | U | 1.0 | 0-1 |
| 86 | SAN | 24 HR RT | smooth, creamy | 657 | 974 | A | 8.0 | 5-0 |
| 87 | SAN | 72° C. 24 HR | smooth, creamy | 589 | 829 | A | 6.5 | 5-0 |
| 88 | SAN | 85° C. 24 HR | slight lumpy | 530 | 1323 | A | 6.3 | 4-1 |
| 89 | DUE | 3 HR RT | smooth, creamy, oily | — | 756 | A | 7.2 | 7-0 |
| 90 | DUE | 72° C. | smooth, creamy | — | 460 | A | 7.0 | 5-0 |
| 91 | DUE | 85° C. | creamy, runny | — | 159 | U | 1.0 | 0-1 |
| 92 | DUE | F/T | gritty | 215 | 45 | U | 1.0 | 0-1 |
| 93 | DUE | F/T/F/T | gritty | 125 | 45 | U | 1.0 | 0-1 |
| 94 | DUE | 24 HR RT | smooth, oily | 537 | 988 | U | 6.4 | 3-3 |
| 95 | DUE | 72° C. 24 HR | smooth | 569 | 795 | A | 5.9 | 5-1 |
| 96 | DUE | 85° C. 24 HR | creamy | 470 | 1147 | A | 5.8 | 4-2 |
| 97 | DUF | 3 HR RT | smooth, creamy | — | 699 | A | 6.6 | 6-1 |
| 98 | DUF | 72° C. | smooth, creamy | — | 468 | A | 5.9 | 4-2 |
| 99 | DUF | 85° C. | creamy, runny | — | 137 | U | 1.0 | 0-1 |
| 100 | DUF | F/T | gritty | 182 | 27 | U | 1.0 | 0-1 |
| 101 | DUF | F/T/F/T | gritty | 187 | 0 | U | 1.0 | 0-1 |
| 102 | DUF | 24 HR RT | smooth, creamy | 582 | 904 | A | 6.8 | 6-0 |
| 103 | DUF | 72° C. 24 HR | smooth, creamy | 541 | 812 | A | 6.0 | 6-0 |
| 104 | DUF | 85° C. 24 HR | smooth, creamy | 482 | 809 | A | 5.5 | 6-0 |
| 105 | EWS | 3 HR RT | smooth, rigid, creamy | — | 725 | A | 6.6 | 6-0 |
| 106 | EWS | 72° C. | slimy, lumpy | — | 520 | U | 3.5 | 1-6 |
| 107 | EWS | 85° C. | slimy, lumpy | — | 229 | U | 2.7 | 1-6 |
| 108 | EWS | F/T | gritty | 323 | 96 | U | 1.0 | 0-1 |
| 109 | EWS | F/T/F/T | gritty | 336 | 86 | U | 1.0 | 0-1 |
| 110 | EWS | 24 HR RT | smooth, creamy | 655 | 942 | A | 7.7 | 5-0 |
| 111 | EWS | 72° C. 24 HR | gritty, lumpy | 648 | 853 | U | 5.5 | 2-3 |
| 112 | EWS | 85° C. 24 HR | gritty, lumpy | 638 | 1231 | U | 4.8 | 5-0 |
| 113 | SOP | 3 HR RT | smooth, rigid, creamy | — | 903 | A | 5.9 | 6-0 |
| 114 | SOP | 72° C. | smooth, rigid | — | 580 | A | 6.3 | 6-0 |
| 115 | SOP | 85° C. | smooth, slimy, creamy | — | 199 | U | 5.0 | 2-3 |
| 116 | SOP | F/T | gritty | 332 | 106 | U | 1.0 | 0-1 |
| 117 | SOP | F/T/F/T | gritty | 149 | 57 | U | 1.0 | 0-1 |
| 118 | SOP | 24 HR RT | smooth, creamy | 661 | 1119 | A | 7.3 | 7-0 |
| 119 | SOP | 72° C. 24 HR | smooth, creamy | 614 | 965 | A | 6.8 | 7-0 |
| 120 | SOP | 85° C. 24 HR | gritty, lumpy | 623 | 1498 | U | 3.7 | 1-6 |
| 121 | MIP | 3 HR RT | smooth, creamy | — | 669 | U | 5.5 | 3-2 |
| 122 | MIP | 72° C. | smooth, creamy | — | 427 | U | 4.6 | 2-3 |
| 123 | MIP | 85° C. | smooth, airy | — | 117 | U | 1.0 | 0-1 |
| 124 | MIP | F/T | gritty | 348 | 96 | U | 1.0 | 0-1 |
| 125 | MIP | F/T/F/T | gritty | 261 | 83 | U | 1.0 | 0-1 |
| 126 | MIP | 24 HR RT | smooth | 519 | 820 | A | 7.3 | 4-0 |
| 127 | MIP | 72° C. 24 HR | smooth | 554 | 749 | A | 6.0 | 3-1 |
| 128 | MIP | 85° C. 24 HR | gritty, lumpy | 544 | 1370 | U | 3.3 | 0-4 |
| 129 | SCA | 3 HR RT | smooth, creamy | — | 685 | A | 6.5 | 7-1 |
| 130 | SCA | 72° C. | smooth | — | 568 | A | 5.2 | 8-0 |
| 131 | SCA | 85° C. | smooth, runny | — | 155 | U | 1.0 | 0-1 |
| 132 | SCA | F/T | gritty | 290 | 83 | U | 1.0 | 0-1 |
| 133 | SCA | F/T/F/T | gritty | 128 | 40 | U | 1.0 | 0-1 |
| 134 | SCA | 24 HR RT | smooth, creamy | 641 | 818 | A | 6.4 | 4-0 |
| 135 | SCA | 72° C. 24 HR | creamy | 584 | 721 | A | 5.2 | 4-1 |
| 136 | SCA | 85° C. 24 HR | gritty, lumpy | 514 | 1147 | U | 2.5 | 0-5 |

EXAMPLE 13

A reduced calorie chocolate frosting was prepared using an aqueous dispersion of a fragmented common corn starch hydrolysate from Example 10, above. The dispersion was made by mixing one part of the hydrolysate of Example 10 with three parts of water in a Waring Blender for 8½ minutes. The blender was jacketed with cooling water to maintain the temperature between 60° and 75° C.

The frosting was prepared using the following ingredients and procedure.

| Ingredients | Wt. % |
|---|---|
| Part A | |
| High Fructose Corn Syrup, ISOSWEET ® 5500 (55% fructose d.s.b.)(A. E. Staley Mfg. Co.) | 22.0 |
| Shortening, BETRICING (Van Den Bergh Foods) | 5.30 |
| Mono-, Di-glycerides, DUR-EM 204K (Van Den Bergh Foods) | 0.50 |

-continued

| Ingredients | Wt. % |
|---|---|
| Polysorbate 60, DURFAX 60K | 0.20 |
| (Van Den Bergh Foods) | |
| Vanilla Extract (Virginia Dare) | 0.20 |
| Butter Flavor (Bush Boake Allen) | 0.05 |
| Dispersion of Starch Hydrolysate, 25% d.s. | 25.00 |
| Part B: | |
| Powdered Sugar (12X) | 24.00 |
| Polydextrose K (Pfizer, Inc.) | 10.00 |
| Cold-Water-Swelling Granular Starch, | 4.75 |
| (MIRA-GEL ® 463, A. E. Staley Mfg. Co.) | |
| Cocoa (Hershey) | 4.00 |
| Microcrystalline Cellulose, | 3.50 |
| SOLKA-FLOC BW-300 (James River Corp.) | |
| Salt | 0.40 |
| K Sorbate (Pfizer, Inc.) | 0.10 |
| Total | 100.00 |

Procedure

1. Place ingredients in Part A together in a plastic beaker. Mix with an ULTRA-TURRAX, Model No. SD-15, mixer from Tekmar Co., Inc. (hereinafter "Tekmar mixer" for 2 minutes or until forms a creme. Use variac to control the power. Adjust the power accordingly (i.e., 40% power on step 1, 40% to 60% power on step 2 as the viscosity increases along with the additional solids).

2. Dry blend ingredients in Part B together. Slowly add into the above mixture. Mix with Tekmar mixer for 2 minutes and pack.

EXAMPLE 13A

A reduced calorie chocolate frosting can be prepared from the following ingredients by substantially the same procedure as Example 13, but Part B is prepared substantially as described in Example 56, below, and then added after step 1, whereupon mixing is continued for 1 minute.

| Ingredients | Wt. % |
|---|---|
| Part A | |
| ISOSWEET 5500 | 27.65 |
| Sugar, Powdered 6X | 23.00 |
| Water | 7.00 |
| Shortening (BETRICING Van Den Bergh) | 6.00 |
| Cold-Water-Swelling Starch | 4.15 |
| (MIRA-GEL 463, A. E. Staley) | |
| SANTONE 3-1-SH (Van Den Bergh) | 0.20 |
| Part B | |
| Starch Hydrolysate Dispersion | 13.80 |
| of Run No. 5D (25% d.s.) | |
| Vanilla Extract | 0.20 |
| Butter Flavor | 0.05 |
| Part C | |
| Polydextrose K (Pfizer) | 9.50 |
| Cocoa Powder | 4.00 |
| Cellulose (RC 200, Reed) | 3.50 |
| Salt | 0.10 |
| Potassium Sorbate | 0.10 |
| Sodium Acid Pyrophosphate | 0.05 |
| Total | 100.00 |

EXAMPLE 14

A reduced calorie chocolate frosting was prepared substantially as in Example 13, except the waxy maize starch hydrolysate of Example 9 was used in place of the common corn starch hydrolysate of Example 10.

EXAMPLE 15

A waxy maize starch hydrolysate prepared by the procedure of Example 1 was used to replace a portion of the fat in a creme filling formulation. One part by weight of the waxy maize starch hydrolysate was mixed with three parts by weight of water and fed to a MICROFLUIDIZER operating at 8,000 psi with an inlet temperature of 50° C. The resulting suspension was employed in the formulation set forth below.

| Ingredients | Wt. % |
|---|---|
| Part A | |
| Polydextrose N, 70% Solution (Pfizer, Inc.) | 14.30 |
| ISOSWEET 5500 | 10.00 |
| Part B | |
| Shortening, BETRICING | 6.00 |
| Polyglycerol Monoesters, SANTONE 3-1-S XTR, | 0.50 |
| (Van Den Bergh Foods) | |
| Polysorbate 60, DURFAX 60K | 0.39 |
| Part C | |
| Powdered Sugar (6X) | 42.00 |
| Instant Starch, TENDER-JEL ® H | 2.90 |
| (A. E. Staley Mfg. Co.) | |
| Salt | 0.40 |
| Sodium Stearoyl Lactylate, EMPLEX | 0.10 |
| (American Ingredients Co.) | |
| Butter and Vanilla Flavor, Consumers #18 | 0.40 |
| Part D | |
| Dispersion of Starch Hydrolysate, 20% d.s. | 23.01 |
| Total | 100.00 |

Procedure

1. Place Part A in a beaker and mix on the Tekmar mixer for 1 minute at 50-60% of the variac setting.

2. Heat Part B in microwave to 140°-150° F. and add to Part A. Mix 1 minute at 50-60% of the variac setting.

3. Place Part C in the mixing bowl of a Kitchen Aid mixer, add one-third of the above mixture, and blend 1 minute, speed 4, then scrape bowl.

4. Add another one-third of the liquids and mix 1 minute more, speed 4, then scrape bowl.

5. Add the last portion of liquids and mix 2 minutes, speed 6; 2 minutes, speed 4.

6. Add Part D at room temperature or warmer and mix 30 seconds, speed 4; scrape; mix 4 minutes, speed 6.

EXAMPLE 16

A spoonable salad dressing was prepared using an aqueous dispersion of a waxy maize starch hydrolysate prepared as in Example 2. The aqueous dispersion was prepared as in Example 13.

The spoonable salad dressing was prepared using the following ingredients and procedure.

| Ingredients | Wt. % |
|---|---|
| Part A | |
| Water | 17.0325 |
| White Distilled Vinegar (50 grain) | 17.00 |
| Cider Vinegar (50 grain) | 3.00 |
| ISOSWEET ® 100 Corn Syrup | 15.90 |
| (A. E. Staley Mfg. Co.) | |
| SWEETOSE ® 4300 Corn Syrup | 1.33 |
| (A. E. Staley Mfg. Co.) | |
| Salt | 1.90 |
| Starch, DELTA ™ 7393 SD | 4.00 |
| (A. E. Staley Mfg. Co.) | |
| Mustard Powder | 0.10 |
| Onion Powder | 0.04 |
| Garlic Powder | 0.04 |
| Calcium Disodium EDTA at 75 ppm | 0.0075 |

| Ingredients | Wt. % |
|---|---|
| Part B | |
| Dispersion of Starch Hydrolysate, 25% d.s. | 23.00 |
| Egg Yolk, fresh | 4.50 |
| Lemon Juice | 0.15 |
| Soybean Oil | 12.00 |

Procedure

Part A

1. Combine Part A ingredients with agitation in a swept surface Groen kettle.
2. Heat to 190° F. and hold for 10 minutes.
3. Cool to below 90° F.

Part B

1. Transfer appropriate amount of Part A to a Hobart mixing bowl.
2. Add starch hydrolysate dispersion, egg yolk, and lemon juice into the above paste, mix until smooth.
3. Add oil slowly.
4. Process the resulting mixture through a colloid mill set at 0.026".

EXAMPLE 17

A reduced calorie pourable buttermilk salad dressing was prepared using a dispersion of the waxy maize starch hydrolysate of Example 1 to replace a portion of the oil. The aqueous dispersion of the starch hydrolysate was prepared using the procedure of Example 13. The pourable salad dressing was prepared using the following ingredients and procedure.

| Ingredients | Wt. % |
|---|---|
| Buttermilk | 28.00 |
| Waxy Maize Starch Hydrolysate Dispersion (25% d.s.) | 20.00 |
| Water | 19.70 |
| Soybean Oil | 10.00 |
| Vinegar | 9.25 |
| Seasoning Mix | 5.00 |
| Egg Yolk | 3.00 |
| Sugar | 2.40 |
| Salt | 1.00 |
| Buttermilk Solids | 0.75 |
| Cold-Water-Swelling Starch (MIRA-THIK ® 468, A. E. Staley) | 0.60 |
| Xanthan, KELTROL TF (Kelco) | 0.10 |
| Potassium Sorbate | 0.10 |
| Calcium Disodium EDTA | 75 ppm |
| Total | 100.00 |

Procedure

1. Place buttermilk, starch hydrolysate dispersion, water and egg yolk in a Hobart mixing bowl. Mix at low speed for 2 minutes.
2. Slurry xanthan and MIRA-THIK 468 in soybean oil. Add the slurry into above solution and keep mixing at low speed. Allow to hydrate for 5 minutes.
3. Dry blend seasoning mix, sugar, salt, buttermilk solids, potassium sorbate and calcium disodium EDTA. Add into the above mixture.
4. Add vinegar. Keep mixing for 2 minutes. Pass the dressing through a colloid mill at 0.01 setting.

EXAMPLE 18

A no-oil buttermilk dressing can be prepared in a manner similar to that of Example 17, but with the changes noted below.

| Ingredients | Wt % |
|---|---|
| Buttermilk (1% fat) | 33.50 |
| Water | 24.51 |
| Starch Hydrolysate Dispersion of Run No. 5D (25% d.s.) | 24.00 |
| Vinegar (100 grain, white) | 5.55 |
| Seasoning Mix (Griffith Lab 858-0092) | 4.70 |
| STAR-DRI 10 | 4.00 |
| Sugar | 1.20 |
| Buttermilk Solids (BEATREME 983) | 1.00 |
| CMC (Aqualon 7MF) | 0.70 |
| SOFT-SET | 0.23 |
| Salt | 0.20 |
| Garlic Powder (McCormick) | 0.10 |
| Onion Powder (McCormick) | 0.10 |
| Potassium Sorbate | 0.10 |
| Titanium Dioxide | 0.10 |
| Xanthan (KELTROL T, Kelco) | 0.06 |
| Calcium Disodium EDTA | 75 ppm |
| Total | 100.00 |

Procedure

1. Prepare 25% d.s. dispersion as generally described in Examples 46–49.
2. Scale up materials for 4,000 gram batch. Combine all the dry ingredients together and mix well.
3. Place water and buttermilk in Hobart mixing bowl. Disperse the above dry blend into water and mix with a paddle for 10 minutes at medium speed.
4. Add dispersion and mix for 10 minutes at medium speed.
5. Add vinegar and mix for 1 minute. Process through a colloid mill at 0.02 opening.

EXAMPLE 19

A French dressing containing no oil was prepared using an aqueous dispersion of a waxy maize starch hydrolysate as described in Example 17. The dressing was prepared using the following ingredients and procedure.

| Ingredients | Wt. % |
|---|---|
| Water | 24.20 |
| ISOSWEET 100 Corn Syrup | 23.50 |
| Waxy Maize Starch Hydrolysate Dispersion (d.s.b.) | 15.00 |
| Polydextrose N (70% solution) | 15.00 |
| Vinegar (100 grain, white) | 10.50 |
| Tomato Paste | 8.00 |
| Salt | 2.00 |
| MIRA-THIK 468 | 1.00 |
| Seasoning (Griffith Labs) | 0.30 |
| Mustard Powder | 0.20 |
| Seasoning (McCormick) | 0.10 |
| Xanthan, KELTROL TF (Kelco) | 0.10 |
| Aquaresin Paprika | 0.05 |
| Calcium Disodium EDTA | 75 ppm |
| Total | 100.00 |

Procedure

1. Place water, ISOSWEET 100, starch hydrolysate dispersion, polydextrose N solution and tomato paste in a Hobart mixing bowl. Mix at low speed for 2 minutes.
2. Blend all the dry ingredients together and disperse into the above solution. Keep mixing at low speed. Allow to hydrate for 5 minutes.
3. Add vinegar and Aquaresin paprika into the above mixture. Mix for 2 minutes.
4. Pass the dressing through a colloid mill at 0.01 setting.

EXAMPLE 20

An oil-free French dressing can be prepared as follows.

| Ingredients | Wt. % |
|---|---|
| Water | 36.00 |
| High Fructose Corn Syrup (ISOSWEET 100, A. E. Staley) | 25.00 |
| Starch Hydrolysate Dispersion of Run No. 5D (25% d.s.) | 22.00 |
| Vinegar (white, 100 grain) | 10.10 |
| Tomato Paste | 3.50 |
| Salt | 2.00 |
| MIRA-THIK 468 | 0.60 |
| Seasoning Mix (Griffith 912-0135) | 0.30 |
| Mustard Powder | 0.20 |
| Seasoning (McCormick #F34037) | 0.10 |
| Xanthan (Kelco) | 0.10 |
| Paprika, ground | 0.05 |
| Yellow #6 (10% solution) | 0.05 |
| Calcium Disodium EDTA | 75 ppm |
| Total | 100.00 |

Procedure

1. Blend dry ingredients together thoroughly, then disperse into water in a Hobart Mixing bowl. Mix with a paddle at low speed for 10 minutes.
2. Add ISOSWEET, starch hydrolysate dispersion (prepared substantially as described in Examples 47–49), yellow #6 solution and tomato paste. Continue mixing for 10 minutes.
3. Add vinegar and mix for 2 minutes.
4. Process the dressing through a colloid mill at 0.013 setting.

EXAMPLE 21

From the following ingredients, a no-oil Dijon Vinaigrette can be prepared as follows:

| Ingredients | Wt. % |
|---|---|
| Water | 49.50 |
| Starch Hydrolysate Dispersion of Run No. 5D (25 d.s.) | 14.00 |
| Vinegar (white, 100 grain) | 14.00 |
| Sugar | 6.50 |
| Dijon Mustard (Nabisco) | 6.00 |
| Lemon Juice | 6.00 |
| Salt | 2.35 |
| Spices (McCormick #F30378) | 1.00 |
| Xanthan (KELTROL TF, Kelco) | 0.05 |
| Red Bell Pepper, Dried | 0.05 |
| Potassium Sorbate | 0.04 |
| Color | 0.01 |
| Calcium Disodium EDTA | 75 ppm |
| Total | 100.00 |

Procedure

1. Place water in a beaker.
2. Blend all the dry ingredients together and disperse into the water. Mix with a Servodyne mixer (Model E-650) for 5 minutes.
3. Add dispersion, mustard, vinegar, and lemon juice. Keep mixing for 10 minutes.

EXAMPLE 22

A margarine was prepared having one-third of the oil replaced by an aqueous dispersion of a waxy maize starch hydrolysate of Example 1, said aqueous dispersion prepared using a MICROFLUIDIZER as described above employing an inlet temperature of 50° C. and a pressure of 8,000 psi. The margarine was prepared using the following ingredients and procedure.

| Ingredients | Wt. % |
|---|---|
| Part A | |
| Margarine Oil (Staley 400-03) | 53.3 |
| Monoglycerides, MYVEROL 18-92 (Eastman Chemicals) | 0.5 |
| Lecithin, single bleached (ADM) | 0.3 |
| Part B | |
| Potassium Sorbate | 0.1 |
| Calcium Disodium EDTA | 0.0075 |
| Sodium chloride | 1.0 |
| Water | 18.0 |
| Part C | |
| Antioxidant, TENOX 2 (Eastman Chemicals) | 0.02 |
| Beta-Carotene 30% (Roche Chemicals) | 0.005 |
| Ottens Aritificial Butter Oil #2964 | 0.015 |
| Part D | |
| 25% Dispersion of Starch Hydrolysate | 26.67 |

Procedure

1. Combine Part A ingredients in a 2 liter stainless steel beaker and warm in a water bath set at 124° F. Stir vigorously using mechanical stirring.
2. When the Part A solution has reached 122°–124° F., add the ingredients in Part C to the Part A solution.
3. Prepare a solution of the ingredients in Part B.
4. Add Part B solution and Part D dispersion to the solution from step 2 and mix well.
5. When the step 4 solution reaches 122° F., mix with a Tekmar mixer for 5 minutes on a variac setting of 80/140.
6. Transfer mixture to a precooled Kitchen Aid heavy duty mixer bowl equipped with ice bath accessory.
7. Mix, at as fast a speed as possible without losing material, using the mixing blade type paddle.
8. When the temperature of the mixture reaches 50°–55° F., transfer mixture back to the stainless steel beaker and homogenize with the Tekmar mixer at setting 80/140 for approximately 5 minutes.
9. Transfer mixture to containers and cool.

EXAMPLE 23

An imitation margarine was prepared having one-half the oil replaced by a waxy maize starch hydrolysate dispersion as described in Example 22. The margarine was prepared using the following ingredients and the same procedure as Example 22.

| Ingredients | Wt. % |
|---|---|
| Part A | |
| Margarine Oil (Staley 400-03) | 20 |
| Monoglycerides, MYVEROL 18-92 (Eastman Chemicals) | 0.5 |
| Lecithin, Single Bleached (ADM) | 0.3 |
| Part B | |
| Potassium Sorbate | 1.0 |
| Calcium Disodium EDTA | 0.0075 |
| Sodium Chloride | 1.0 |
| Xanthan Gum | 0.05 |
| Water | 18.05 |
| Part C | |
| Antioxidant, TENOX 2 (Eastman Kodak) | 0.02 |
| Beta-Carotene 30% (Roche Chemicals) | 0.005 |
| Ottens Artificial Butter Oil #2964 | 0.015 |
| Part D | |
| 25% Dispersion of Starch Hydrolysate | 60 |

Procedure

The procedure described in Example 22 was used without modification.

EXAMPLE 24

Reduced-Oil Table Spreads

A reduced oil table spread was made by a two-stage procedure as set forth below.

| Stage 1: Multicomponent Dispersion for 40% Oil Table Spread | |
|---|---|
| Ingredients | Wt. % |
| Part A | |
| Deionized Water (total; % includes starch hydrolysate moisture) | 76.060 |
| Potassium Sorbate | 0.166 |
| Calcium Disodium EDTA | 0.012 |
| Salt | 1.662 |
| Emulsifier (MYVATEX, Texture Lite, Eastman) | 0.5 |
| Part B | |
| Starch Hydrolysate Powder, Run No. 6F (d.s.) | 21.60 |
| Total | 100.00 |

Procedure

1. Heat deionized water to 42° C. (less water in starch hydrolysate powder).
2. Put water in a beaker and start stirring vigorously with Servodyne.
3. Add other Part A ingredients while continuing vigorous stirring (MYVATEX, Texture Lite is a mixture of propylene glycol monoesters, mono- and diglycerides and sodium stearoyl lactylate).
4. Run through MICROFLUIDIZER with inlet temperature of 37° C., pressure of 15,000 psi, and resulting outlet temperature of 59° C.

Stage 2: Reduced Calorie Table Spread—40% Oil

| Ingredients | Wt. % |
|---|---|
| Part A | |
| Margarine Oil + TENOX* | 39.82 |
| MYVEROL 18-92 (Eastman) | 0.25 |
| MYVEROL 18-99 (Eastman) | 0.25 |
| Lecithin (single bleached) | 0.30 |
| Beta-Carotene (0.3% in oil)** | 0.20 |
| Flavor (Firmenich 57.752/A) | 0.07 |
| Part B | |
| Multicomponent Dispersion from Stage 1 | 59.11 |
| Total | 100.00 |

*A 0.05% solution of TENOX (Eastman) in oil (STALEY 400-03).
**A 0.3% solution of beta-carotene (Roche) in oil (STALEY 400-03)

Procedure to Make 500 Grams

1. Prepare creme as directed.
2. Place Part A ingredients in a 600 ml plastic beaker and heat to 60° C. on a steam bath.
3. Place Part B ingredients in a 600 ml glass beaker and heat to 50°-60° C. in a water bath.
4. Start stirring Part A vigorously with a Servodyne mixer.
5. Add Part B to Part A while continuing vigorous stirring.
6. Blend with Tekmar mixer for 4 minutes at variac setting of 70.
7. Transfer to an ice jacketed Kitchen Aid mixer and stir on speed 4 with a cake paddle until the temperature is 10°-12° C.
8. Transfer to a 600 ml plastic beaker and mix with the Tekmar mixer until a smooth uniform texture is obtained.
9. Refrigerate.

EXAMPLE 25

A second reduced oil table spread, containing only 20% oil, was prepared as follows.

Stage 1: Multicomponent Dispersion for 20% Oil

| Ingredients | Wt. % |
|---|---|
| Part A | |
| Deionized Water (total) | 76.43 |
| Xanthan Gum | 0.089 |
| Potassium Sorbate | 0.12 |
| Calcium Disodium EDTA | 0.009 |
| Salt | 1.252 |
| MYVATEX (Texture Lite) | 0.5 |
| Part B | |
| Starch Hydrolysate Powder, Run No. 6F (d.s.) | 21.6 |
| Total | 100.00 |

Procedure

1. Put water in blender and stir at variac setting of 70.
2. Add other Part A ingredients and continue stirring for 1 minute.
3. Transfer to plastic beaker and stir vigorously with Servodyne.
4. Add dispersion powder slowly while stirring vigorously.
5. Run through MICROFLUIDIZER as immediately above.

Stage 2: Reduced Calorie Table Spread—20% Oil

| Ingredients | Wt. % |
|---|---|
| Part A | |
| Margarine Oil + TENOX* | 19.82 |
| MYVEROL 18-92 (Eastman) | 0.25 |
| MYVEROL 18-99 (Eastman) | 0.25 |
| Lecithin (single bleached) | 0.30 |
| Beta-Carotene (0.3% in oil)** | 0.20 |
| Flavor (Firmenich 57.752/A) | 0.07 |
| Part B | |
| Multicomponent Dispersion | 79.11 |
| Total | 100.00 |

*A 0.05% solution of TENOX (Eastman) in oil (STALEY 400-03).
**A 0.3% solution of beta-carotene (Roche) in oil (STALEY 400-03).

Procedure to Make 500 Grams

1. Prepare creme as directed.
2. Place Part A ingredients in a 600 ml plastic beaker and heat to 60° C. on a steam bath.
3. Place Part B ingredients in a 600 ml glass beaker and heat to 50°-60° C. in a water bath.
4. Start stirring Part A vigorously with a Servodyne mixer.
5. Add Part B to Part A while continuing vigorous stirring.
6. Blend with Tekmar mixer for 4 minutes at variac setting of 70.
7. Transfer to an ice jacketed Kitchen Aid mixer and stir on speed 4 with a cake paddle until the temperature is 10°-12° C.
8. Transfer to a 600 ml plastic beaker and mix with the Tekmar mixer until a smooth uniform texture is obtained.
9. Refrigerate.

EXAMPLE 26

Another reduced oil table spread, containing only 20% oil, was prepared as follows:

Stage 1: Multicomponent Dispersion for 20% Oil Table Spread

| Ingredients | Wt. % |
|---|---|
| Part A | |
| Deionized Water (total) | 76.48 |
| Potassium Sorbate | 0.12 |
| Calcium Disodium EDTA | 0.01 |
| Salt | 1.25 |
| Emulsifier (MYVATEX Texture Lite, Eastman) | 0.50 |
| Part B | |
| Starch Hydrolysate Powder, Run No. 6F (d.s.) | 21.64 |
| Total | 100.00 |

Procedure
1. Heat water to 42° C.
2. Put water in a beaker and start stirring vigorously with Servodyne.
3. Add other Part A ingredients while continuing vigorous stirring.
4. Run through MICROFLUIDIZER as above.

Stage 2: Reduced Calorie Table Spread—20% Oil

| Ingredients | Wt. % |
|---|---|
| Part A | |
| Margarine Oil + TENOX* | 19.82 |
| MYVEROL 18–92 (Eastman) | 0.25 |
| MYVEROL 18–99 (Eastman) | 0.25 |
| Lecithin (single bleached) | 0.30 |
| Beta-Carotene (0.3% in oil)** | 0.20 |
| Flavor (Firmenich 57.752/A) | 0.07 |
| Part B | |
| Multicomponent Dispersion | 79.11 |
| Total | 100.00 |

*A 0.05% solution of TENOX (Eastman) in oil (STALEY 400-03).
**A 0.3% solution of beta-carotene (Roche) in oil (STALEY 400-03).

Procedure to Make 500 Grams
1. Prepare creme as directed in separate formula.
2. Place Part A ingredients in a 600 ml plastic beaker and heat to 50°–60° C. on a steam bath.
3. Place Part B ingredients in a 600 ml glass beaker and heat to 50°–60° C. in a water bath.
4. Start stirring Part A vigorously with a Servodyne mixer.
5. Add Part B to Part A while continuing vigorous stirring.
6. Blend with Tekmar mixer for 4 minutes at variac setting of 80.
7. Transfer immediately to an ice jacketed Kitchen Aid mixer and stir on speed 4 with a cake paddle until the temperature is 10°–12° C.
8. Refrigerate.

EXAMPLE 27

A table spread, 20% oil, can be prepared without the use of a MICROFLUIDIZER type homogenizer, or extended Waring blender use, by the following two-stage procedure.

Stage 1: Multicomponent Dispersion

| Ingredients | Wt. % |
|---|---|
| Part A | |
| Deionized Water | 75.03 |
| Xanthan Gum | 0.089 |
| Potassium Sorbate | 0.12 |
| Calcium Disodium EDTA | 0.009 |
| Salt | 1.252 |
| MYVATEX Texture Lite | 0.5 |
| Part B | |
| Starch Hydrolysate Powder, Run No. 6J (d.s.) | 23.0 |
| Total | 100.00 |

Procedure
1. Heat water to 50° C.
2. Put water in beaker and stir vigorously with Emil Greiner mixer.
3. Pre-mix dry ingredients by hand.
4. Add dry ingredients while continuing stirring.
5. Mix with Tekmar mixer about 2 minutes.

Stage 2: Reduced Calorie Table Spread—20% Oil

| Ingredients | Wt. % |
|---|---|
| Part A | |
| Margarine Oil + TENOX* | 19.82 |
| MYVEROL 18–92 (Eastman) | 0.25 |
| MYVEROL 18–99 (Eastman) | 0.25 |
| Lecithin (single bleached) | 0.30 |
| Beta-Carotene (0.3% in oil)** | 0.20 |
| Flavor (Firmenich 57.752/A) | 0.07 |
| Part B | |
| Multicomponent Dispersion | 79.11 |
| Total | 100.00 |

*A 0.05% solution of TENOX (Eastman) in oil (STALEY 400-03).
**A 0.3% solution of beta-carotene (Roche) in oil (STALEY 400-30).

Procedure to Make 500 Grams
1. Prepare creme as directed in separate formula.
2. Place Part A ingredients in a 600 ml plastic beaker and heat to 60° C. on a steam bath.
3. Place Part B ingredients in a 600 ml glass beaker and heat to 50°–60° C. in a water bath.
4. Start stirring Part A vigorously with a Servodyne mixer.
5. Add Part B to Part A while continuing vigorous stirring.
6. Blend with Tekmar mixer for 4 minutes at variac setting of 80.
7. Transfer immediately to an ice jacketed Kitchen Aid mixer and stir on speed 3 with a cake paddle until the temperature is 7°–10° C.
8. Refrigerate.

EXAMPLE 28

Reduced Fat Mousse

A reduced fat mousse was prepared by the following two-stage procedure.

Stage 1: Aqueous Dispersion Preparation

| Ingredients | Wt. % |
|---|---|
| Part A | |
| Deionized Water (total) | 79.9 |
| Potassium Sorbate | .1 |
| Washed Starch Hydrolysate Powder, | 20.0 |

-continued

| Ingredients | Wt. % |
|---|---|
| Run No. 6F (d.s.) | |
| Total | 100.00 |

Procedure
1. Heat water to 42° C.
2. Stir water vigorously with Servodyne mixer.
3. Add starch hydrolysate powder and sorbate while continuing vigorous stirring.
4. Process through MICROFLUIDIZER with a pressure of 14,000-16,000 psi.
5. Refrigerate dispersion if not using immediately.

Stage 2: Reduced Fat/Calorie Chocolate Mousse

| Ingredients | Wt. % |
|---|---|
| Part A | |
| Water | 33.09 |
| DUR-LO | .83 |
| Emulsifier (MYVATEX Texture Lite, Eastman) | .33 |
| Part B | |
| Crystalline Fructose (KRYSTAR, A. E. Staley) | 9.11 |
| Polydextrose K (Pfizer) | 5.79 |
| Corn Syrup Solids (STAR-DRI 24R, A. E. Staley) | 4.96 |
| Non-Fat Dry Milk | 4.14 |
| Cocoa (Van Houton 10/12 Tula) | 3.33 |
| Starch (DURA-GEL, A. E. Staley) | 1.65 |
| Sucrose | 1.65 |
| Dried Egg whites | 1.65 |
| Cocoa (Van Houton 10/12 Natural) | 1.64 |
| Sodium Bicarbonate | .30 |
| Artificial Vanilla Powder (Universal Flavors #P-1148) | .097 |
| Part C | |
| Dispersion from Stage 1 (20% d.s.) | 31.44 |

Procedure to Make 500 Grams
1. Prepare dispersion as in Stage 1.
2. Scale Part A ingredients into a 250 ml beaker, Part B ingredients into a 600 gram beaker and Part C ingredients into a 250 ml beaker.
3. Place Part A ingredients in a blender and blend on variac setting of 50 until smooth.
4. Add Part B ingredients and blend on variac setting of 90 until smooth.
5. Add Part C ingredient and blend on variac setting of 100 until smooth.
6. Transfer mixture into a Kitchen Aid mixer (K5SS) and mix with a cake paddle on speed 8 for two minutes.
7. Refrigerate.

EXAMPLE 29

A reduced fat mousse was prepared by the general procedure of Example 28, but with the following ingredients.

| Ingredients | Wt. % |
|---|---|
| Part A | |
| Water | 33.36 |
| DUR-LO | .84 |
| MYVATEX | .34 |
| Part B | |
| KRYSTAR | 9.18 |
| Polydextrose K (Pfizer) | 5.00 |
| Cocoa (Van Houton 10/12 Tula) | 3.36 |
| Cocoa (Van Houton 10/12 Natural) | 1.66 |
| STAR-DRI 24R | 5.00 |
| Non-Fat Dry Milk | 4.17 |
| Sucrose | 1.67 |
| DURA-GEL | 1.67 |
| Dried Egg Whites | 1.67 |
| Sodium Bicarbonate | .29 |
| Artificial Vanilla Powder | .097 |
| Part C | |
| Starch Hydrolysate Dispersion, Run No. 6F (20 d.s.) | 31.70 |

EXAMPLE 30

A reduced-fat mousse can be prepared in one stage, using the procedure of Stage 2 of Example 29, from the following ingredients. This one-stage procedure does not employ a MICROFLUIDIZER type of homogenizer or entail extended use of a Waring blender.

| Ingredients Part A | pbw |
|---|---|
| Artificial Vanilla Flavor (Universal Flavors #P-1148) | .587 |
| Starch Hydrolysate Dry Powder, Run No. 6J | 38 |
| Water | 343.3 |
| Polydextrose K (Pfizer) | 35 |
| KRYSTAR | 55 |
| Sucrose | 10 |
| Non-Fat Dry Milk | 25 |
| Egg Whites | 10 |
| DURA-GEL | 10 |
| STAR-DRI 24 | 30 |
| Cocoa (Van Houton 10/12 Tula) | 20.1 |
| Cocoa (Van Houton 10/12 Natural) | 9.9 |
| Sodium Bicarbonate | 1.79 |
| MYVATEX | 2 |
| DUR-LO | 5 |

EXAMPLE 31

A frozen novelty having a low fat content was prepared using an aqueous dispersion of the waxy maize starch hydrolysate of Example 12, said dispersion prepared as in Example 13. The frozen dessert was prepared using the following ingredients and procedure.

| Ingredients | Wt. % |
|---|---|
| Milk Fat | 1.2 |
| Milk Solids Non-Fat | 13.5 |
| Sucrose | 12.0 |
| Corn Syrup Solids (35 DE) | 8.5 |
| Stabilizer (Continental Colloids, Inc.) | 0.4 |
| Dispersion of Starch Hydrolysate | 5.4 |
| Water | 59.0 |

Procedure
1. Mix water, milk, dispersion of starch hydrolysate and dry ingredients with rapid mixing.
2. Heat to 105° F. and cool; homogenize and pasteurize (HTST 185° F./25 seconds).
3. Store overnight at refrigerator temperature.
4. Add vanilla flavor to the mix (McCormick Vanilla V-401/1 fold) at a level of 15 ml/10 lbs. mix.
5. Freeze the mix using a pilot scale continuous ice cream freezer.

EXAMPLE 32

A frozen novelty was prepared substantially as described in Example 31, except the amount of aqueous dispersion of starch hydrolysate was decreased to 2.5 wt. %, the amount of water was correspondingly increased, and the other ingredients were premixed, homogenized, pasteurized and stored overnight prior to addition of the aqueous dispersion of starch hydrolysate. Rapid mixing upon addition of the aqueous dispersion of the starch hydrolysate served to disperse the starch hydrolysate in the mix.

EXAMPLE 33

A French onion dip containing an imitation sour cream was prepared using an aqueous dispersion of a waxy maize starch hydrolysate prepared as in Example 1, said dispersion prepared using a MICROFLUIDIZER as generally described herein. The imitation sour cream was prepared using the following ingredients and procedure.

|  | Wt. % |
|---|---|
| Sour Cream Base | |
| Sour Cream (Meadow Gold) | 29.83 |
| 25% Dispersion of Starch Hydrolysate with 0.1% Potassium Sorbate | 39.79 |
| Lactic Acid, 88% | 0.54 |
| Water | 23.27 |
| Non-Fat Dry Milk, Low Heat (Land O'Lakes) | 5.97 |
| Xanthan Gum | 0.20 |
| Salt | 0.20 |
| Sodium Citrate | 0.20 |
| Total | 100.00 |
| Sour Cream Based Dip | |
| Seasoning Mix #859-0033 (Griffith Labs) | 6.02 |
| Sour Cream Base | 93.98 |
| Total | 100.00 |

Procedure
  Sour Cream Base
  1. Mix all dry ingredients.
  2. Add lactic acid to water. Mix well.
  3. Add dry ingredients. Mix 2-3 minutes.
  4. Add dispersion of starch hydrolysate. Mix 2-3 minutes.
  5. Add sour cream. Mix 3-5 minutes.
  Sour Cream Based Dip
  6. Add seasoning mix to sour cream base from step 5.

EXAMPLES 34–38

A series of imitation sour creams were prepared. Examples 34 and 35 were prepared as in Example 33, except each starch hydrolysate aqueous dispersion contained 0.1% potassium sorbate and Example 35 employed an aqueous dispersion of the starch hydrolysate at only 20% solids, rather than 25% solids. In Examples 36–38, the dry starch hydrolysate, which had not been mechanically disintegrated in aqueous dispersion with a MICROFLUIDIZER or Waring blender, was mixed with the other dry ingredients of the mix. The ingredients, procedures, and results are set forth below.

| Example | Wt. (grams) | | | | |
|---|---|---|---|---|---|
| Ingredients | 34 | 35 | 36 | 37 | 38 |
| Sour Cream | 200.00 | 200.00 | 200.00 | — | 300.00 |
| 25% Dispersion of Starch Hydrolysate | 266.80 | — | — | — | — |
| Dry Starch Hydrolysate | — | — | 66.70 | 70.00 | 100.50 |
| 20% Dispersion of Starch Hydrolysate | — | 266.80 | — | — | — |
| Lactic Acid, 88% | 3.60 | 3.60 | 3.60 | 3.60 | 3.60 |
| Water | 156.08 | 155.81 | 356.28 | 492.61 | 300.15 |
| Non-Fat Dry Milk, Low Heat (Land O'Lakes) | 40.00 | 40.00 | 40.00 | 40.00 | — |
| Salt | 1.34 | 1.34 | 1.34 | 1.34 | 1.34 |
| Xanthan Gum | 1.34 | 1.61 | 1.34 | 1.61 | — |
| Sodium Citrate | 1.34 | 1.34 | 1.34 | 1.34 | 1.34 |
| Sour Cream Powder (BEATREME 1755) | — | — | — | 35.00 | — |
| Sour Cream Powder (BEATREME 2622) | — | — | — | 20.00 | — |
| 2% Milk | — | — | — | — | 305.55 |

Procedure for 34 and 35
  1. Mix dry ingredients and add to mixing water.
  2. Mix 2-3 minutes. Add lactic acid.
  3. Mix in dispersion of starch hydrolysate. Mix 3-5 minutes.
  4. Add sour cream. Mix 3-5 minutes.
  5. Refrigerate in tubs.
Procedure for 36 and 37
  1. Mix all ingredients.
  2. Heat water in microwave to 57°-60° C.
  3. Add dry ingredients. (Temperature lowered to 54° C.)
  4. Put through MICROFLUIDIZER at 8,000 psi (final product temperature—52° C.).
  5. Add sour cream. Refrigerate.
Result
  Sample 37 clogged MICROFLUIDIZER; however, consistency was very smooth, flavor OK.
  Sample 36 had consistency like 20% dispersion of starch hydrolysate before adding sour cream.
Procedure for 38
  1. Mix water and milk. Heat to 55°-57° C. in microwave on high.
  2. Add dry ingredients and lactic acid. (Temperature lowered to 52° C.)
  3. Put through MICROFLUIDIZER at 8,000 psi.
  4. Add sour cream. Refrigerate.
Result
  Prior to adding sour cream, product was very thick like 25% dispersion of starch hydrolysate and very smooth. It was still fairly translucent. Outlet temperature was 67° C.

EXAMPLES 39–42

A series of low fat/reduced calorie/sour creams were prepared as follows.

| Example | Wt. (grams) | | | |
|---|---|---|---|---|
| Ingredients | 39 | 40 | 41 | 42 |
| Water | 352.75 | 353.50 | 353.60 | 349.60 |
| Starch Hydrolysate Powder, Run No. 4B | 52.25 | 52.25 | 50.00 | 50.00 |
| Non-Fat Dry Milk, Low Heat | 33.55 | 33.55 | 35.00 | 35.00 |
| BEATREME 1755 | 11.20 | 11.20 | 11.00 | 11.00 |
| BEATREME 2622 | 22.35 | 22.35 | 22.00 | 22.00 |
| Sweet Whey | 12.50 | 12.50 | 12.50 | 12.50 |
| Starch (LO-TEMP ® 452, A. E. Staley) | 4.85 | 4.85 | — | 4.00 |
| Lactic Acid, 88% | 2.25 | 2.00 | 2.50 | 2.50 |
| Xanthan Gum | 1.25 | 1.25 | .50 | .50 |
| Citric Acid | 1.50 | 1.00 | — | — |
| Salt | 1.00 | 1.00 | 1.00 | 1.00 |
| Sodium Citrate | 1.00 | 1.00 | 1.00 | 1.00 |
| K Sorbate | .50 | .50 | .50 | .50 |
| Sour Cream Flavor | .45 | .45 | .40 | .40 |

| Example | Wt. (grams) | | | |
|---|---|---|---|---|
| Ingredients | 39 | 40 | 41 | 42 |
| Emulsifier (DUR-LO) | — | — | 10.00 | 10.00 |

Procedure
1. Mix all dry ingredients.
2. Add to water. Mix 3-5 minutes.
3. Microfluidize at 14,500-15,000 psi at outlet temperature of 50° C.
4. Refrigerate.

EXAMPLE 43

Chocolate Syrup and Fudge Topping

| Ingredients | Syrup % by wt. | Fudge % by wt. |
|---|---|---|
| Water | 62.14 | 57.16 |
| Non-Fat Dry Milk, Low Heat | 9.27 | 11.27 |
| Dutch Cocoa #4001.7 (Van Houten) | 7.00 | 7.51 |
| Starch Hydrolysate Powder, Run No. 4B | 3.00 | 6.00 |
| Polydextrose Solution, 70%, pH 5-8, Pfizer A, dissolved and neutralized | 10.00 | 10.00 |
| KRYSTAR 300, Crystalline Fructose | 2.50 | 2.50 |
| Natural Cocoa (Van Houten) | 4.71 | 2.20 |
| LO-TEMP 452 | 0 | 2.00 |
| Aspartame | 0.06 | 0.06 |
| Chocolate Flavor, IFF 13550072 | 0.40 | 0.40 |
| Xanthan Gum | 0.10 | 0.10 |
| Vanilla Flavor #P-1148 (Universal Flavors) | 0.10 | 0.10 |
| Sodium Benzoate | 0.10 | 0.10 |
| K Sorbate | 0.06 | 0.06 |
| Total | 100.00 | 100.00 |

Procedure
1. Mix dry ingredients in Kitchen Aid mixer equipped with paddle 2-3 minutes.
2. Add dry mix to water and polydextrose solution.
3. Mix 3-5 minutes in Kitchen Aid mixer equipped with paddle (speed 4).
4. Strain thru U.S. 20 screen (optional depending on opening of high shear mixer).
5. Pass through MICROFLUIDIZER at 14,500-15,000 psi without prior heating. Desired output temperature 48°-50° C. Seal warm. (The desired output temperature could be achieved by feeding room temperature slurry using high pressure setting with the septum fully open.)
6. Store in plastic bottle or glass jar.
7. Refrigerate after first opening.
8. Serve chilled or at room temperature over ice cream for syrup. Fudge topping can be heated then served.

EXAMPLE 44

A cheese spread can be prepared using an aqueous dispersion of the waxy maize starch hydrolysate of Example 1 to replace the fat, the dispersion being prepared as in Example 13. The ingredients and procedure that can be used are set forth as follows.

| Ingredients | Wt. % |
|---|---|
| Part A | |
| Cheese Powder, DPD 260-7 (Mid-America Farms) | 20.70 |
| Cheese Powder, #36129 (Mid-America Farms) | 2.95 |
| Non-Fat Dry Milk | 5.42 |
| Lactic Acid Powder, "Purac Powder H" | 0.50 |
| (Purac, Inc.) | |
| MIRA-GEL 463 | 0.92 |
| MIRA-THIK 468 | 0.65 |
| Citric Acid | 0.26 |
| Sorbic Acid | 0.15 |
| Onion Powder (McCormick) | 0.10 |
| Water | 28.05 |
| 0.01% Solution of Red #40 (Warner Jenkinson) | 0.20 |
| 5.0% Solution of #08031 (Warner Jenkinson) | 0.20 |
| Salt | 0.52 |
| Part B | |
| Starch Hydrolysate of Example 1 | 9.80 |
| Water | 29.40 |
| | 100.00 |

Procedure
1. Combine Part B in Waring blender as in Example 7.
2. Combine ingredients of Part A in Kitchen Aid mixer with wire whip until smooth (add water in 3 portions).
3. Add Part B to mixer and blend together until smooth.

EXAMPLE 45

A cheese cake was prepared in which a portion of the cream cheese was replaced with an aqueous dispersion of a starch hydrolysate prepared from an alkaline washed waxy maize starch as described in Example 11. The ingredients and procedure used are as follows.

| Ingredients | Wt. % |
|---|---|
| Part A | |
| Starch Hydrolysate | 9.00 |
| Water | 27.00 |
| METHOCEL A4M (Dow Chemical) | .50 |
| Part B | |
| Cream Cheese (Kraft) | 24.24 |
| Part C | |
| Bakers Special Granulated Sugar | 11.00 |
| TENDERFIL ® 8 (A. E. Staley Mfg. Co.) | 1.50 |
| Cream Cheese Flavor, F21704 (McCormick-Stange) | .75 |
| Vanilla Cream, 464174 (Universal Flavors) | .20 |
| Natural Cream Flavor, 462507 (Universal Flavors) | .20 |
| Salt | .20 |
| Soy Protein Isolate, MIRA-PRO ® 111 (A. E. Staley Mfg. Co.) | .40 |
| Xanthan, KELTROL T (Kelco) | .10 |
| Lactic Acid Powder, BEATREME 3463 (Beatrice Co.) | .40 |
| Part D | |
| Butter Flavor, Art. 5-11380, (Bush, Boake, and Allen) | .10 |
| Egg Whites, Frozen (Echo Lake Farm Produce) | 6.60 |
| Whole Eggs, Frozen (Echo Lake Farm Produce) | 4.70 |
| Corn Syrup, NETCO ® 7300 (A. E. Staley Mfg. Co.) | 2.40 |
| Fresh Sour Cream | 5.00 |
| Lemon Juice (Borden) | 1.43 |
| Water | 4.28 |
| Total | 100.00 |

Procedure
1. Heat water in Part A to 140° F. Add to 14 speed Oster blender, add dispersion of starch hydrolysate and blend until thick. Add the METHOCEL and mix until uniform.
2. Place cream cheese in bowl of Kitchen Aid mixer and cream with a paddle until smooth (2 minutes at speed 4). Then add Part A and cream smooth (2 minute at speed 4).

3. Dry blend Part C and add to the above and mix smooth (2 minutes at speed 4).

4. Add Part D and mix smooth (2 minutes at speed 4).

5. Pour 630 grams into an 8 inch graham cracker crust.

6. Place in a 350° F. oven for 40-50 minutes until a toothpick inserted into the center of the cake comes out clean. (NOTE: Place a pan of water into the oven for moisture prior to baking.)

7. Refrigerate or freeze as required.

EXAMPLE 46

An aqueous dispersion was prepared by fragmenting the starch hydrolysate of a waxy maize starch as in Example 2 with an emulsifier. The ingredients and procedure used are set forth below, along with the ingredients and procedure for a chocolate frosting using the emulsifier/starch hydrolysate blend.

Emulsified/Starch Hydrolysate Blend Dispersion

| Ingredients | Wt. % |
|---|---|
| Water | 69 |
| Waxy Maize Starch Hydrolysate of Example 2 | 26 |
| Emulsifier, DUR-LO ™ (Van Den Bergh) | 5 |
| | 100 |

Procedure

1. Combined and blended in Stephan mixer on low speed for a period of 15 seconds.

2. Heating to 50° C. was also done in the Stephan mixer.

3. Product was then transferred to the Gaulin type homogenizer and homogenized at 7,000 psi. The exit temperature was 60° C.

EXAMPLE 46 (Continued)

A chocolate frosting was prepared using the above product and the following ingredients and procedures.

| Ingredients | Wt. % |
|---|---|
| Part A | |
| Shortening, BETRICING | 4.3 |
| Emulsifier, DUR-EM | 0.3 |
| Polysorbate, DURFAX | 0.2 |
| Part B | |
| ISOSWEET 5500 | 20.0 |
| Emulsifier/Starch Hydrolysate Blend Dispersion | 26.4 |
| Vanilla Extract | 0.5 |
| Part C | |
| Powdered Sugar (12×) | 25.2 |
| Polydextrose K | 10.0 |
| Cocoa | 4.0 |
| MIRA-GEL 463 | 4.6 |
| SOLKA-FLOC, alpha cellulose | 4.0 |
| Salt | 0.4 |
| K Sorbate | 0.1 |
| Total | 100.0 |

Procedure

1. Part A is heated to melting and blended with high shear mixer, then added to Part B, producing a homogeneous blend.

2. Part C is slowly added and sheared on the same high shear mixer (such as a Tekmar) until homogeneous.

VI. COMPARATIVE STUDY OF GRANULAR HIGH AMYLOSE STARCH HYDROLYSATE, GRANULAR WAXY MAIZE STARCH TOTAL HYDROLYSATE, AND GRANULAR WAXY MAIZE STARCH HYDROLYSATE

Various food products were made using an aqueous dispersion of one of each of the above-noted starch hydrolysate products. The food products made with these different starch hydrolysates were: 1) table spreads (40% and 20% oil), 2) ready-to-spread frosting, 3) spoonable salad dressing, 4) no-oil French dressing, 5) buttermilk salad dressing, 6) cheese spread, 7) cheesecake, 8) creme filling for snack cakes, and 9) Danish pastry. The ingredients were kept the same in the washed waxy and high amylose formulas, but the sugar and salt levels were adjusted, where possible, in the "unwashed" waxy (total hydrolysate) formulas to compensate for the additional saccharides and salt in this hydrolysate.

The texture, mouthfeel and flavor of these products were evaluated by an informal, untrained panel of A. E. Staley Manufacturing Company employees.

EXAMPLES 47-49

Aqueous Dispersion of Fragmented Starch Hydrolysate

The aqueous dispersion of the fragmented starch hydrolysates employed in Examples 50 to 76 were prepared according to the following general procedure:

| Ingredients | Example 47 Washed Waxy | Example 48 High Amylose | Example 49 Unwashed Waxy |
|---|---|---|---|
| Washed Waxy Starch Hydrolysate, Run No. 5D Powder (d.s.) | 25.0 | — | — |
| High Amylose Starch Hydrolysate, Run No. 1C Powder (d.s.) | — | 25.0 | — |
| Unwashed Waxy Starch Total Hydrolysate, Run No. 5E(TH) Powder (d.s.) | — | — | 40.0 |
| Potassium Sorbate | 0.1 | 0.1 | 0.1 |
| Deionized Water (total; % includes moisture of starch hydrolysate powder) | 74.9 | 74.9 | 59.9 |
| Total | 100.0% | 100.0% | 100.0% |

Procedure

1. Heat water to 42° C.

2. Stir water vigorously with Servodyne mixer.

3. Add powder and sorbate while continuing vigorous stirring.

4. Process through MICROFLUIDIZER (Model M-110T) with pressure of 14,000-16,000 psi.

5. MICROFLUIDIZER output temperature was typically 54° C.

The washed waxy dispersion appeared organoleptically typical. The color was white and the flavor was fairly bland, with a slight corny to cardboardy flavor. The flavor was judged to be the best of the three starch hydrolysate dispersions.

The high amylose dispersion was a slightly brighter white than the waxy dispersion, and had a bitter and rancid flavor. The texture of the high amylose dispersion was more rigid than the washed waxy dispersion.

The unwashed waxy dispersion had a light gray color and a long pasty texture. The flavor of the unwashed dispersion was dominated by salt, but there was also a sweetness and a hint of bitter and corny.

Yield stresses of the washed waxy and high amylose dispersions (25% d.s.) were 1,737 pascals and 1,824 pascals, respectively, at two days after dispersion production. The yield stress of the 40% d.s. unwashed waxy dispersion was 760 pascals at two days after production. (These yield stress values would be lower for 20% d.s. dispersions.)

EXAMPLES 50–55

Reduced Calorie Table Spread

Reduced calorie table spreads (with 40% oil) were prepared from the ingredients set forth below by the general procedure set forth below.

| Ingredients | Example 50 Washed Waxy | Example 51 High Amylose | Example 52 Unwashed Waxy |
|---|---|---|---|
| Part A | | | |
| Margarine Oil (with antioxidant) | 39.82 | 39.82 | 39.82 |
| MYVEROL 18-99 (Eastman) | 0.25 | 0.25 | 0.25 |
| MYVEROL 18-92 (Eastman) | 0.25 | 0.25 | 0.25 |
| Lecithin (single bleached) | 0.30 | 0.30 | 0.30 |
| Beta-Carotene (0.3% in corn oil) | 0.25 | 0.25 | 0.25 |
| Flavor (Firmenich 57.752/A) | 0.07 | 0.07 | 0.07 |
| Part B | | | |
| Potassium Sorbate | 0.06 | 0.06 | 0.06 |
| Calcium Disodium EDTA | 75 ppm | 75 ppm | 75 ppm |
| Salt | 1.20 | 1.20 | 0.08 |
| Distilled Water | 17.80 | 17.80 | 18.92 |
| Part C | | | |
| Washed Waxy Dispersion (25% d.s.) | 40.00 | — | — |
| High Amylose Dispersion (25% d.s.) | — | 40.00 | — |
| Unwashed Waxy Dispersion (40% d.s.) | — | — | 40.00 |
| Total | 100.00% | 100.00% | 100.00% |

Procedure to Make 500 Grams

1. Place Part A ingredients in a 600 ml plastic beaker and heat to 60° C. on a steam bath. (Margarine oil is a 0.05% solution of TENOX (Eastman) in corn oil (STALEY 400-03).)
2. Place Part B ingredients in a 250 ml plastic beaker and heat to 50°-60° C. in a microwave oven.
3. Start stirring Part A vigorously with a Servodyne mixer.
4. Pour Part B into Part A while continuing vigorous stirring.
5. Add Part C to the beaker while continuing vigorous stirring.
6. Blend with Tekmar (ULTRA-TURREX, SD-45) for 4 minutes at variac setting of 70.
7. Transfer to an ice jacketed Kitchen Aid mixer and stir in speed 2 with a cake paddle until the temperature is 7°-10° C.
8. Transfer to a 600 ml plastic beaker and mix with the Tekmar mixer until a smooth uniform texture is obtained.
9. Refrigerate.

Calculated moisture levels for the table spreads were washed waxy, 47.8%; high amylose, 47.8%; and unwashed waxy, 43.0%.

The 40% oil table spreads were organoleptically evaluated with the following results. (Less sodium chloride was added to the table spread containing a dispersion of total hydrolysate.)

Washed Waxy—Good flavor. Texture is acceptable but slightly softer and not quite as smooth as full fat margarine. The appearance after spreading on hot toast was good but slightly wetter than a full fat margarine. Texture and flavor after freezing and thawing were the same as for fresh.

High Amylose—Flavor had a slightly bitter or rancid aftertaste. The intensity of this undesirable flavor was probably low enough that the product is still acceptable. The texture was firmer and smoother and better than the 40% oil washed waxy product. The appearance after spreading on hot toast was the same as for the washed waxy version. When fresh, this was the most well liked, overall, of the three table spreads. After freezing and thawing, the texture and appearance were curdled and grainy and wet; the product was totally unacceptable.

Unwashed Waxy—Flavor was less salty than in the washed starch hydrolysate table spreads. There was a slight off flavor. Texture was softer and not as smooth as in the washed waxy hydrolysate product but still acceptable. The appearance after spreading on hot toast was nearly identical to a full fat margarine. The release from the mouth was more rapid than in the washed hydrolysate spreads. After freezing and thawing the texture was the same as when fresh but the flavor was more sweet.

Reduced calorie table spreads (with 20% oil) were prepared as follows.

| Ingredients | Example 53 Washed Waxy | Example 54 High Amylose | Example 55 Unwashed Waxy |
|---|---|---|---|
| Part A | | | |
| Margarine Oil (with antioxidant) | 19.82 | 19.82 | 19.82 |
| MYVEROL 18-99 (Eastman) | 0.25 | 0.25 | 0.25 |
| MYVEROL 18-92 (Eastman) | 0.25 | 0.25 | 0.25 |
| Lecithin (single bleached) | 0.30 | 0.30 | 0.30 |
| B-Carotene (0.3% in corn oil) | 0.25 | 0.25 | 0.25 |
| Flavor (Firmenich 57.752/A) | 0.07 | 0.07 | 0.07 |
| Part B | | | |
| Xanthan Gum | 0.07 | 0.07 | 0.07 |
| Potassium Sorbate | 0.04 | 0.04 | 0.04 |
| Calcium Disodium EDTA | 75 ppm | 75 ppm | 75 ppm |
| Salt | 1.20 | 1.20 | 1.20 |
| Distilled Water | 17.74 | 18.94 | 18.94 |
| Part C | | | |
| Washed Waxy Dispersion (25% d.s.) | 60.00 | — | — |
| High Amylose Dispersion (25% d.s.) | — | 60.00 | — |
| Unwashed Waxy Dispersion (40% d.s.) | — | — | 60.00 |
| Total | 100.00% | 100.00% | 100.00% |

Procedure to Make 500 Grams

1. Place Part A ingredients in a 600 ml plastic beaker and heat to 60° C. on a steam bath. (Margarine oil is a 0.05% solution of antioxidant (TENOX, Eastman) in oil (STALEY 400-03).)
2. Weigh 20% more of Part B than needed and put in blender. Blend at variac setting of 70 for 2 minutes, then weigh the amount of this solution that is needed into a 250 ml plastic beaker.

3. Heat to 50°-60° C. in a microwave oven.

4. Start stirring Part A vigorously with a Servodyne mixer.

5. Pour Part B into Part A while continuing vigorous stirring.

6. Heat Part C to 50°-60° C. in a water bath.

7. Add Part C to the beaker while continuing vigorous stirring.

8. Blend with Tekmar (ULTRA-TURREX, SD-45) for 4 minutes at variac setting of 70.

9. Transfer to an ice jacketed Kitchen Aid mixer and stir in speed 2 with a cake paddle until the temperature is 7°-10° C.

10. Transfer to a 600 ml plastic beaker and mix with the Tekmar mixer until a smooth uniform texture is obtained.

11. Refrigerate.

Calculated moisture levels for the table spreads were 62.7% for each of the washed waxy and high amylose and 54.9% for the unwashed waxy.

The 20% oil table spreads were evaluated with the following results.

Washed Waxy—Flavor was good, about the same as at 40% oil. The texture was more pasty than in any of the 40% oil products but still acceptable. The appearance after spreading on hot toast was about the same as for the 40% oil washed waxy spread. After freezing and thawing, the product lost some oil. The texture was more pasty than when fresh and the flavor was not quite as strong.

High Amylose—Flavor had a strong bitter and rancid aftertaste which made the product unacceptable. The texture was firmer and smoother and overall better than the waxy spread's texture at this oil level. The appearance after spreading on hot toast was about the same as for the 40% oil high amylose spread. After freezing and thawing, the product lost much oil and had a curdled grainy appearance and texture.

Unwashed Waxy—Flavor was less salty than the washed hydrolysate products. There was a slight bitter or metallic aftertaste. The texture was very soft and rendered the product unacceptable. Release from the mouth was very rapid. The appearance after spreading on hot toast was wet and pasty, the worst of all six spreads tested. After freezing and thawing, the product lost some oil. The texture was more pasty than when fresh and the flavor was sweeter.

EXAMPLES 56–58

Reduced Calorie Chocolate Frosting

Reduced calorie chocolate frostings were prepared by the following general procedure.

| Ingredients | Example 56 Washed Waxy | Example 57 High Amylose | Example 58 Unwashed Waxy |
|---|---|---|---|
| Part A | | | |
| ISOSWEET 5500 (A. E. Staley) | 27.65 | 27.65 | 27.65 |
| Sugar, Powdered 6× | 23.00 | 23.00 | 23.00 |
| Water | 7.00 | 7.00 | 9.00 |
| Shortening (BETRICING) | 6.00 | 6.00 | 6.00 |
| MIRA-GEL (A. E. Staley) | 4.15 | 4.15 | 4.25 |
| Emulsifier (SANTONE 3-1-SH) | 0.20 | 0.20 | 0.20 |
| Part B | | | |
| Washed Waxy Dispersion (25% d.s.) | 13.80 | — | — |
| High Amylose Dispersion (25% d.s.) | — | 13.80 | — |
| Unwashed Waxy Dispersion (40% d.s.) | — | — | 13.80 |
| Vanilla Extract (Virginia Dare) | 0.20 | 0.20 | 0.20 |
| Butter Flavor (Virginia Dare #891) | 0.05 | 0.05 | 0.05 |
| Part C | | | |
| Polydextrose K (Pfizer) | 10.00 | 10.00 | 10.00 |
| Cocoa Powder | 4.00 | 4.00 | 4.00 |
| Cellulose (RC 3200, Reed Chemical) | 3.50 | 3.50 | 3.50 |
| Salt | 0.10 | 0.10 | 0.10 |
| Potassium Sorbate | 0.10 | 0.10 | 0.10 |
| Sodium Acid Pyrophosphate | 0.05 | 0.05 | 0.05 |
| Total | 100.00% | 100.00% | 100.00% |

Procedure to Make 400 Grams

1. Place Part A in a 600 ml plastic beaker, mix with a Tekmar mixer (ULTRA-TURREX, SD-45) at variac setting of 60.

2. Prepare the dispersion of Part B as described in Examples 47–49.

3. Combine ingredients from Part B and add to Part A. Keep mixing at the same speed until smooth.

4. Dry blend the ingredients in Part C together, then add into the above creme and keep mixing at variac setting of 70 for 3 minutes or until smooth.

5. Immediately pack in a 16 oz. jar after the frosting is prepared. One jar is good to frost a 9 inch double layer cake.

The frostings were organoleptically evaluated with the following results. (Formulas were the same for the washed waxy and high amylose frostings, but no salt and less sugar were added in the unwashed waxy formulation.)

Washed Waxy—Flavor was the best among all three frostings. The texture was slightly soft.

High Amylose—Had the best texture among all three frostings; it was short and not stringy. However, the flavor was not as clean as the other two. Mouthfeel was close to that of the washed waxy version.

Unwashed Waxy—Had a long texture and slightly gummy, heavy mouthfeel. Slightly off flavor and a saltier taste although no salt was added in the formula. The amount of salt from the unwashed hydrolysate was more than what was added to the above two frostings. It also appeared darker in color which may result from the darker creme of unwashed waxy hydrolysate.

EXAMPLES 59–61

Reduced Calorie Spoonable Dressing

Reduced calorie spoonable dressings were prepared generally as follows.

| Ingredients | Example 59 Washed Waxy | Example 60 High Amylose | Example 61 Unwashed Waxy |
|---|---|---|---|
| Part A | | | |

|  | Example | | |
|---|---|---|---|
| Ingredients | 59 Washed Waxy | 60 High Amylose | 61 Unwashed Waxy |
| Water | 28.78 | 28.78 | 28.78 |
| DELTA ® 7393 SD Starch (A. E. Staley) | 2.85 | 2.85 | 2.85 |
| Salt | 2.00 | 2.00 | 0.40 |
| Xanthan (KELTROL T, Kelco) | 0.20 | 0.20 | 0.20 |
| Mustard Powder (McCormick) | 0.20 | 0.20 | 0.20 |
| Garlic Powder (McCormick) | 0.07 | 0.07 | 0.07 |
| Onion Powder (McCormick) | 0.07 | 0.07 | 0.07 |
| Paprika, Ground (McCormick) | 0.01 | 0.01 | 0.01 |
| Calcium Disodium EDTA | 75 ppm | 75 ppm | 75 ppm |
| Part B | | | |
| Washed Waxy Dispersion (25% d.s.) | 23.00 | — | — |
| High Amylose Dispersion (25% d.s.) | — | 23.00 | — |
| Unwashed Waxy Dispersion (40% d.s.) | — | — | 23.00 |
| ISOSWEET 100 (A. E. Staley) | 21.00 | 21.00 | 21.00 |
| Soybean Oil (Wesson) | 12.00 | 12.00 | 12.00 |
| Vinegar (white, 100 grain) | 7.15 | 7.15 | 7.15 |
| Water | — | — | — |
| Cider Vinegar (50 grain) | 2.50 | 2.50 | 2.50 |
| Lemon Juice (Borden) | 0.16 | 0.16 | 0.16 |
| Yellow #5 (2% solution) | 0.01 | 0.01 | 0.01 |
| Total | 100.00% | 100.00% | 100.00% |

Procedure to Make 4,000 Grams

1. Prepare dispersion of starch hydrolysate as described in Examples 47–49.
2. Place the ingredients of Part A in a scraped-surface steam kettle, cook up o 180° F. and hold up 5 minutes. Cool down to 90° F. and transfer to a Hobart mixing bowl.
3. Add soybean oil to the above paste in the Hobart and mix in medium speed until smooth.
4. Add dispersion and ISOSWEET 100 into the above and keep mixing in medium speed until smooth.
5. Add vinegar, lemon juice, color solution (and water), mix until smooth and process through a colloid mill at 0.013 setting.

The dressings were evaluated with the following results. (Formulas were the same for washed waxy and high amylose dressings, but less salt and corn syrup were added to the dressing containing unwashed hydrolysate to compensate for the additional salt and sugars in the unwashed waxy dispersion.)

Washed Waxy—The dressing had a good, clean flavor. It also had a smooth and creamy mouthfeel, and a smooth, short texture.

High Amylose—Had a short and smooth texture. However, the mouthfeel and flavor were not as good as that of the one made with washed waxy hydrolysate. It had a slightly chalky mouthfeel, and a rancid off flavor.

Unwashed Waxy—The texture was too soft and gummy. The mouthfeel was weak. This dressing melted away in the mouth much faster than the other two dressings although it actually has the highest solid content. The flavor was good but was sweeter than the other two dressings.

EXAMPLES 62–64

No-Oil French Dressing

No-oil French dressings were prepared generally as follows.

|  | Example | | |
|---|---|---|---|
| Ingredients | 62 Washed Waxy | 63 High Amylose | 64 Unwashed Waxy |
| Water | 36.25 | 36.25 | 40.80 |
| ISOSWEET 100 (A. E. Staley) | 25.00 | 25.00 | 22.00 |
| Washed Waxy Dispersion (25% d.s.) | 22.00 | — | — |
| High Amylose Dispersion (25% d.s.) | — | 22.00 | — |
| Unwashed Waxy Dispersion (40% d.s.) | — | — | 23.00 |
| Vinegar (white, 100 grain) | 10.00 | 10.00 | 10.00 |
| Tomato Paste | 3.50 | 3.50 | 3.50 |
| Salt | 2.00 | 2.00 | 2.00 |
| MIRA-THIK 468 (A. E. Staley) | 0.60 | 0.60 | 0.60 |
| Seasoning Mix (Griffith 912-0135) | 0.30 | 0.30 | 0.30 |
| Seasoning Mix (McCormick #F34037) | 0.10 | 0.10 | 0.10 |
| Xanthan (KELTROL T, Kelco) | 0.10 | 0.10 | 0.10 |
| Mustard Powder (McCormick) | 0.05 | 0.05 | 0.05 |
| Paprika, Ground (McCormick) | 0.05 | 0.05 | 0.05 |
| Yellow #6 (10% solution) | 0.03 | 0.03 | 0.03 |
| Yellow #5 (2% solution) | 0.02 | 0.02 | 0.02 |
| Calcium Disodium EDTA | 75 ppm | 75 ppm | 75 ppm |
| Total | 100.00% | 100.00% | 100.00% |

Procedure to Make 4,000 Grams

1. Prepare dispersion of starch hydrolysate as described in Examples 47–49.
2. Scale up materials for 4,000 gram batch.
3. Place water and ISOSWEET 100 in a Hobart C-100 mixing bowl.
4. Blend all the dry ingredients together and disperse into the above solution. Mix with a paddle in medium speed for 10 minutes or until smooth.
5. Add tomato paste and dispersion; mix for 10 minutes in medium speed.
6. Add vinegar and color solution, then mix for one minute. Homogenize through a colloid mill at 0.013 setting.

The viscosity (Brookfield RV, Spindle #4, 20 rpm) of the dressings is set forth below:

| Dispersion | Viscosity (Brookfield RV #4, 20 rpm) |
|---|---|
| Washed Waxy | 4,150 cps |
| High Amylose | 3,700 cps |
| Unwashed Waxy | 3,200 cps |

Washed waxy and high amylose formulas were the same, but less corn syrup and salt were added in the unwashed waxy dressing to compensate for the salt and saccharides in the dispersion.

Washed Waxy—Smooth and creamy texture and mouthfeel. Flavor was good, no off flavor was noticed.

High Amylose—Mouthfeel was very close to that of the one made with washed waxy hydrolysate. The texture seemed to be heavier than the washed waxy version although the viscosity is lower. A rancid off flavor was noticeable. The flavor profile was actually the worst among all three French dressings.

Unwashed Waxy—This dressing had a darker color than the others which was probably caused by the dark greyish color of the unwashed waxy dispersion. Viscosity was the lowest among all three dressings, the texture and mouthfeel were also the weakest.

EXAMPLES 65-67

Fat-Free Buttermilk Dressing

Fat-free buttermilk dressings were prepared generally as follows.

| Ingredients | Example | | |
|---|---|---|---|
| | 65 Washed Waxy | 66 High Amylose | 67 Unwashed Waxy |
| Bittermilk (1%, Dean Foods) | 30.00 | 30.00 | 30.00 |
| Water | 27.28 | 27.28 | 27.78 |
| Washed Waxy Dispersion (25%% d.s.) | 20.00 | — | — |
| High Amylose Dispersion (25% d.s.) | — | 20.00 | — |
| Unwashed Waxy Dispersion (40% d.s.) | — | — | 20.00 |
| Vinegar (white, 100 grain) | 8.20 | 8.20 | 8.20 |
| High Fructose Corn Syrup (42% fructose, ISOSWEET 100,, A. E. Staley) | 6.50 | 6.50 | 5.00 |
| Seasoning Mix (Griffith 8580092) | 4.00 | 4.00 | 4.00 |
| Soybean oil (Wesson) | 2.00 | 2.00 | 2.00 |
| Salt | 1.00 | 1.00 | — |
| Cold-Water Swelling Starch (MIRA-THIK 468, A. E. Staley) | 0.50 | 0.50 | 0.50 |
| Xanthan Gum (KELTROL TF, Kelco) | 0.12 | 0.12 | 0.12 |
| Garlic Powder (McCormick) | 0.10 | 0.10 | 0.10 |
| Onion Powder (McCormick) | 0.10 | 0.10 | 0.10 |
| Flavoring (VICO BF-5, A. E. Staley) | 0.10 | 0.10 | 10.0 |
| Potassium Sorbate | 0.10 | 0.10 | 0.10 |
| Calcium Disodium EDTA | 75 ppm | 75 ppm | 75 ppm |
| Total | 100.00% | 100.00% | 100.00% |

Procedure to Make 4,000 Grams

1. Prepare dispersion of starch hydrolysate as described in Examples 47-49.
2. Scale up materials for 4,000 gram batch.
3. Place water, buttermilk and ISOSWEET 100 in Hobart C-100 mixing bowl.
4. Blend the dry ingredients together and disperse into the above solution. Mix with a paddle in medium speed for 10 minutes.
5. Add oil and dispersion, mix in medium speed for 10 minutes.
6. Add vinegar and keep mixing for 1 more minute. Process through a colloid mill at 0.013 setting.

The viscosity (Brookfield RV, Spindle #2, 40 rpm) of the dressing is set forth below:

| Dispersion | Viscosity (Brookfield RV #4, 20 rpm) |
|---|---|
| Washed Waxy | 6,000 cps |
| High Amylose | 5,750 cps |
| Unwashed Waxy | 3,200 cps |

The dressings were organoleptically evaluated with the following results. (Formulas were the same for washed waxy and high amylose dressings, but were slightly modified for the unwashed waxy. Less sugar and no salt were added to the unwashed waxy dressing.)

Washed Waxy—The flavor profile was good, no off flavor noticeable. It had a creamy mouthfeel and smooth texture.

High Amylose—Strong rancid off flavor, smooth but slightly gelling texture although the viscosity is lower than that of the waxy version. Mouthfeel close to that of the dressing containing the washed waxy hydrolysate.

Unwashed Waxy—Slightly sweeter than the above dressings, no off flavor noticed. Texture was smooth, but slightly low in viscosity. Mouthfeel was close to the other two dressings.

EXAMPLES 68-70

Reduced Calorie Cheese Spread

Reduced calorie cheese spreads were prepared generally as follows.

| Ingredients | Example | | |
|---|---|---|---|
| | 68 Washed Waxy | 69 High Amylose | 70 Unwashed Waxy |
| Part A | | | |
| Water | 29.62 | 29.63 | 29.63 |
| Non-Fat Dry Milk | 5.42 | 5.42 | 5.42 |
| 5.0% Solution, #08031 (Warner-Jenkinson) | 0.15 | 0.15 | 0.15 |
| 0.1% Solution of Red #40 (Warner-Jenkinson) | 0.16 | 0.16 | 0.16 |
| Dipotassium Phosphate | 0.20 | 0.20 | 0.20 |
| Part B | | | |
| Cheese Powder DPD260-7 (Mid-America Farms) | 22.50 | 22.50 | 22.50 |
| TENDER-JEL ® 419 (A. E. Staley) | 0.92 | 0.92 | 0.92 |
| MIRA-THIK 468 (A. E. Staley) | 0.65 | 0.65 | 0.65 |
| Salt, Flour | 0.32 | 0.32 | 0.32 |
| Part C | | | |
| Washed Waxy Dispersion (25% d.s.) | 39.30 | — | — |
| High Amylose Dispersion (25% d.s.) | — | 39.30 | — |
| Unwashed Waxy Dispersion (40% d.s.) | — | — | 39.30 |
| Part D | | | |
| Lactic Acid, 80% | 0.34 | 0.34 | 0.34 |
| Citric Acid, Powdered | 0.26 | 0.26 | 0.26 |
| Sorbic Acid, Powdered | 0.15 | 0.15 | 0.15 |
| Total | 100.00% | 100.00% | 100.00% |

Procedure to Make 1,000 Grams

1. Prepare the dispersion of starch hydrolysate for Part C as described above in Examples 47-49
2. Blend Part A together with a hand wire whip.
3. Place Part B in a mixing bowl, add Part A, and using a flat paddle, blend until smooth.
4. Transfer the above to a plastic beaker and add Part C. Mix these on a Tekmar (ULTRA-TURREX, SD-45) mixer until homogenous.
5. Add Part D and mix one minute more on the Tekmar mixer.

The only fat in this formula (7.5%) comes from the cheese powder. The spreads made with washed hydrolysate used dispersions at 25% d.s. The spread made with unwashed waxy hydrolysate was 40% d.s. Salt (NaCl) addition was the same for all three spreads. The spreads were evaluated with the following results.

Washed Waxy—Flavor was good, with no off flavors. Texture was acceptable, but slightly pasty.

High Amylose—This spread had a strong off flavor which made it unacceptable. The texture of this spread was smoother, creamier, and preferred over the texture of the washed waxy spread.

Unwashed Waxy Hydrolysate—This spread had a strong off flavor which made it unacceptable. The texture was soft and pasty relative to the washed waxy spread.

EXAMPLES 71-73

Reduced Calorie Cheesecake

Reduced calorie cheesecakes were prepared generally as follows.

| | Example | | |
|---|---|---|---|
| | 71 | 72 | 73 |
| | Washed | High | Unwashed |
| Ingredients | Waxy | Amylose | Waxy |
| Part A | | | |
| Cream Cheese | 24.24 | 24.24 | 24.24 |
| Washed Waxy Dispersion (25% d.s.) | 36.00 | — | — |
| High Amylose Dispersion (25% d.s.) | — | 36.00 | — |
| Unwashed Waxy Dispersion | — | — | 36.00 |
| Part B | | | |
| NETO ® 7300 (A. E. Staley) | 2.40 | 2.40 | 2.40 |
| Sour Cream | 5.00 | 5.00 | 5.00 |
| Lemon Juice (Borden) | 1.00 | 1.00 | 1.00 |
| Water | 14.00 | 14.00 | 14.00 |
| Part C | | | |
| Bakers Special Granulated Sugar | 8.00 | 8.00 | 8.00 |
| KRYSTAR ® 300 (A. E. Staley) | 2.50 | 2.50 | 2.50 |
| TENDER-FIL ® 8 (A. E. Staley) | 2.00 | 2.00 | 2.00 |
| Cream Cheese Flavor (McCormick-Stange #F21704) | 0.75 | 0.75 | 0.75 |
| Vanilla Creamy (Universal Flavor #464174) | 0.20 | 0.20 | 0.20 |
| Natural Cream Flavor Universal Flavor #462507) | 0.20 | 0.20 | 0.20 |
| Salt | 0.20 | 0.20 | 0.20 |
| MICRO-PRO ® 111 (Gunther) | 0.40 | 0.40 | 0.40 |
| Xanthan Gum | 0.10 | 0.10 | 0.10 |
| Lactic Acid Powder, BEATREME 3463 (Beatrice) | 0.40 | 0.40 | 0.40 |
| METHOCEL A4M (Dow) | 0.50 | 0.50 | 0.50 |
| Egg White Powder P-11 (Henningsen) | 1.26 | 1.26 | 1.26 |
| Dried While Egg Yolks Y-1-FF (Henningson) | 0.85 | 0.85 | 0.85 |
| Total | 100.00% | 100.00% | 100.00% |

Procedure to Make 1,000 Grams—(Using Kitchen Aid Mixer (Model K5SS))

1. Prepare dispersion for Part A as described above in Examples 47-49.
2. Place part A in mixing bowl and, using a flat paddle, mix 4 minutes in speed 4.
3. Combine Part B in a plastic bag and add while mixing in low. Mix 2 minutes in speed 4.
4. Preblend Part C and add to the above mixture and mix for 1 minute in speed 2, scrape, and mix for 1 minute more.
5. Pour 695 grams into an 8 inch graham cracker crust.
6. Bake in a 350° F. oven for 50-60 minutes until a toothpick inserted into the center of the cake comes out clean.

The dispersion replaced 60% of the cream cheese in these formula and therefore 60% of the fat. These cheese cakes were organoleptically evaluated with the following results.

Washed Waxy—Best of all three formulas in texture and flavor.

High Amylose—Thickest before bake and after bake. Texture firm and somewhat cheese-like and unacceptable. The flavor was different, but acceptable.

Unwashed Waxy—Unacceptable in texture because it was too soft. Unacceptable in color because it was slightly grey. Flavor was poor.

EXAMPLES 74-76

Reduced Calorie Creme Filling

Reduced calorie creme fillings were prepared generally as follows.

| | Example | | |
|---|---|---|---|
| | 74 | 75 | 76 |
| | Washed | High | Unwashed |
| Ingredients | Waxy | Amylose | Waxy |
| Part A | | | |
| Polydextrose N, 70% Solution | 14.30 | 14.30 | 14.30 |
| ISOSWEET ® 5500 HFCS (A. E. Staley) | 10.00 | 10.00 | 10.00 |
| Butter and Vanilla Flavor #18 (Consumers) | 0.40 | 0.40 | 0.40 |
| Washed Waxy Dispersion (25% d.s.) | 23.01 | — | — |
| High Amylose Dispersion (25% d.s.) | — | 23.01 | — |
| Unwashed Waxy Dispersion (40% d.s.) | — | — | 23.41 |
| Part B | | | |
| BETRICING (Van Den Bergh Foods) | 6.00 | 6.00 | 6.00 |
| SANTONE 3-1-S XTR (Van Den Bergh Foods) | 0.50 | 0.50 | 0.50 |
| DURFAX 60K (Van Den Bergh Foods) | 0.39 | 0.39 | 0.39 |
| Part C | | | |
| Powder Sugar 6× | 42.90 | 42.90 | 42.90 |
| INSTANT TENDER-JEL H (A. E. Staley) | 1.90 | 1.90 | 1.90 |
| Salt | 0.40 | 0.40 | 0.40 |
| Potassium Sorbate | 0.10 | 0.10 | 0.10 |
| EMPLEX (American Ingredients Co.) | 0.10 | 0.10 | 0.10 |
| Total | 100.00% | 100.00% | 100.00% |

Procedure

1. Prepare the dispersion for Part A as described above in Examples 47-49.
2. Place Part A in a beaker and mix on the Tekmar mixer for 1 minute at variac setting of 50-60%.
3. Heat Part B to 140°-150° F. and add to Part A. Mix 1 minute on the Tekmar mixer at a variac setting of 50-60%.
4. Place Part C in the mixing bowl and add ½ of the above liquid mixture. Using a wire whip, blend 1 minute in speed 4 on the Kitchen Aid mixer.
5. Add the remaining portion of liquids and mix 3 minutes in speed 6 to a specific gravity of 0.60.

The creme fillings were organoleptically evaluated with the following results.

Washed Waxy—Good flavor and texture.

High Amylose—Thicker than waxy. The consistency and texture were preferred over the unwashed and washed waxy.

Unwashed Waxy—unacceptable because the texture was too soft, poor flavor, and slightly grey color.

EXAMPLES 77-79

Fat-Free Danish Pastry

Fat-free Danish pastries were prepared as follows.

|  | Example | | |
|---|---|---|---|
| Ingredients | 77<br>Washed<br>Waxy | 78<br>High<br>Amylose | 79<br>Unwashed<br>Waxy |
| Part A - Dough Stage | | | |
| All Purpose Flour,<br>4× Patent (Pillsbury) | 39.424 | 39.424 | 39.424 |
| Vital Wheat Gluten | 0.89 | 0.89 | 0.89 |
| Yeast (Fermipan) | 0.56 | 0.56 | 0.56 |
| Sugar | 8.06 | 8.06 | 8.06 |
| Salt | 0.63 | 0.63 | 0.63 |
| Egg White Solids P-11<br>(Henningsen) | 1.01 | 1.01 | 1.01 |
| Egg Shade, #08038<br>(Warner-Jenkinson) | 0.002 | 0.002 | 0.002 |
| GFS (Kelco) | 0.08 | 0.08 | 0.08 |
| DUR-LO (Van Den<br>Bergh Foods) | 2.51 | 2.51 | 2.51 |
| Danish Flavor #14<br>(Consumers) | 0.62 | 0.62 | 0.62 |
| Water | 26.214 | 26.214 | 26.214 |
| Total | 80.00% | 80.00% | 80.00% |
| Part B - Roll-in | | | |
| Water | 6.945 | 6.945 | 10.84 |
| ISOSWEET 100<br>(A. E. Staley) | 6.945 | 6.945 | — |
| Potassium Sorbate | 0.02 | 0.02 | 0.02 |
| Washed Waxy Dispersion<br>(25% d.s.) | 5.09 | — | — |
| High Amylose Dispersion<br>(25% d.s.) | — | 5.09 | — |
| Unwashed Waxy Dispersion<br>(40% d.s.) | — | — | 5.14 |
| DUR-LO (Van Den<br>Bergh Foods) | 1.00 | 1.00 | 1.00 |
| Total | 100.00% | 100.00% | 100.00% |

Procedure to Make 1,000 Grams of Roll-In

1. Place water and HFCS in a beaker.

2. Stir water and HFCS vigorously with Servodyne mixer.

3. Add hydrolysate powder and sorbate while continuing vigorous stirring.

4. Add melted DUR-LO to the mixer and mix until uniform.

5. Place beaker under Tekmar mixer (ULTRA-TURREX, SD-45) for 1-2 minutes to insure the absence of lumps.

6. Process through MICROFLUIDIZER, as described above, with pressure of 14,000-15,000 psi.

7. Refrigerate until use in the Danish.

Procedure to Make 6 Pounds of Dough

1. Place all ingredients of the dough stage into the mixing bowl and mix 1 minute in speed 1. Then mix 16 minutes more in speed 2.

2. Remove the dough from the mixer and let rest 30 minutes.

3. Sheet the dough 3 times as long as wide and about ½ to ¾ of an inch thick. Spread the roll-in over ⅔ of the dough (roll-in is rolled in at a rate of 4 ounces per pound of dough). Fold the uncovered third over the center third and then fold the remaining third over it. Roll it as was done before spotting it with roll-in; i.e., three times as long as wide and ½ to ¾ in thick. Fold it in thirds; place on pre-chilled pan and in a dough retarder (refrigerator) where it should relax for 30 minutes.

4. Repeat this rolling, folding and relaxing process twice more to allow dough to age six hours or more before makeup into desired end product. Keep dough under refrigeration as required to keep the dough temperature between 65°-70° F. during the roll-in process.

5. Allow the dough to set overnight before making up.

Dough Makeup

1. Cut a strip of dough from the previous days run. Roll it approximately 8 inches wide and ⅜ of an inch thick.

2. Cut strips of dough ⅜ of an inch wide. Twist and curl them into a snail shape.

3. Brush on a 60/40 blend of egg whites and water and place in the proof box (set at 80% R.H. and 108° F.).

4. Proof until the dough loses its spring when touched. Then place the rolls in the oven and bake at 375° F. for 15-16 minutes.

5. As the rolls come from the oven, spray them with a 10% solution of potassium sorbate and then brush on a 80/20 solution of SWEETOSE 4300 and water.

All roll-in formulas were produced on the MICROFLUIDIZER. The washed waxy and high amylose both contained a 50/50 blend of water and HFCS for the liquid portion of the roll-in. Because of the soluble fraction contained in the unwashed waxy, no HFCS was added to that roll-in. All roll-ins contained 5% DUR-LO, mono- and diglycerides. The products were made into individual Danish shapes for evaluations.

The Danish pastries were organoleptically evaluated with the following results.

Washed Waxy—This product exhibited good texture and a much longer shelf life than the high amylose. It was tender even up to 14 days with no flavor problems.

High Amylose—This product was similar to a standard Danish in its shelf life characteristics. It only lasted about 5 days. There were no flavor problems.

Unwashed Waxy—This product was unique compared to the other two products in that the dough was stickier, but the layers of dough were more distinct in the finished product. We would like to see more layer separation in our waxy control.

EXAMPLES 80 AND 81

Two routes for making an octenyl succinated fragmented starch hydrolysate were investigated. Waxy maize starch was reacted with octenyl succinic anhydride and then hydrolyzed. Alternatively, a waxy maize starch was octenyl succinated after hydrolysis.

Two lots of octenyl succinated waxy starch were prepared using 3% by weight of octenyl succinic anhydride (the FDA limit). One lot was reacted overnight at room temperature, the second lot for 2.5 hours at room temperature giving 2.52% and 2.40% substitution, respectively. The second lot was then acid hydrolyzed at 37% solids, 60° C. and 0.608 meq/g acid concentration. Samples were taken at 10.5 and 12 hours. The batch was neutralized at 12 hours and isolated by centrifuging and washing to give 38% yield of dry product. Results from the second lot are shown in table below.

Waxy corn starch was acid hydrolyzed at 37% solids, 60° C. and 0.609 meq/g of acid. Samples were taken at 10 and 12.5 hours. Both samples were then reacted with octenyl succinic anhydride at 3% by weight based on original starch solids. The 10 hour sample was isolated, washed and dried to give 48% yield of dry product. The 12 hour sample was treated similarly.

The dried products were reslurried at 25% solids and sheared in the MICROFLUIDIZER, described above, using a refurbished 1351 module at 8,000 psi and 49° C. inlet temperature. Yield stress and analytical data are indicated in the table below and are compared to data for a control fragmented starch hydrolysate.

|  | OSA Reactive Treatment | Hydrolysis Time (hrs.) | b Value | Substitution (wt. %) | Yield Stress (Pascals) |
|---|---|---|---|---|---|
| Example 77 | Pre-hydrolysis | 10.5 | 0.53 | — | — |
|  |  | 12.0 | 0.58 | 1.04 | 2,813 |
| Example 78 | Post-hydrolysis | 10.0 | 0.47 | 1.00 | 1,879 |
|  |  | 12.25 | 0.33 |  |  |
| Control | None |  |  | 0.0 | 2,376 |

EXAMPLE 82

Danish Pastry

A dispersion of fragmented starch hydrolysate was prepared as follows: A roll-in was prepared was follows:

| Ingredients | Wt. % |
|---|---|
| Starch Hydrolysate of Run No. 5D | 25.44 |
| Potassium Sorbate (preservative) | 0.1 |
| High Fructose Corn Syrup (42% fructose, ISOSWEET 100, A. E. Staley Mfg. Co.) | 34.73 |
| Water | 34.73 |
| Emulsifier (DUR-LO, Van Den Bergh Foods) | 5.0 |

A mixture of the above was blended on a Tekmar mixer until visually homogeneous. The blend was then fragmented by processing through a Microfluidics M-100T, modified, MICROFLUIDIZER at 14,000 psi and an outlet temperature of 53° C. The resulting roll-in can be used to make a Danish as follows. First, a Danish bread dough is made as follows:

| Ingredients | Lb. | Oz. |
|---|---|---|
| Hard Wheat Flour | 80 | — |
| Soft Wheat Flour | 20 | — |
| Water (Variable) | 40 | — |
| Yeast (variable) | 3 | 12 |
| Salt | 1 | 9 |
| Malt | 1 | 4 |
| Sugar (part brown desirable) | 20 | — |
| Shortening (part butter is desirable) | 12 | 8 |
| Eggs (whole or mixed) | 20 | — |

Procedure

Mix Danish dough to full development or just enough to combine dough ingredients thoroughly. Either method will produce excellent Danish dough, granted the rolling-in is done properly and dough fermentation and subsequent handling are proper.

After mixing, divide dough into 10 to 12 pound pieces which will make for easy handling through the rolling-in process. Allow pieces to relax 20 to 30 minutes. Roll pieces three times as long as wide and about ½ to ¾ inch thick.

Spot roll-in over two-thirds of the top dough surface. Fold unspotted third over center third and remaining third over it. Roll it as was done before spotting it with roll-in; i.e., three times as long as wide and ½ to ¾ inch thick. Fold it in thirds; place on pre-chilled pan and in a dough retarder for 30 minutes where it should relax and loosen up.

Repeat this rolling, folding and relaxing process twice more to allow dough to age six hours or more before makeup into desired end product. Keep dough under refrigeration at all times. Temperature range desired, 36° to 40° F. Equip retarder to produce enough humidity to prevent dough and/or made-up units from crusting.

Roll-in should be rolled in at the rate of 4 to 6 ounces for each pound of dough.

EXAMPLE 83

A sample of starch hydrolysate powder from Run No. 4B was reslurried to 28% dry solids and sodium chloride (9% by weight of hydrolysate solids) was added. The pH was adjusted to 8.5 and the mixture was placed in a water bath, at 60° C., for 3 hours. After cooling, the insolubles were isolated with a lab centrifuge (1,500 rpm for 15 minutes) and reslurried and recentrifuged until a low conductivity was obtained (about 0.5% ash). The above was repeated on a second sample, but with a pH of 3.5 in the slurry. The yield stress of a 20% d.s. aqueous dispersion after fragmentation was much higher (approximately double) for both the sample treated at pH 8.5 and the sample at pH 3.5. The above procedure was repeated with samples from Run No. 5D with similar results.

What is claimed:

1. A method of preparing a starch hydrolysate comprising maintaining, for a period greater than 4.5 hours, a strongly acidic aqueous slurry comprised of a granular starch at a temperature greater than 55.5° C. and below both (i) the gelatinization temperature of said granular starch in said slurry and (ii) the atmospheric boiling point of said slurry, to hydrolyze a portion of said granular starch and retain a starch hydrolysate residue insoluble in said strongly acidic aqueous slurry and reducing the particle size of said starch hydrolysate residue by mechanical disintegration sufficient to reduce the particle size of substantially all of the particles of said starch hydrolysate residue to less than 15 microns.

2. A method of claim 1 wherein said starch is a granular corn starch and said period of time and said temperature are sufficient in conjunction to yield a starch hydrolysate residue having a weight average molecular weight of from about 4,000 to about 7,500.

3. A method of claim 1 wherein said maintaining is effective to produce a slurry having a dextrose content of the supernatant phase of said slurry of at least about 0.5% by weight of the supernatant phase.

4. A method of claim 1 wherein said slurry is comprised of a strong acid at a concentration of at least about 0.3N based upon the aqueous phase of said slurry.

5. A method of claim 1 further comprising spray drying said starch hydrolysate residue.

6. A method of claim 5 further comprising neutralizing and dewatering said slurry prior to said spray drying.

7. A method of claim 5 further comprising neutralizing said slurry and then spray drying said slurry without dewatering said slurry prior to said spray drying.

8. A method of claim 1 further comprising physically fragmenting a majority of the residual granules of said starch hydrolysate residue by mechanical disintegration.

9. A method of claim 8 further comprising neutralizing said slurry to produce a salt and then dewatering said slurry to remove at least a portion of said salt prior to said physically fragmenting.

10. A method of claim 8 further comprising neutralizing said slurry to produce a food acceptable salt in said slurry and then physically fragmenting the starch hydrolysate residue without dewatering said slurry.

11. A method of claim 1 wherein said granular starch is an amylose starch.

12. A method of claim 1 wherein said granular starch is an amylopectin starch.

13. A method of claim 1 wherein said maintaining is for a period greater than 14 hours.

14. A method of claim 1 wherein said maintaining is for a period of at least about 10 hours and said temperature is greater than 60° C.

15. A method of claim 1 further comprising measuring the dextrose concentration in a supernatant phase derived from said slurry, wherein said measuring is employed to determine the length of said period of said maintaining.

16. A method of separating a granular starch hydrolysate residue from a slurry with an aqueous liquid phase, the granules of said granular starch hydrolysate residue being susceptible to physical fragmentation, comprising:

diluting said aqueous liquid phase with a water-miscible organic solvent to form a macrofilterable aqueous-organic slurry;

macrofiltering said macrofilterable aqueous-organic slurry to collect a granular starch hydrolysate residue as a filter cake; and desolventizing said filter cake to produce an edible granular starch hydrolysate.

17. A method of preparing a starch hydrolysate comprising:

(a) maintaining, for a period greater than 4.5 hours, a strongly acidic aqueous slurry comprised of a granular starch at a temperature greater than 55.5° C and below both (i) the gelatinization temperature of said granular starch in said slurry and (ii) the atmospheric boiling point of said slurry, to hydrolyse a portion of said granular starch and retain a starch hydrolysate residue insoluble in said strongly acidic aqueous slurry;

(b) drying said starch hydrolysate residue by a means selected from the group consisting of spray drying and flash drying; and (c) reducing the particle size of said starch hydrolysate residue after said drying sufficient to reduce the particle size of substantially all of the particles of said starch hydrolysate residue to less than 15 microns.

18. A method of preparing a starch hydrolysate comprising:

(a) maintaining, for a period greater than 4.5 hours, a strongly acidic slurry comprised of a granular starch at a temperature greater than 55.5° C. and below both (i) the gelatinization temperature of said granular starch in said slurry and (ii) the atmospheric boiling point of said slurry, to hydrolyse a portion of said granular starch and retain a starch hydrolysate residue insoluble in said strongly acidic aqueous slurry; and (b) drying said starch hydrolysate residue by means selected from the group consisting of tray drying and belt drying.

19. A method of preparing a starch hydrolysate comprising:

maintaining, for a period greater than 4.5 hours, a strongly acidic aqueous slurry comprised of a granular starch at a temperature greater than 55.5° C. and below both (i) the gelatinization temperature of said granular starch in said slurry and (ii) the atmospheric boiling point of said slurry, to hydrolyse a substantial portion of said granular starch and retain a starch hydrolysate residue insoluble in said strongly acidic aqueous slurry;

physically fragmenting a majority of the residual granules of said starch hydrolysate residue, said physically fragmenting being accomplished with a minor amount of said starch hydrolysate residue in a major amount of an aqueous liquid, said hydrolysate being comprised of a major amount of cold-water insoluble hydrolysate and a minor amount of cold-water soluble hydrolysate; and drying said starch hydrolysate residue after said fragmenting to a microbiologically stable moisture content.

20. A method of claim 19 wherein said starch is a granular corn starch and said period of time and said temperature are sufficient in conjunction to yield a starch hydrolysate residue having a weight average molecular weight of from about 4,000 to about 7,500.

21. A method of claim 19 wherein said drying comprises spray drying said starch hydrolysate residue.

22. A method of claim 19 further comprising neutralizing said slurry to produce a salt and then dewatering said slurry to remove at least a portion of said salt prior to said physically fragmenting.

23. A method of claim 19 further comprising neutralizing said slurry to produce a food acceptable salt in said slurry and then physically fragmenting the starch hydrolysate residue without dewatering said slurry.

24. A method of preparing a starch hydrolysate, comprising:

maintaining for a period greater than about 4.5 hours a strongly acidic aqueous slurry which comprises a granular starch at a temperature greater than 55.5° C. and below both (i) the gelatinization temperature of said granular starch in said slurry and (ii) the atmospheric boiling point of said slurry, to hydrolyse a portion of said granular starch and retain a starch hydrolysate residue insoluble in said strongly acidic aqueous slurry; and reducing the particle size of said starch hydrolysate by mechanical disintegration.

25. The method of claim 24, where the strongly acidic aqueous slurry is acidified by a mineral acid.

26. A method of preparing a starch hydrolysate comprising maintaining, for a period greater than 4.5 hours, a strongly acidic aqueous slurry comprised of a granular starch at a temperature greater than 55.5° C. and below both (i) the gelatinization temperature of said granular starch in said slurry and (ii) the atmospheric boiling point of said slurry, to hydrolyze a portion of said granular starch and retain a starch hydrolysate residue insoluble in said strongly acidic aqueous slurry.

27. A method of separating a granular starch hydrolysate residue from a slurry with an aqueous liquid phase, the granules of said granular starch hydrolysate residue being susceptible to physical fragmentation, comprising:

diluting said aqueous liquid phase with a water-miscible organic solvent selected from the group consisting of lower alkanols, lower aliphatic esters, lower aliphatic ketones, glycols, and mixtures thereof, to form a macrofilterable aqueous-organic slurry;

macrofiltering said macrofilterable aqueous-organic slurry to collect a granular starch hydrolysate residue as a filter cake; and desolventizing said filter cake to produce an edible granular starch hydrolysate.

* * * * *

UNITED STATES PATENT AND TRADEMARK OFFICE
CERTIFICATE OF CORRECTION

PATENT NO. : 5,378,286
DATED : January 3, 1995
INVENTOR(S) : Chiou et al

It is certified that error appears in the above-indentified patent and that said Letters Patent is hereby corrected as shown below:

At column 27, line 2, "TW" should read --TB--.

In Claim 17, column 109, line 44, after "residue" insert --by mechanical disintegration--.

Signed and Sealed this

Twenty-seventh Day of June, 1995

Attest:

BRUCE LEHMAN

*Attesting Officer*     Commissioner of Patents and Trademarks